(12) United States Patent
Ballinger et al.

(10) Patent No.: US 6,365,726 B1
(45) Date of Patent: Apr. 2, 2002

(54) POLYNUCLEOTIDES ENCODING IL-1 HY2 POLYPEPTIDES

(75) Inventors: Dennis G. Ballinger, Menlo; John Ford, San Mateo; Alice Suk-Yue Ho, Union City; Hai Shan Lin, Castro Valley; Ann M. Pace, Scotts Valley, all of CA (US)

(73) Assignee: Hyseq, Inc., Sunnyvale, CA (US)

( * ) Notice: Subject to any disclaimer, the term of this patent is extended or adjusted under 35 U.S.C. 154(b) by 0 days.

(21) Appl. No.: 09/578,458

(22) Filed: May 22, 2000

Related U.S. Application Data

(63) Continuation-in-part of application No. 09/522,964, filed on Mar. 10, 2000, which is a continuation-in-part of application No. 09/316,081, filed on May 20, 1999, now Pat. No. 6,339,141.

(51) Int. Cl.[7] .......................... C07H 21/04; C12P 21/06; C12N 15/00; C12N 15/06
(52) U.S. Cl. .................. 536/23.52; 536/23.1; 536/23.5; 536/24.31; 435/69.1; 435/69.52; 435/320.1
(58) Field of Search .............................. 435/69.1, 69.52, 435/320.1, 23.1; 536/23.5, 23.52, 24.31; 530/350, 357

(56) References Cited

FOREIGN PATENT DOCUMENTS

| WO | WO 98/47921 | 10/1998 |
|----|-------------|---------|
| WO | WO 99/51744 | 10/1999 |

OTHER PUBLICATIONS

Carter et al., Purification, cloning, expression and biological characterization of an interleukin–1 receptor antagonist protein, Nature 344: 633–638 (Apr. 12, 1990).

Genebank Accession No.: AC016724, *Homo sapiens* chromosome 2 clone RP11–339F22 Working Draft Sequence, 12 unordered pieces, deposited by Waterston, R.H., dated Jul. 7, 2000.

Genebank Accession No.: AQ766579, Human Genomic Sperm Library: deposited by Mahairas G.G. et al., dated Jul. 30, 1999.

*Primary Examiner*—Jeffrey Stucker
*Assistant Examiner*—Jegatheesan Seharaseyon
(74) *Attorney, Agent, or Firm*—Marshall, Gerstein & Borun.

(57) ABSTRACT

The present invention provides novel nucleic acids encoding IL-1 Hy2, a novel member of the Interleukin-1 Receptor Antagonist family, the novel polypeptides encoded by these nucleic acids and uses of these and related products.

10 Claims, 7 Drawing Sheets

Figure 1B:
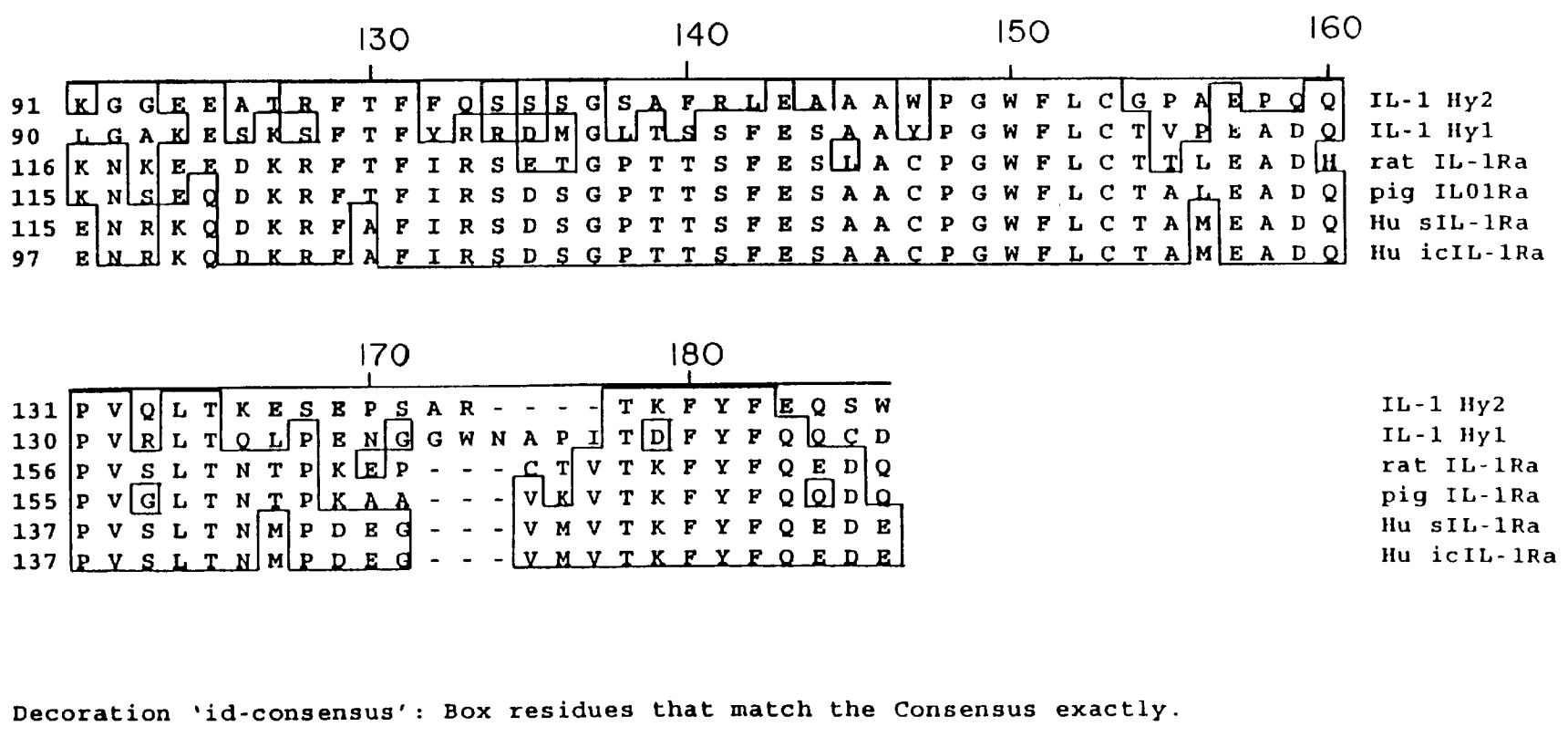

Decoration 'id-consensus': Box residues that match the Consensus exactly.

FIGURE 2A

SEQ ID NO.: 12

```
         10         20         30         40         50         60
         |          |          |          |          |          |
GGCAGTGGGA CTGGGTTTGA GCTGGGCTTA TCCTCCAACT GTGAGGGAGG CTACAGCACA  60
CTCCACCCCA CTCTCAGGGC TGGGAATTGT TGTGGCTCAG CTATTTGGGG GAATCTGTTT 120
TCCAGTTTCT CAGAACCAGC GCAAGCACAC ACATCCCAGG CTCACACCCC TGGTGGCTGG 180
ACTTGCTCCC GGATAGCCTC AGTCAGGGAG AGGCAGAGCT GCCTGGAGCC TGCTGGGCTG 240
GTGGAAGCCT TGGTGGATTC TGGCAGGCCA ATTATAGATG AATGGCCTGG GGAACCCGTG 300

310        320        330        340        350        360
         |          |          |          |          |          |
CAGCCCCGTG CTGAGTGGTT CTAAGCCCCA GCACGTCTGC CTCTGGCTTC ACCCAGCCTC 360
CTTTTCTAAC TGCCCTTCTC TCCTCCCCAT CAGTGAGGAC CAGACACCAC TGATTGCAGG 420
AATGTGTTCC CTCCCCATGG CAAGATACTA CATAATTAAA TATGCAGACC AGAAGGCTCT 480
ATACACAAGA GACGGCCAGC TGCTGGTGGG AGATCCTGTT GCAGACAACT GCTGTGCAGA 540
GAAGATCTGC ACACTTCCTA ACAGAGGCTT GGACCGCACC AAGGTCCCCA TTTTCCTGGG 600

610        620        630        640        650        660
         |          |          |          |          |          |
GATCCAGGGA GGGAGCCGCT GCCTGGCATG TGTGGAGACA GAAGAGGGGC CTTCCCTACA 660
GCTGGAGGAT GTGAACATTG AGGAACTGTA CAAAGGTGGT GAAGAGCCA CACGCTTCAC 720
CTTCTTCCAG AGCAGCTCAG GCTCCGCCTT CAGGCTTGAG GCTGCTGCCT GGCCTGGCTG 780
GTTCCTGTGT GGCCCCGGCA AGCCCCAGCA GCCAGTACAG CTCACCAAGG AGAGTGAGCC 840
CTCAGCCCGT ACCAAGTTTT ACTTTGAACA GAGCTGGGTAG GGAGACAGGA AACTGCGTTT 900
```

FIGURE 2B

```
      910        920        930        940        950        960
  |....|....|....|....|....|....|....|....|....|....|....|....|
TAGCCTTGTG CCCCCAAACC AAGCTCATCC TGCTCAGGGT CTATGGTAGG CAGAATAATG  960
TCCCCCGAAA TATGTCCACA TCCTAATCCC AAGATCTGTG CATATGTTAC CATACATGTC 1020
CAAAGAGGTT TTGCAAATGT GATTATGTTA AGGATCTTGA AATGAGGAGA CAATCCTGGG 1080
TTATCCTTGT GGGCTCAGTT TAATCACAAG AAGGAGGCAG GAAGGGAGAG TCAGAGAGAG 1140
AATGGAAGAT ACCATGCTTC TAATTTTGAA GATGGAGTGA GGGGCCTTGA GCCAACATAT 1200
      1210       1220       1230       1240       1250       1260
  |....|....|....|....|....|....|....|....|....|....|....|....|
GCTTGTGTTT TTAGAAGGAG GAAAAGCCAA GGGAACGGAT TCTCCCTCTAT AGTCTCCGGA 1260
AGGAACACAG CTCTTGACAC ATGGATTTCA GCTCAGTGAC ACCCATTTCA GACTTCTGAC 1320
CTCCACAACT ATAAAATAAT AAACTTGTGT TATTGTAAAC CTCTGG 1366
```

FIGURE 3

SEQ ID NO.: 13

```
         10         20         30         40         50
|....|....|....|....|....|....|....|....|....|....|
MNGLGNPCSP WLSGSKPQHV CLWLHPASFS NCPSLLPISE DQTPLIAGMC   50
SLPMARYYII KYADQKALYT RDGQLLVGDP VADNCCAEKI CTLPNRGLDR  100
TKVPIFLGIQ GGSRCLACVE TEEGPSLQLE DVNIEELYKG GEEATRFTFF  150
QSSSGSAFRL EAAAWPGWFL CQPAEPQQPV QLTKESEPSA RTKFYFEQSW  200
```

SEQ ID NO.: 14

FIGURE 4B

```
       910        920        930        940        950        960
   ....|....|....|....|....|....|....|....|....|....|....|....|
TAGCCTTGTG CCCCCAAACC AAGCTCATCC TGCTCAGGGT CTATGGTAGG CAGAATAATG    960
TCCCCCGAAA TATGTCCACA TCCTAATCCC AAGATCTGTG CATATGTTAC CATACATGTC   1020
CAAAGAGGTT TTGCAAATGT GATTATGTTA AGGATCTTGA AATGAGGAGA CAATCCTGGG   1080
TTATCCTTGT GGGCTCAGTT TAATCACAAG AAGGAGGCAG GAAGGGAGAG TCAGAGAGAG   1140
AATGGAAGAT ACCATGCTTC TAATTTTGAA GATGGAGTGA GGGGCCTTGA GCCAACATAT   1200
       1210       1220       1230       1240       1250       1260
   ....|....|....|....|....|....|....|....|....|....|....|....|
GCTTGTGTTT TTAGAAGGAG GAAAAGCCAA GGGAACGGAT TCTCCTCTAT AGTCTCCGGA   1260
AGGAACACAG CTCTTGACAC ATGGATTTCA GCTCAGTGAC ACCCATTTCA GACTTCTGAC   1320
CTCCACAACT ATAAAATAAT AAACTTGTGT TATTGTAAAC CTCTGG 1366
```

POLYNUCLEOTIDES ENCODING IL-1 HY2 POLYPEPTIDES

RELATED APPLICATIONS

This patent application is a continuation-in-part of U.S. application Ser. No. 09/522,964 filed Mar. 10, 2000 which is a continuation-in-part of U.S. application Ser. No. 09/316,081 filed May 20, 1999 now U.S. Pat. No. 6,339,141, all of which are incorporated herein by reference.

FIELD OF THE INVENTION

The present invention relates to a novel polynucleotide encoding a protein called IL-2 Hy2, which is structurally related to interleukin-1 receptor antagonist protein, along with therapeutic, diagnostic and research utilities for these and related products.

BACKGROUND

Cytokines are involved in inflammation and the immune response, in part through endothelial cell activation. Distinct immune-mediators such as tumor necrosis factor (TNF), interleukin-1 (IL-1), and gamma-interferon (IPN) appear to induce different but partially overlapping patterns of endothelial cell activation including increased procoagulant activity (Bevilaqua (1986) PNAS, 83:4533–4537), PGI and 2 production (Rossi (1985), Science, 229:174–176), HLA antigen expression (Pober (1987) J. Immunol., 138:3319–3324) and lymphocyte adhesion molecules (Carender (1987) J. Immunol., 138:2149–2154). These cytokines are also reported to cause hypotension, vascular hemorrhage, and ischemia (Goldblum et al. 1989, Tracey et al. Science 234:470, 1986). A major toxicity of these and other biological response modifiers is hypotension and vascular leakage (Dvorak (1989) J.N.C.I., 81:497–502).

IL-1 is produced by a number of cell types, including monocyte and macrophages, Langerhans cells, natural killer cells, B cells, T cell leukemic cell lines, neutrophils, endothelial cells, dendritic cells, melanoma cell lines, mesangial cells, astrocytes, glioma cells, microglial cells, fibroblasts and epithelial cells. Two forms of IL-1 have been isolated; IL-1α and IL-1β. They represent the products of two distinct genes and their mature forms are 159 and 153 amino acid proteins, respectively. These molecules are extremely potent and multi-functional cell activators, with a spectrum that encompasses cells of hematopoietic origin, from immature precursors to differentiated leukocytes, vessel wall elements, and cells of mesenchymal, nervous and epithelial origin. IL-1 also induces production of secondary cytokines, including IL-6, colony stimulating factors (CSFs) and chemokines. IL-1 is active as a hematopoietic growth and differentiation factor; activates endothelial cells in a pro-inflammatory and pro-thrombotic manner (including by inducing production of tissue factor and platelet activating factor); stimulates the release of corticotropin-releasing hormone (CRH) that ultimately causes release of corticosteroids by the adrenals; mediates the acute phase response (including by inducing hepatocyte production of acute phase proteins) and is a central mediator of local and systemic inflammatory reactions that can lead to sepsis and septic shock; is the primary endogenous pyrogen (causing fever); induces slow-wave sleep and anorexia; may play a role in destructive joint and bone diseases (including by inducing production of collagenase by synovial cells and metalloproteinases by chondrocytes); stimulates fibroblast proliferation and collagen synthesis; and may play a role in the pathogenesis of insulin-dependent type I diabetes through its toxicity for insulin-producing beta cells in Langerhans islets.

The IL-1 pathway consists of the two agonists IL-1α and IL-1β, a specific activation system (IL-2 converting enzyme), a receptor antagonist (IL-1Ra) produced in different isoforms and two high affinity receptors. IL-1α and IL-1β bind to two distinct IL-1 receptor types, IL-1 receptor type I (IL-1RI) and IL-1 receptor type II (IL-1RII), both of which are members of the immunoglobulin superfamily of receptors. Both types of receptors are usually coexpressed, although type I is the predominant form in fibroblasts and T cells, while type II is preferentially expressed on B cells, monocytes and neutrophils. IL-1RI and IL-1RII have different affinities for the three ligands of the IL-1 family (IL-1α, IL-1β and IL-1Ra). In particular, IL-1Ra binds to the type I receptor with an affinity similar to that of IL-1α, while IL-1Ra binds to the type II receptor 100-fold less efficiently than the type I receptor. There is evidence indicating that IL-1 induced activities are mediated exclusively via the type I receptor, whereas the type II receptor has no signaling activity and inhibits IL-1 activities by acting as a decoy for IL-1.

IL-1 receptor antagonist (IL-1Ra or IRAP) binds to the IL-1 receptor with affinity similar to that of IL-1 but has no IL-1-like activity, even at very high concentrations, and thus inhibits (antagonizes) the activity of IL-1. The purified IL-1Ra molecule has a molecular weight of approximately 22 kD and is believed to be glycosylated. It has limited sequence similarity to IL-1α and IL-1β at the amino acid level (19% and 26%, respectively). There appear to be at least two isoforms of IL-1Ra, including a soluble form and an intracellular form generated by an alternative splicing event. IL-1Ra appears to be produced by monocytes, macrophages, neutrophils and fibroblasts; keratinocytes and cells of epithelial origin produce almost exclusively the intracellular form. In humans, the gene for IL-1Ra has been localized to the long arm of chromosome 2, which is the same region where IL-1α and IL-1β, as well as IL-1RI and IL-1RII, are found.

The ability of IL-1 to modify biological responses has been demonstrated in a variety of studies. For example, the administration of IL-1 to rabbits (Wakabayashi et al., FASEB J 1991;5:338; Okusawa et al. J Clin Invest 1988;81:1162; Ohlsson et al., Nature 1990;348:550; Aiura, et al. Cytokine 1991;4:498) and primates (Fischer et al. Am J Physiol 1991;261:R442) has been shown to result in hypotension, tachycardia, lung edema, renal failure, and, eventually, death, depending on the dose. When the serum from the IL-1 treated animals is examined, the elevation of other cytokines is evident, mimicking the levels seen in acute pancreatitis in humans. (Guice et al., J Surg Res 1991;51:495–499; Heath et al., Pancreas 1993;66:41–45) There is a large body of evidence currently available which supports the role of IL-1 as a major mediator of the systemic response to diseases such as sepsis and pancreatitis and as an activator of the remaining members of the cytokine cascade. (Dinarello et al., Arch Surg 1992;127:1350–1353).

IL-1 is a key mediator in the inflammatory response (for reviews, see Dinarello (1991) Blood 77:1627–1652; Dinarello et al. (1993) New England J. Med. 328:106–113; Dinarello (1994) FASEB J. 8:1314–1325). The importance of IL-1 in inflammation has been demonstrated by the ability of the highly specific IL-1 receptor antagonist protein to relieve inflammatory conditions (for review, see Dinarello (1991) Blood 77:1627–1652; Dinarello et al. (1993) New England J. Med. 328:106–113; Dinarello (1994) FASEB J. 8:1314–1325; Dinarello (1993) Immunol. Today 14:260–264). Many of the proinflammatory effects of IL-1, such as the upregulation of cell adhesion molecules on vascular endothelia, are exerted at the level of transcriptional regulation. The transcriptional activation by IL-1 of cell adhesion molecules and other genes involved in the inflammatory response appears to be mediated largely by NF-kappa B (Shirakawa et al. (1989) Molc. Cell Biol. 9:2424–2430; Osborn et al., (1989) Proc. Natl. Acad. Sci. USA 86:2336–2340; Krasnow et al., (1991) Cytokine 3:372–379; Collins et al., (1993) Trends Cardiovasc. Med. 3:92–97). In response to IL-1, the NF-kappa B inhibitory factor I kappa B is degraded and NF-kappa B is released from its inactive cytoplasmic state to localize within the nucleus where it binds DNA and activates transcription (Liou et al. (1993) Curr. Opin. Cell Biol. 5:477–487; Beg et al., (1993) Mol. Cell. Bid. 13:3301–3310).

IL-1 is also a mediator of septic shock. Septic shock, a life-threatening complication of bacterial infections, affects 150,000 to 300,000 patients annually in the United States (Parrillo, J. E. (1989), Septic Shock in Humans: Clinical Evaluation, Pathogenesis, and Therapeutic Approach (2nd ed.) In: Textbook of Critical Care Shoemaker, et al., editors, Saunders Publishing Co., Philadelphia, Pa., pp. 1006). The cardiovascular collapse and multiple metabolic derangements associated with septic shock are due largely to bacterial endotoxin (ET), which has been shown to elicit a septic shock-like condition when administered to animals (Natanson, et al. (1989), Endotoxin and Tumor Necrosis Factor Challenges in Dogs Simulate the Cardiovascular Profile of Human Septic Shock, J. Exp. Med. 169:823).

Thus, there is a great need for modulators of IL-1 which may be useful for modulating inflammation and the immune response.

SUMMARY OF THE INVENTION

The compositions of the present invention include novel isolated polypeptides, in particular, novel human lnterleukin-1 Hy2 (IL-1 Hy2) proteins and active variants thereof, isolated polynucleotides encoding such polypeptides, including recombinant DNA molecules, cloned genes or degenerate variants thereof, especially naturally occurring variants such as allelic variants, antisense polynucleotide molecules, and antibodies that specifically recognize one or more epitopes present on such polypeptides, as well as hybridomas producing such antibodies.

The compositions of the present invention additionally include vectors, including expression vectors, containing the polynucleotides of the invention, cells genetically engineered to contain such polynucleotides and cells genetically engineered to express such polynucleotides.

The polynucleotides of the invention include naturally occurring or wholly or partially synthetic DNA, e.g., cDNA and genomic DNA, and RNA, e.g., mRNA. The isolated polynucleotides of the invention include, but are not limited to, a polynucleotide encoding a polypeptide comprising the amino acid sequence of SEQ ID NOS: 2, 4 or 13. The isolated polynucleotides of the invention further include, but are not limited to, a polynucleotide comprising the nucleotide sequence of SEQ ID NOS: 1, 12 or 14; a polynucleotide comprising the full length protein coding sequence of SEQ ID NOS: 1, 12 or 14; and a polynucleotide comprising the nucleotide sequence of the mature protein coding sequence of SEQ ID NOS: 1, 12 or 14. The polynucleotides of the present invention also include, but are not limited to, polynucleotides that encode polypeptides with IL-1 Hy2 activity and that hybridize under stringent hybridization conditions to the complement of (a) the nucleotide sequence of SEQ ID NOS: 1, 12 or 14, or (b) a nucleotide sequence encoding the amino acid sequence of SEQ ID 2, 4 or 13; a polynucleotide which is an allelic variant of any polynucleotide recited above; a polynucleotide which encodes a species homologue of any of the proteins recited above; or a polynucleotide that encodes a polypeptide comprising a specific domain or truncation of the polypeptide having an amino acid sequence of SEQ ID NOS: 2, 4 or 13.

The polynucleotides of the present invention still further include, but are not limited to, a polynucleotide comprising the nucleotide sequence of the cDNA insert of clone pIL-1Hy2 deposited on May 21, 1999 under Accession No. PTA-96 with the American Type Culture Collection (ATCC; 10801 University Blvd., Manassas, Va., 20110–2209, U.S.A.) or an IL-1 Hy2 protein coding portion thereof, such as the full length protein coding sequence or the mature protein coding sequence.

The polynucleotides of the invention additionally include the complement of any of the polynucleotides recited above.

A collection as used in this application can be a collection of only one polynucleotide. The collection of sequence information or identifying information of each sequence can be provided on a nucleic acid array. In one embodiment, segments of sequence information are provided on a nucleic acid array to detect the polynucleotide that contains the segment. The array can be designed to detect nucleic acids that are perfectly complementary (full-match) or mismatched to the polynucleotide that contains the segment. The collection can also be provided in a computer-readable format.

The isolated polypeptides of the invention include, but are not limited to, a polypeptide comprising the amino acid sequence of SEQ ID NOS: 2, 4 or 13, or the amino acid sequence encoded by the cDNA insert of clone pIL-1 Hy2, or a portion thereof corresponding to the full length or mature protein. Polypeptides of the invention also include polypeptides with IL-1 Hy2 activity that are encoded by (a) polynucleotides encoding SEQ ID NOS: 2 or 13 (b) polynucleotides that hybridize to the complement of the polynucleotides of (a) under stringent hybridization conditions. Biologically or immunologically active variants of the IL-1Ra protein sequence of SEQ ID NOS: 2, 4 or 13 and "substantial equivalents" thereof (e.g., with 65%, 70%, 75%, 80%, 85%, 90%, 95%, 98% or 99% amino acid identity) that retain IL-1 Hy2 activity, preferably IL-1 antagonist activity, are also contemplated. The polypeptides of the invention may be wholly or partially chemically synthesized but are preferably produced by recombinant means using the genetically engineered cells (e.g. host cells) of the invention.

Protein compositions of the present invention may further comprise an acceptable carrier, such as a hydrophilic, e.g., pharmaceutically acceptable, carrier.

The invention also relates to methods for producing polypeptides of the invention comprising growing a culture of the cells of the invention in a suitable culture medium under conditions permitting expression of the desired polypeptide, and purifying the protein from the cells or the culture medium. Preferred embodiments include those in which the protein produced by such process is a mature form of the protein.

Polynucleotides according to the invention have numerous applications in a variety of techniques known to those skilled in the art of molecular biology. These techniques include use as hybridization probes, use as oligomers for PCR, use for chromosome and gene mapping, use in the recombinant production of protein, and use in generation of anti-sense DNA or RNA, their chemical analogs and the like. For example, when the expression of an mRNA is largely restricted to a particular cell or tissue type, polynucleotides of the invention can be used as hybridization probes to detect the presence of the particular cell or tissue mRNA in a sample using, e.g., in situ hybridization.

In other exemplary embodiments, the polynucleotides are used in diagnostics as expressed sequence tags for identifying expressed genes or, as well known in the art and exemplified by Vollrath et al., Science 258:52–59 (1992), as expressed sequence tags for physical mapping of the human genome.

The polypeptides according to the invention can be used in a variety of conventional procedures and methods that are currently applied to other proteins. For example, a polypeptide of the invention can be used to generate an antibody that specifically binds the polypeptide. The polypeptides of the invention can also be used as molecular weight markers, and as a food supplement. Transgenic animals with altered expression of the polypeptides of the invention (i.e. knock out animals or animals overexpressing IL-2 Hy2) are also contemplated.

Methods are also provided for preventing, treating or ameliorating a medical condition which comprises administering to a mammalian subject a therapeutically effective amount of a composition comprising a protein of the present invention and a pharmaceutically acceptable carrier.

In particular, the polypeptides and polynucleotides of the invention can be utilized, for example, as part of methods for the prevention and/or treatment of IL-1, IL-18 and/or IL-12 mediated disorders including disorders involving sepsis (and associated conditions such as fever, tachycardia, tachypnea, cytokine overstimulation, increased vascular permeability, hypotension, complement activation, disseminated intravascular coagulation, anemia, thrombocytopenia, leukopenia, pulmonary edema, adult respiratory distress syndrome, intestinal ischemia, renal insufficiency and failure, metabolic acidosis and multiorgan dysfunction syndrome), endotoxic shock, cytokine induced shock, thrombosis, acute pancreatitis, rheumatoid or reactive arthritis, chronic inflammatory arthritis, vasculitis, lupus, immune complex glomerulonephritis, pancreatic cell damage from diabetes mellitus type 1, allograft and xenograft transplantation, graft versus host disease, inflammatory bowel disease, inflamation associated with pulmonary disease, other autoimmune disease or inflammatory disease, an antiproliferative agent such as for acute or chronic myelogenous leukemia, ovarian carcinoma, or in the prevention of premature labor secondary to intrauterine infections, bone degenerative diseases such as osteoporosis, and neurodegenerative disorders such as Alzheimer disease.

Concurrent administration of other agents that inhibit the production or activity of IL-1 (such as GM-CSF, IL-4, IL-10, IL-13 and transforming growth factor-beta) or other anti-inflammatory agents (such as IL-1Ra, IL-1Ra-like IL-1 Hy1 proteins described in co-owned, co-pending U.S. application Ser. No. 09/287,210 filed Apr. 5, 1999, incorporated herein by reference, anti-TNF, corticosteroids, immunosuppressive agents) is also contemplated according to the invention.

The methods of the present invention further relate to methods for detecting the presence of the polynucleotides or polypeptides of the invention in a sample. Such methods can, for example, be utilized as part of prognostic and diagnostic evaluation of disorders as recited above and for the identification of subjects exhibiting a predisposition to such conditions. Furthermore, the invention provides methods for evaluating the efficacy of drugs, and monitoring the progress of patients, involved in clinical trials for the treatment of disorders as recited above.

The invention also provides methods for the identification of compounds that modulate (i.e., increase or decrease) the expression or activity of the polynucleotides and/or polypeptides of the invention. Such methods can be utilized, for example, for the identification of compounds that can ameliorate symptoms of disorders as recited above. Such methods can include, but are not limited to, assays for identifying compounds and other substances that interact with (e.g., bind to) the polypeptides of the invention.

The methods of the invention also include methods for the treatment of disorders as recited above which may involve the administration of such compounds to individuals exhibiting symptoms or tendencies related to disorders as recited above. In addition, the invention encompasses methods for treating diseases or disorders as recited above by administering compounds and other substances that modulate the overall activity of the target gene products. Compounds and other substances can effect such modulation either on the level of target gene expression or target protein activity.

The invention further provides a method of treating an inflammatory disease state mediated by IL-18 comprising administering to a subject in need thereof an amount of an IL-1 Hy2 polynucleotide, polypeptide or agonist effective to inhibit IL-18 activity. Also provided are in vitro and in vivo methods of inhibiting IL-18 activity.

BRIEF DESCRIPTION OF THE DRAWINGS

FIGS. 1A–1B show an alignment of the amino acid sequence of IL-1 Hy2 (SEQ ID NO. 2) with the sequences of IL-1Hy1 (described in co-owned, co-pending U.S. Ser. No. 09/287,210 filed Apr. 5, 1999), rat IL-1Ra, pig IL-1Ra, secreted human IL-1Ra (Hu sIL-1Ra) and intracellular human IL-1Ra (Hu icIL-1Ra), SEQ ID NOS: 5–9, respectively. In these figures, A—Alanine; R—Arginine; N—Asparagine; D—Aspartic Acid; C—Cysteine; E—Glutamic Acid; Q—Glutamine; G—Glycine; H—Histidine; I—Isoleucine; L—Leucine; K—Lysine; M—Methionine; F—Phenylalanine; P—Proline; S—Serine; T—Threonine; W—Tryptophan; Y—Tyrosine; V—Valine; X—any of the twenty amino acids. Gaps are presented as dashes. Amino acid numbers for all sequences are labelled accordingly. Boxed residues indicate consensus or conserved sequence.

FIG. 2 sets forth SEQ ID NO: 12 which represents the predicted cDNA sequence based on the human genomic sequence of IL-1 Hy2.

FIG. 3 sets forth SEQ ID NO: 13 which represents the human amino acid sequence encoded by the longer open reading frame of SEQ ID NO: 12 which is an alternative form of the IL-1 Hy2 polypeptide.

DETAILED DESCRIPTION OF THE INVENTION

I. DEFINITIONS

Figure 4A:
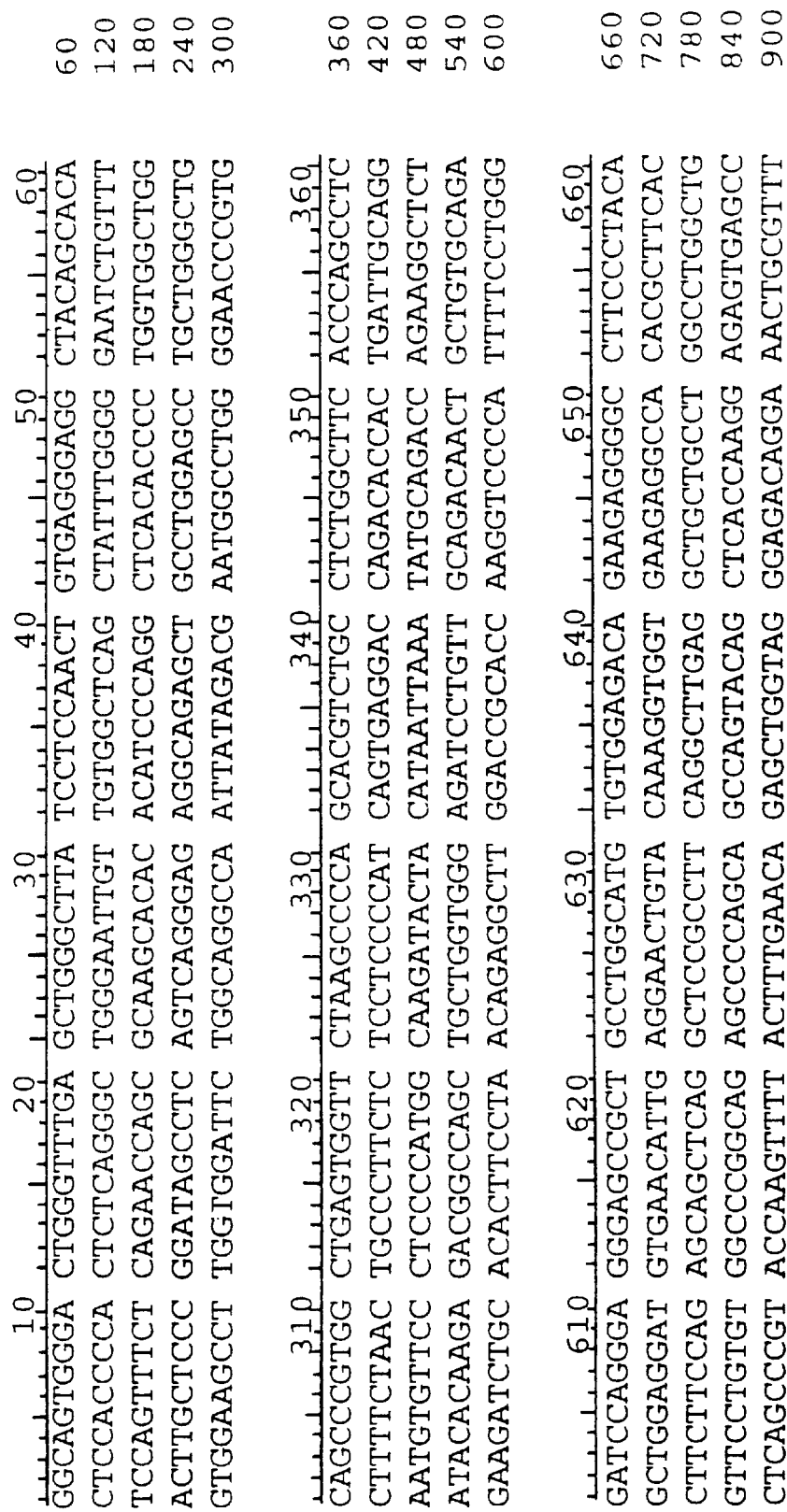
FIG. 4 sets forth SEQ ID NO: 14 which represents the cDNA sequence of human IL-1 Hy2 clones which extends the 5' region of SEQ ID NO: 1.

The term "nucleotide sequence" refers to a heteropolymer of nucleotides or the sequence of these nucleotides. The terms "nucleic acid" and "polynucleotide" are also used interchangeably herein to refer to a heteropolymer of nucleotides. Generally, nucleic acid segments provided by this invention may be assembled from fragments of the genome and short oligonucleotide linkers, or from a series of oligonucleotides, or from individual nucleotides, to provide a synthetic nucleic acid which is capable of being expressed in a recombinant transcriptional unit comprising regulatory elements derived from a microbial or viral operon, or a eukaryotic gene.

The terms "oligonucleotide fragment" or a "polynucleotide fragment", "portion," or "segment" is a stretch of polypeptide nucleotide residues which is long enough to use in polymerase chain reaction (PCR) or various hybridization procedures to identify or amplify identical or related parts of mRNA or DNA molecules.

The terms "oligonucleotides" or "nucleic acid probes" are prepared based on the polynucleotide sequences provided in the present invention. Oligonucleotides comprise portions of such a polynucleotide sequence having at least about 15 nucleotides and usually at least about 20 nucleotides. Nucleic acid probes comprise portions of such a polynucleotide sequence having fewer nucleotides than about 6 kb, usually fewer than about 1 kb. After appropriate testing to eliminate false positives, these probes may, for example, be used to determine whether specific mRNA molecules are present in a cell or tissue or to isolate similar nucleic acid sequences from chromosomal DNA as described by Walsh et al. (Walsh, P. S. et al., 1992, PCR Methods Appl 1:241–250).

The term "probes" includes naturally occurring or recombinant or chemically synthesized single- or double-stranded nucleic acids. They may be labeled by nick translation, Klenow fill-in reaction, PCR or other methods well known in the art. Probes of the present invention, their preparation and/or labeling are elaborated in Sambrook, J. et al., 1989, Molecular Cloning: A Laboratory Manual, Cold Spring Harbor Laboratory, NY; or Ausubel, F. M. et al., 1989, Current Protocols in Molecular Biology, John Wiley & Sons, New York N.Y., both of which are incorporated herein by reference in their entirety.

The term "stringent" is used to refer to conditions that are commonly understood in the art as stringent. Stringent conditions can include highly stringent conditions (i.e., hybridization to filter-bound DNA under in 0.5 M $NaHPO_4$, 7% sodium dodecyl sulfate (SDS), 1 mM EDTA at 65° C., and washing in 0.1×SSC/0.1% SDS at 68° C.), and moderately stringent conditions (i.e., washing in 0.2×SSC/0.1% SDS at 42° C.).

In instances wherein hybridization of deoxyoligonucleotides is concerned, additional exemplary stringent hybridization conditions include washing in 6×SSC/0.05% sodium pyrophosphate at 37° C. (for 14-base oligos), 48° C. (for 17-base oligos), 55° C. (for 20-base oligos), and 60° C. (for 23-base oligos).

The term "recombinant," when used herein to refer to a polypeptide or protein, means that a polypeptide or protein is derived from recombinant (e.g., microbial or mammalian) expression systems. "Microbial" refers to recombinant polypeptides or proteins made in bacterial or fungal (e.g., yeast) expression systems. As a product, "recombinant microbial" defines a polypeptide or protein essentially free of native endogenous substances and unaccompanied by associated native glycosylation. Polypeptides or proteins expressed in most bacterial cultures, e.g., E. coli, will be free of glycosylation modifications; polypeptides or proteins expressed in yeast will have a glycosylation pattern in general different from those expressed in mammalian cells.

The term "recombinant expression vehicle or vector" refers to a plasmid or phage or virus or vector, for expressing a polypeptide from a DNA (RNA) sequence. An expression vehicle can comprise a transcriptional unit comprising an assembly of (1) a genetic element or elements having a regulatory role in gene expression, for example, promoters or enhancers, (2) a structural or coding sequence which is transcribed into mRNA and translated into protein, and (3) appropriate transcription initiation and termination sequences. Structural units intended for use in yeast or eukaryotic expression systems preferably include a leader sequence enabling extracellular secretion of translated protein by a host cell. Alternatively, where recombinant protein is expressed without a leader or transport sequence, it may include an N-terminal methionine residue. This residue may or may not be subsequently cleaved from the expressed recombinant protein to provide a final product.

The term "recombinant expression system" means host cells which have stably integrated a recombinant transcriptional unit into chromosomal DNA or carry the recombinant transcriptional unit extrachromosomally. Recombinant expression systems as defined herein will express heterologous polypeptides or proteins upon induction of the regulatory elements linked to the DNA segment or synthetic gene to be expressed. This term also means host cells which have stably integrated a recombinant genetic element or elements having a regulatory role in gene expression, for example, promoters or enhancers. Recombinant expression systems as defined herein will express polypeptides or proteins endogenous to the cell upon induction of the regulatory elements linked to the endogenous DNA segment or gene to be expressed. The cells can be prokaryotic or eukaryotic.

The term "open reading frame," ORF, means a series of nucleotide triplets coding for amino acids without any termination codons and is a sequence translatable into protein.

The term "expression modulating fragment," EMF, means a series of nucleotides which modulates the expression of an operably linked ORF or another EMF.

As used herein, a sequence is said to "modulate the expression of an operably linked sequence" when the expression of the sequence is altered by the presence of the EMF. EMFs include, but are not limited to, promoters, and promoter modulating sequences (inducible elements). One class of EMFs are fragments which induce the expression or an operably linked ORF in response to a specific regulatory factor or physiological event.

As used herein, an "uptake modulating fragment," UMF, means a series of nucleotides which mediate the uptake of a linked DNA fragment into a cell. UMFs can be readily identified using known UMFs as a target sequence or target motif with the computer-based systems described below.

The presence and activity of a UMF can be confirmed by attaching the suspected UMF to a marker sequence. The resulting nucleic acid molecule is then incubated with an appropriate host under appropriate conditions and the uptake of the marker sequence is determined. As described above, a UMF will increase the frequency of uptake of a linked marker sequence.

The term "active" refers to those forms of the polypeptide which retain the biologic and/or immunologic activities of any naturally occurring polypeptide. According to the invention, the term "biologically active" with reference to IL-1 Hy2 means that the polypeptide retains at least one of the biological activities, preferably the IL-1 antagonist activity, of human IL-1 Hy2, while the term "immunologically active" with reference to IL-1 Hy2 means that the polypeptide retains at least one of the immunologic or antigenic activities of human IL-1 Hy2.

The term "naturally occurring polypeptide" refers to polypeptides produced by cells that have not been genetically engineered and specifically contemplates various polypeptides arising from post-translational modifications of the polypeptide including, but not limited to, acetylation, carboxylation, glycosylation, phosphorylation, lipidation and acylation.

The term "derivative" refers to polypeptides chemically modified by such techniques as ubiquitination, labeling (e.g., with radionuclides or various enzymes), pegylation (derivatization with polyethylene glycol) and insertion or substitution by chemical synthesis of amino acids such as ornithine, which do not normally occur in human proteins.

The term "variant" (or "analog") refers to any polypeptide differing from naturally occurring polypeptides by amino acid insertions, deletions, and substitutions, created using recombinant DNA techniques. Guidance in determining which amino acid residues may be replaced, added or deleted without abolishing activities of interest, such as IL-1 antagonistic activity, may be found by comparing the sequence of the particular polypeptide with that of homologous human or other mammalian peptides e.g. IL-1Ra, IL-1 Hy1, or IL-1, and minimizing the number of amino acid sequence changes made in regions of high homology (conserved regions) or by replacing amino acids with consensus sequence.

Preferably, amino acid "substitutions" are the result of replacing one amino acid with another amino acid having similar structural and/or chemical properties, i.e., conservative amino acid replacements. "Conservative" amino acid substitutions may be made on the basis of similarity in polarity, charge, solubility, hydrophobicity, hydrophilicity, and/or the amphipathic nature of the residues involved. For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid. "Insertions" or "deletions" are typically in the range of about 1 to 5 amino-acids. The variation allowed may be experimentally determined by systematically making insertions, deletions, or substitutions of amino acids in a polypeptide molecule using recombinant DNA techniques and assaying the resulting recombinant variants for activity.

Alternatively, where alteration of function is desired, insertions, deletions or non-conservative alterations can be engineered to produce altered polypeptides. Such alterations can, for example, alter one or more of the biological functions or biochemical characteristics of the polypeptides of the invention. For example, such alterations may change polypeptide characteristics such as ligand-binding affinities, interchain affinities, or degradation/turnover rate. Further, such alterations can be selected so as to generate polypeptides that are better suited for expression, scale up and the like in the host cells chosen for expression. For example, cysteine residues can be deleted or substituted with another amino acid residue in order to eliminate disulfide bridges.

As used herein, "substantially equivalent" can refer both to nucleotide and amino acid sequences, for example a mutant sequence, that varies from a reference sequence by one or more substitutions, deletions, or additions, the net effect of which does not result in an adverse functional dissimilarity between the reference and subject sequences. Typically, such a substantially equivalent sequence varies from one of those listed herein by no more than about 20% (i.e., the number of individual residue substitutions, additions, and/or deletions in a substantially equivalent sequence, as compared to the corresponding reference sequence, divided by the total number of residues in the substantially equivalent sequence is about 0.2 or less). Such a sequence is said to have 80% sequence identity to the listed sequence. In one embodiment, a substantially equivalent, e.g., mutant, sequence of the invention varies from a listed sequence by no more than 10% (90% sequence identity); in a variation of this embodiment, by no more than 5% (95% sequence identity); and in a further variation of this embodiment, by no more than 2% (98% sequence identity). Substantially equivalent, e.g., mutant, amino acid sequences according to the invention generally have at least 95% sequence identity with a listed amino acid sequence, whereas substantially equivalent nucleotide sequence of the invention can have lower percent sequence identities, taking into account, for example, the redundancy or degeneracy of the genetic code. For the purposes of the present invention, sequences having substantially equivalent biological activity and substantially equivalent expression characteristics are considered substantially equivalent. For the purposes of determining equivalence, truncation of the mature sequence (e.g., via a mutation which creates a spurious stop codon) should be disregarded. Sequence identity may be determined, e.g., using the Jotun Hein method.

Nucleic acid sequences encoding such substantially equivalent sequences, e.g., sequences of the recited percent identities, can routinely be isolated and identified via standard hybridization procedures well known to those of skill in the art.

Where desired, an expression vector may be designed to contain a "signal or leader sequence" which will direct the polypeptide through the membrane of a cell. Such a sequence may be naturally present on the polypeptides of the present invention or provided from heterologous protein sources by recombinant DNA techniques.

A polypeptide "fragment," "portion," or "segment" is a stretch of amino acid residues of at least about 5 amino acids, often at least about 7 amino acids, typically at least about 9 to 13 amino acids, and, in various embodiments, at least about 17 or more amino acids. To be active, any polypeptide must have sufficient length to display biologic and/or immunologic activity.

Alternatively, recombinant variants encoding these same or similar polypeptides may be synthesized or selected by making use of the "redundancy" in the genetic code. Various codon substitutions, such as the silent changes which produce various restriction sites, may be introduced to optimize cloning into a plasmid or viral vector or expression in a particular prokaryotic or eukaryotic system. Mutations in the polynucleotide sequence may be reflected in the polypeptide or domains of other peptides added to the polypeptide to modify the properties of any part of the polypeptide, to change characteristics such as ligand-binding affinities, interchain affinities, or degradation/turnover rate.

The term "activated" cells as used in this application are those which are engaged in extracellular or intracellular membrane trafficking, including the export of neurosecretory or enzymatic molecules as part of a normal or disease process.

The term "purified" as used herein denotes that the indicated nucleic acid or polypeptide is present in the substantial absence of other biological macromolecules, e.g., polynucleotides, proteins, and the like. In one embodiment, the polynucleotide or polypeptide is purified such that it constitutes at least 95% by weight, more preferably at least 99.8% by weight, of the indicated biological macromolecules present (but water, buffers, and other small molecules, especially molecules having a molecular weight of less than 1000 daltons, can be present).

The term "isolated" as used herein refers to a nucleic acid or polypeptide separated from at least one other component (e.g., nucleic acid or polypeptide) present with the nucleic acid or polypeptide in its natural source. In one embodiment, the nucleic acid or polypeptide is found in the presence of (if anything) only a solvent, buffer, ion, or other component normally present in a solution of the same. The terms "isolated" and "purified" do not encompass nucleic acids or polypeptides present in their natural source.

The term "infection" refers to the introduction of nucleic acids into a suitable host cell by use of a virus or viral vector.

The term "transformation" means introducing DNA into a suitable host cell so that the DNA is replicable, either as an extrachromosomal element, or by chromosomal integration.

The term "transfection" refers to the taking up of an expression vector by a suitable host cell, whether or not any coding sequences are in fact expressed.

The term "intermediate fragment" means a nucleic acid between 5 and 1000 bases in length, and preferably between 10 and 40 bp in length.

The term "secreted" includes a protein that is transported across or through a membrane, including transport as a result of signal sequences in its amino acid sequence when it is expressed in a suitable host cell. "Secreted" proteins include without limitation proteins secreted wholly (e.g., soluble proteins) or partially (e.g., receptors) from the cell in which they are expressed. "Secreted" proteins also include without limitation proteins which are transported across the membrane of the endoplasmic reticulum. "Secreted" proteins are also intended to include proteins containing non-typical signal sequences (e.g. Interleukin-1 Beta, see Krasney, P. A. and Young, P. R. (1992) Cytokine 4(2):134–143) and factors released from damaged cells (e.g. Interleukin-1 Receptor Antagonist, see Arend, W. P. et. al. (1998) Annu. Rev. Immunol. 16:27–55).

Each of the above terms is meant to encompasses all that is described for each, unless the context dictates otherwise.

NUCLEIC ACIDS AND POLYPEPTIDES OF THE INVENTION

Nucleotide and amino acid sequences of the invention are reported below. Fragments of the proteins of the present invention which are capable of exhibiting biological activity are also encompassed by the present invention. Fragments of the protein may be in linear form or they may be cyclized using known methods, for example, as described in H. U. Saragovi, et al., Bio/Technology 10, 773–778 (1992) and in R. S. McDowell, et al., J. Amer. Chem. Soc. 114, 9245–9253 (1992), both of which are incorporated herein by reference. Such fragments may be fused to carrier molecules such as immunoglobulins for many purposes, including increasing the valency of protein binding sites. For example, fragments of the protein may be fused through "linker" sequences to the Fc portion of an immunoglobulin. For a bivalent form of the protein, such a fusion could be to the Fc portion of an IgG molecule. Other immunoglobulin isotypes may also be used to generate such fusions. For example, a protein-IgM fusion would generate a decavalent form of the protein of the invention.

The present invention also provides both full-length and mature forms (for example, without a signal sequence or precusor sequence) of the disclosed proteins. The full-length form of the such proteins is identified in the sequence listing by translation of the nucleotide sequence of each disclosed clone. The mature form of such protein may be obtained by expression of the disclosed full-length polynucleotide in a suitable mammalian cell or other host cell. The sequence of the mature form of the protein is also determinable from the amino acid sequence of the full-length form. Where protein of the present invention is membrane bound, soluble forms of the protein are also provided. In such forms part or all of the regions causing the protein to be membrane bound are deleted so that the protein is fully secreted from the cell in which it is expressed.

The present invention also provides genes corresponding to the cDNA sequences disclosed herein. The corresponding genes can be isolated in accordance with known methods using the sequence information disclosed herein. Such methods include the preparation of probes or primers from the disclosed sequence information for identification and/or amplification of genes in appropriate genomic libraries or other sources of genomic materials. Species homologs of the disclosed polynucleotides and proteins are also provided by the present invention. Species homologs may be isolated and identified by making suitable probes or primers from the sequences provided herein and screening a suitable nucleic acid source from the desired species. The invention also encompasses allelic variants of the disclosed polynucleotides or proteins; that is, naturally-occurring alternative forms of the isolated polynucleotide which also encode proteins which are identical, homologous or related to that encoded by the polynucleotides. The compositions of the present invention include isolated polynucleotides, including recombinant DNA molecules, cloned genes or degenerate variants thereof, especially naturally occurring variants such as allelic variants, novel isolated polypeptides, and antibodies that specifically recognize one or more epitopes present on such polypeptides. Species homologs of the disclosed polynucleotides and proteins are also provided by the present invention. Species homologs may be isolated and identified by making suitable probes or primers from the sequences provided herein and screening a suitable nucleic acid source from the desired species. The invention also encompasses allelic variants of the disclosed polynucleotides or proteins; that is, naturally-occurring alternative forms of the isolated polynucleotide which also encode proteins which are identical, homologous or related to that encoded by the polynucleotides.

DESCRIPTION OF SEQUENCES

SEQ ID NO: 1 sets forth one preferred nucleotide sequence of IL-1 Hy2 which contains a protein coding region from nucleotides 54 through 509.

SEQ ID NO: 2 sets forth an amino acid sequence encoded by SEQ ID NO: 1.

SEQ ID NO: 3 sets forth a nucleotide sequence identical to SEQ ID NO: 1 except the protein coding region spans nucleotides 3 through 509.

SEQ ID NO: 4 sets forth the amino acid sequence encoded by SEQ ID NO: 3.

SEQ ID NOS: 5–9 set forth the amino acid sequences of human IL-1 Hy1, rat IL-1Ra, pig IL-1Ra, human IL-1Ra and intracellular human IL-1Ra, respectively.

SEQ ID NO: 14 sets forth an extended cDNA sequence of a human IL-1 Hy2 clone which is longer than SEQ ID NO: 1 but encodes the same 152 amino acid polypeptide (SEQ ID NO: 2).

SEQ ID NO: 15 sets forth the genomic DNA sequence of human IL-1 Hy2.

SEQ ID NO: 12 sets forth the predicted cDNA sequence based on the human genomic sequence of IL-Hy2. (SEQ ID NO: 15) and differs from SEQ ID NO: 14 at position 279 (C→T).

SEQ ID NO: 13 sets forth the 200 amino acid sequence encoded by the longer open reading frame of SEQ ID NO: 12.

SEQ ID NO: 16 sets forth the genomic DNA sequence of murine IL-1 Hy2.

SEQ ID NO: 17 sets forth the predicted murine cDNA sequence based on the mouse genomic sequence of SEQ ID NO: 16.

SEQ ID NO: 18 sets forth the deduced amino acid sequence of murine IL-1 Hy2 polypeptide.

2. NUCLEIC ACIDS OF THE INVENTION

The isolated polynucleotides of the invention include, but are not limited to, a polynucleotide encoding a polypeptide comprising the amino acid sequence of SEQ ID NOS: 2, 4 or 13. A preferred nucleic acid sequence is set forth in SEQ ID NO: 1 (which is identical to SEQ ID NO: 3 except for the identification of the protein coding region, which is nucleotides 54 through 509 for SEQ ID NO: 1 and nucleotides 3 through 509 for SEQ ID NO: 3).

There are two alternative open reading frames in SEQ ID NO: 1. Resequencing of the 5' region of the IL-1 Hy2 cDNA resulted in SEQ ID NO: 14 which includes the shorter open reading frame of SEQ ID NO: 1 and extends its 5' sequence. The predicted amino acid sequence based upon the shorter open reading frame of SEQ ID NO: 14 is shown in SEQ ID NO: 2. The predicted cDNA sequence based on the genomic DNA sequence is set forth as SEQ ID NO: 12, which contains a C→T change that results in an alternative upstream initiating methionine which extends the open reading frame of SEQ ID NO: 3. The predicted amino acid sequence based on the longer open reading frame is shown in SEQ ID NO: 13.

The isolated polynucleotides of the invention further include, but are not limited to a polynucleotide comprising the nucleotide sequence of SEQ ID NOS: 1, 12 or 14; a polynucleotide comprising the full length protein coding sequence of SEQ ID NOS: 1, 12 or 14; and a polynucleotide comprising the nucleotide sequence of the mature protein coding sequence of SEQ ID NOS: 1, 12 or 14. The polynucleotides of the present invention also include, but are not limited to, polynucleotides that encode polypeptides with IL-1 Hy2 activity and that hybridize under stringent hybridization conditions to the complement of either (a) the nucleotide sequence of SEQ ID NOS: 1, 12 or 14, or (b) a nucleotide sequence encoding the amino acid sequence of SEQ ID NOS: 2, 4 or 13; a polynucleotide which is an allelic variant of any polynucleotide recited above; a polynucleotide which encodes a species homologue of any of the proteins recited above; or a polynucleotide that encodes a polypeptide comprising a specific domain or truncation of the polypeptide of SEQ ID NOS: 2, 4 or 13.

The polynucleotides of the present invention still further include, but are not limited to, a polynucleotide comprising the nucleotide sequence of the cDNA insert of clone pIL-1 Hy2 or an IL-1 Hy2 protein coding portion thereof, such as the full length protein coding sequence or the mature protein coding sequence.

The polynucleotides of the invention additionally include the complement of any of the polynucleotides recited above.

The polynucleotides of the invention also provide polynucleotides including nucleotide sequences that are substantially equivalent to the polynucleotides recited above. Polynucleotides according to the invention can have at least about 65%, more typically at least about 70%, 75%, 80%, 85% or 90%, and even more typically at least about 95%, sequence identity to a polynucleotide recited above. The invention also provides the complement of the polynucleotides including a nucleotide sequence that has at least about 80%, more typically at least about 90%, and even more typically at least about 95%, sequence identity to a polynucleotide encoding a polypeptide recited above. The polynucleotide can be DNA (genomic, cDNA, amplified, or synthetic) or RNA. Methods and algorithms for obtaining such polynucleotides are well known to those of skill in the art and can include, for example, methods for determining hybridization conditions which can routinely isolate polynucleotides of the desired sequence identities.

A polynucleotide according to the invention can be joined to any of a variety of other nucleotide sequences by well-established recombinant DNA techniques (see Sambrook J et al. (1989) Molecular Cloning: A Laboratory Manual, Cold Spring Harbor Laboratory, NY). Useful nucleotide sequences for joining to polypeptides include an assortment of vectors, e.g., plasmids, cosmids, lambda phage derivatives, phagemids, and the like, that are well known in the art. Accordingly, the invention also provides a vector including a polynucleotide of the invention and a host cell containing the polynucleotide. In general, the vector contains an origin of replication functional in at least one organism, convenient restriction endonuclease sites, and a selectable marker for the host cell. Vectors according to the invention include expression vectors, replication vectors, probe generation vectors, and sequencing vectors. A host cell according to the invention can be a prokaryotic or eukaryotic cell and can be a unicellular organism or part of a multicellular organism.

The sequences falling within the scope of the present invention are not limited to the specific sequences herein described, but also include allelic variations thereof. Allelic variations can be routinely determined by comparing the sequence provided in SEQ ID NOS: 1, 12 or 14, or a representative fragment thereof, or a nucleotide sequence at least 99.9% identical to SEQ ID NOS: 1, 12 or 14 with a sequence from another isolate of the same species. Example 2 shows that several allelic variants exist, some of which result in changes in the encoded polypeptide sequence.

To accommodate codon variability, the invention includes nucleic acid molecules coding for the same amino acid sequences as do the specific ORFs disclosed herein. In other words, in the coding region of an ORF, substitution of one codon for another which encodes the same amino acid is expressly contemplated. Any specific sequence disclosed herein can be readily screened for errors by resequencing a particular fragment, such as an ORF, in both directions (i.e., sequence both strands).

The present invention further provides recombinant constructs comprising a nucleic acid having the sequence of SEQ ID NOS: 1, 12 or 14; or a fragment thereof or any other polynucleotides of the invention. In one embodiment, the recombinant constructs of the present invention comprise a vector, such as a plasmid or viral vector, into which a nucleic acid having the sequence of SEQ ID NOS: 1, 12 or 14; or a fragment thereof is inserted, in a forward or reverse orientation. In the case of a vector comprising one of the ORFs of the present invention, the vector may further comprise regulatory sequences, including for example, a promoter, operably linked to the ORF. For vectors comprising the EMFs and UMFs of the present invention, the vector may further comprise a marker sequence or heterologous ORF operably linked to the EMF or UMF. Large numbers of suitable vectors and promoters are known to those of skill in the art and are commercially available for generating the recombinant constructs of the present invention. The following vectors are provided by way of example. Bacterial: pBs, phagescript, PsiX174, pBluescript SK, pBs KS, pNH8a, pNH16a, pNH18a, pNH46a (Stratagene); pTrc99A, pKK223-3, pKK233-3, pDR540, pRIT5 (Pharmacia). Eukaryotic: pWLneo, pSV2cat, pOG44, PXTI, pSG (Stratagene) pSVK3, pBPV, pMSG, pSVL (Pharmacia).

The isolated polynucleotide of the invention may be operably linked to an expression control sequence such as the pMT2 or pED expression vectors disclosed in Kaufman et al., Nucleic Acids Res. 19, 4485–4490 (1991), in order to produce the protein recombinantly. Many suitable expression control sequences are known in the art. General methods of expressing recombinant proteins are also known and are exemplified in R. Kaufman, Methods in Enzymology 185, 537–566 (1990). As defined herein "operably linked" means that the isolated polynucleotide of the invention and an expression control sequence are situated within a vector or cell in such a way that the protein is expressed by a host cell which has been transformed (transfected) with the ligated polynucleotide/expression control sequence.

Promoter regions can be selected from any desired gene using CAT (chloramphenicol transferase) vectors or other vectors with selectable markers. Two appropriate vectors are pKK232-8 and pCM7. Particular named bacterial promoters include lac, lacZ, T3, T7, gpt, lambda PR, and trc. Eukaryotic promoters include CMV immediate early, HSV thymidine kinase, early and late SV40, LTRs from retrovirus, and mouse metallothionein-1. Selection of the appropriate vector and promoter is well within the level of ordinary skill in the art. Generally, recombinant expression vectors will include origins of replication and selectable markers permitting transformation of the host cell, e.g., the ampicillin resistance gene of E. coli and S. cerevisiae TRP1 gene, and a promoter derived from a highly-expressed gene to direct transcription of a downstream structural sequence. Such promoters can be derived from operons encoding glycolytic enzymes such as 3-phosphoglycerate kinase (PGK), a-factor, acid phosphatase, or heat shock proteins, among others. The heterologous structural sequence is assembled in appropriate phase with translation initiation and termination sequences, and preferably, a leader sequence capable of directing secretion of translated protein into the periplasmic space or extracellular medium. Optionally, the heterologous sequence can encode a fusion protein including an N-terminal identification peptide imparting desired characteristics, e.g., stabilization or simplified purification of expressed recombinant product. Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and to, if desirable, provide amplification within the host. Suitable prokaryotic hosts for transformation include E. coli, Bacillus subtilis, Salmonella typhimurium and various species within the genera Pseudomonas, Streptomyces, and Staphylococcus, although others may also be employed as a matter of choice.

As a representative but non-limiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and GEM 1 (Promega Biotec, Madison, Wis., USA). These pBR322 "backbone" sections are combined with an appropriate promoter and the structural sequence to be expressed. Following transformation of a suitable host strain and growth of the host strain to an appropriate cell density, the selected promoter is induced or derepressed by appropriate means (e.g., temperature shift or chemical induction) and cells are cultured for an additional period. Cells are typically harvested by centrifugation, disrupted by physical or chemical means, and the resulting crude extract retained for further purification.

Included within the scope of the nucleic acid sequences of the invention are nucleic acid sequences that hybridize under stringent conditions to a fragment of the DNA sequence of SEQ ID NOS: 1, 12 or 14, which fragment is greater than about 10 bp, preferably 20–50 bp, and even greater than 100 bp. In accordance with the invention, polynucleotide sequences which encode the novel nucleic acids, or functional equivalents thereof, may be used to generate recombinant DNA molecules that direct the expression of that nucleic acid, or a functional equivalent thereof, in appropriate host cells.

The nucleic acid sequences of the invention are further directed to sequences which encode variants of the described nucleic acids. These amino acid sequence variants may be prepared by methods known in the art by introducing appropriate nucleotide changes into a native or variant polynucleotide. There are two variables in the construction of amino acid sequence variants: the location of the mutation and the nature of the mutation. The amino acid sequence variants of the nucleic acids are preferably constructed by mutating the polynucleotide to give an amino acid sequence that does not occur in nature. These amino acid alterations can be made at sites that differ in the nucleic acids from different species (variable positions) or in highly conserved regions (constant regions). Sites at such locations will typically be modified in series, e.g., by substituting first with conservative choices (e.g., hydrophobic amino acid to a different hydrophobic amino acid) and then with more distant choices (e.g., hydrophobic amino acid to a charged amino acid), and then deletions or insertions may be made at the target site. Amino acid sequence deletions generally range from about 1 to 30 residues, preferably about 1 to 10 residues, and are typically contiguous. Amino acid insertions include amino- and/or carboxyl-terminal fusions ranging in length from one to one hundred or more residues, as well as intrasequence insertions of single or multiple amino acid residues. Intrasequence insertions may range generally from about 1 to 10 amino residues, preferably from 1 to 5 residues. Examples of terminal insertions include the heterologous signal sequences necessary for secretion or for intracellular targeting in different host cells.

In a preferred method, polynucleotides encoding the novel nucleic acids are changed via site-directed mutagenesis. This method uses oligonucleotide sequences that encode the polynucleotide sequence of the desired amino acid variant, as well as a sufficient adjacent nucleotide on both sides of the changed amino acid to form a stable duplex on either side of the site of being changed. In general, the techniques of site-directed mutagenesis are well known to those of skill in the art and this technique is exemplified by publications such as, Edelman et al., DNA 2:183 (1983). A versatile and efficient method for producing site-specific changes in a polynucleotide sequence was published by Zoller and Smith, Nucleic Acids Res. 10:6487–6500 (1982). PCR may also be used to create amino acid sequence variants of the novel nucleic acids. When small amounts of template DNA are used as starting material, primer(s) that differs slightly in sequence from the corresponding region in the template DNA can generate the desired amino acid variant. PCR amplification results in a population of product DNA fragments that differ from the polynucleotide template encoding the polypeptide at the position specified by the primer. The product DNA fragments replace the corresponding region in the plasmid and this gives the desired amino acid variant.

A further technique for generating amino acid variants is the cassette mutagenesis technique described in Wells et al., Gene 34:315 (1985); and other mutagenesis techniques well known in the art, such as, for example, the techniques in Sambrook et al., supra, and Current Protocols in Molecular Biology, Ausubel et al. Due to the inherent degeneracy of the genetic code, other DNA sequences which encode substantially the same or a functionally equivalent amino acid sequence may be used in the practice of the invention for the cloning and expression of these novel nucleic acids. Such DNA sequences include those which are capable of hybridizing to the appropriate novel nucleic acid sequence under stringent conditions.

Furthermore, knowledge of the DNA sequence provided by the present invention allows for the modification of cells to permit, or increase, expression of endogenous IL-1 Hy2 polypeptides. Cells can be modified (e.g., by homologous recombination) to provide increased IL-1 Hy2 expression by replacing, in whole or in part, the naturally occurring IL-1 Hy2 promoter with all or part of a heterologous promoter so that the cells express IL-1 Hy2 polypeptides at a higher level. The heterologous promoter is inserted in such a manner that it is operatively linked to IL-1 Hy2 encoding sequences. See, for example, PCT International Publication No. WO94/12650, PCT International Publication No. WO92/20808, and PCT International Publication No. WO91/09955. It is also contemplated that, in addition to heterologous promoter DNA, amplifiable marker DNA (e.g., ada, dhfr, and the multifunctional CAD gene which encodes carbamyl phosphate synthase, aspartate transcarbamylase, and dihydroorotase) and/or intron DNA may be inserted along with the heterologous promoter DNA. If linked to the IL-1 Hy2 coding sequence, amplification of the marker DNA by standard selection methods results in co-amplification of the IL-1 Hy2 coding sequences in the cells.

The polynucleotides of the present invention also make possible the development, through, e.g., homologous recombination or knock out strategies, of animals that fail to express functional IL-1 Hy2 polypeptides or that express a variant of a IL-1 Hy2 polypeptide. Such animals are useful as models for studying the in vivo activities of IL-1 Hy2 polypeptides as well as for studying modulators of IL-1 Hy2 polypeptides.

Polynucleotides of the invention can also be used to induce immune responses. For example, as described in Fan et al., Nat. Biotech. 17:870–872 (1999), incorporated herein by reference, nucleic acid sequences encoding a polypeptide may be used to generate antibodies against the encoded polypeptide following topical administration of naked plasmid DNA or following injection, and preferably intramuscular injection of the DNA. The nucleic acid sequences are preferably inserted in a recombinant expression vector and may be in the form of naked DNA.

3. HOSTS

The present invention further provides host cells genetically engineered to contain the polynucleotides of the invention. For example, such host cells may contain nucleic acids of the invention introduced into the host cell using known transformation, transfection or infection methods. The present invention still further provides host cells genetically engineered to express the polynucleotides of the invention, wherein such polynucleotides are in operative association with a regulatory sequence heterologous to the host cell which drives expression of the polynucleotides in the cell.

The host cell can be a higher eukaryotic host cell, such as a mammalian cell, a lower eukaryotic host cell, such as a yeast cell, or the host cell can be a prokaryotic cell, such as a bacterial cell. Introduction of the recombinant construct into the host cell can be effected by calcium phosphate transfection, DEAE, dextran mediated transfer, such as a yeast cell, or the host cell can be a prokaryotic cell, such as a bacterial cell. Introduction of the recombinant construct into the host cell can be effected by calcium phosphate transfection, DEAE, dextran mediated transfection, or electroporation (Davis, L. et al., Basic Methods in Molecular Biology (1986)). The host cells containing one of polynucleotides of the invention, can be used in conventional manners to produce the gene product encoded by the isolated fragment (in the case of an ORF) or can be used to produce a heterologous protein under the control of the EMF.

Any host/vector system can be used to express one or more of the ORFs of the present invention. These include, but are not limited to, eukaryotic hosts such as HeLa cells, Cv-1 cell, COS cells, and Sf9 cells, as well as prokaryotic host such as E. coli and B. subtilis. The most preferred cells are those which do not normally express the particular polypeptide or protein or which expresses the polypeptide or protein at low natural level. Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook, et al., in Molecular Cloning: A Laboratory Manual, Second Edition, Cold Spring Harbor, N.Y. (1989), the disclosure of which is hereby incorporated by reference.

Various mammalian cell culture systems can also be employed to express recombinant protein. Examples of mammalian expression systems include the COS-7 lines of monkey kidney fibroblasts, described by Gluzman, Cell 23:175 (1981), and other cell lines capable of expressing a compatible vector, for example, the C127, 3T3, CHO, HeLa and BHK cell tines. Mammalian expression vectors will comprise an origin of replication, a suitable promoter and also any necessary ribosome binding sites, polyadenylation site, splice donor and acceptor sites, transcriptional termination sequences, and 5' flanking nontranscribed sequences. DNA sequences derived from the SV40 viral genome, for example, SV40 origin, early promoter, enhancer, splice, and polyadenylation sites may be used to provide the required nontranscribed genetic elements. Recombinant polypeptides and proteins produced in bacterial culture are usually isolated by initial extraction from cell pellets, followed by one or more salting-out, aqueous ion exchange or size exclusion chromatography steps. Protein refolding steps can be used, as necessary, in completing configuration of the mature protein. Finally, high performance liquid chromatography (HPLC) can be employed for final purification steps. Microbial cells employed in expression of proteins can be disrupted by any convenient method, including freeze-thaw cycling, sonication, mechanical disruption, or use of cell lysing agents.

A number of types of cells may act as suitable host cells for expression of the protein. Mammalian host cells include, for example, monkey COS cells, Chinese Hamster Ovary (CHO) cells, human kidney 293 cells, human epidermal A431 cells, human Colo205 cells, 3T3 cells, CV-1 cells, other transformed primate cell lines, normal diploid cells, cell strains derived from in vitro culture of primary tissue, primary explants, HeLa cells, mouse L cells, BHK, HL-60, U937, HaK or Jurkat cells.

Alternatively, it may be possible to produce the protein in lower eukaryotes such as yeast or in prokaryotes such as bacteria. Potentially suitable yeast strains include *Saccharomyces cerevisiae, Schizosaccharomyces pombe,* Kluyveromyces strains, Candida, or any yeast strain capable of expressing heterologous proteins. Potentially suitable bacterial strains include *Escherichia coli, Bacillus subtilis, Salmonella typhimurium,* or any bacterial strain capable of expressing heterologous proteins. If the protein is made in yeast or bacteria, it may be necessary to modify the protein produced therein, for example by phosphorylation or glycosylation of the appropriate sites, in order to obtain the functional protein. Such covalent attachments may be accomplished using known chemical or enzymatic methods.

In another embodiment of the present invention, cells and tissues may be engineered to express an endogenous gene comprising the polynucleotides of the invention under the control of inducible regulatory elements, in which case the regulatory sequences of the endogenous gene may be replaced by homologous recombination. As described herein, gene targeting can be used to replace a gene's existing regulatory region with a regulatory sequence isolated from a different gene or a novel regulatory sequence synthesized by genetic engineering methods. Such regulatory sequences may be comprised of promoters, enhancers, scaffold-attachment regions, negative regulatory elements, transcriptional initiation sites, regulatory protein binding sites or combinations of said sequences. Alternatively, sequences which affect the structure or stability of the RNA or protein produced may be replaced, removed, added, or otherwise modified by targeting, including polyadenylation signals. mRNA stability elements, splice sites, leader sequences for enhancing or modifying transport or secretion properties of the protein, or other sequences which alter or improve the function or stability of protein or RNA molecules.

The targeting event may be a simple insertion of the regulatory sequence, placing the gene under the control of the new regulatory sequence, e.g., inserting a new promoter or enhancer or both upstream of a gene. Alternatively, the targeting event may be a simple deletion of a regulatory element, such as the deletion of a tissue-specific negative regulatory element. Alternatively, the targeting event may replace an existing element; for example, a tissue-specific enhancer can be replaced by an enhancer that has broader or different cell-type specificity than the naturally occurring elements. Here, the naturally occurring sequences are deleted and new sequences are added. In all cases, the identification of the targeting event may be facilitated by the use of one or more selectable marker genes that are contiguous with the targeting DNA, allowing for the selection of cells in which the exogenous DNA has integrated into the host cell genome. The identification of the targeting event may also be facilitated by the use of one or more marker genes exhibiting the property of negative selection, such that the negatively selectable marker is linked to the exogenous DNA, but configured such that the negatively selectable marker flanks the targeting sequence, and such that a correct homologous recombination event with sequences in the host cell genome does not result in the stable integration of the negatively selectable marker. Markers useful for this purpose include the Herpes Simplex Virus thymidine kinase (TK) gene or the bacterial xanthine-guanine phosphoribosyl-transferase (gpt) gene.

The gene targeting or gene activation techniques which can be used in accordance with this aspect of the invention are more particularly described in U.S. Pat. No. 5,272,071 to Chappel; U.S. Pat. No. 5,578,461 to Sherwin et al.; International Application No. PCT/US92/09627 (WO93/09222) by Selden et al.; and International Application No. PCT/US90/06436 (WO91/06667) by Skoultchi et al., each of which is incorporated by reference herein in its entirety.

4. POLYPEPTIDES OF THE INVENTION

SEQ ID NO. 1 encodes the IL-1 Hy2 polypeptide sequence of SEQ ID NOS: 2, 4 and 13. An amino acid alignment of SEQ ID NO. 2 with human secreted IL-1Ra, human intracellular IL-1Ra and human IL-1 Hy1, as well as rat and pig IL-1Ra, is shown in FIG. 1. SEQ ID NO. 2 displays significant amino acid homology with human IL-1Ra and IL-1 Hy1 (41.4% and 45% sequence identity, respectively, using the Jotan Hein method), and thus represents a novel molecule within the IL-1Ra family. The sequence similarities among the three proteins and the localization of the IL-1 Hy2 gene to chromosome 2, where other proteins of the IL-1 system are located, indicate that IL-1 Hy2 is involved in the IL-1 system and may play some common biological roles as IL-1Ra and IL-1 Hy1, e.g., acting as an IL-1 antagonist. Additional IL-1 Hy2 family members can be identified using SEQ ID NOS: 1, 12 or 14 as a molecular probe.

Interleukin-1 has pleiotropic biological activities many of which adversely affect the organism, it would be expected that the molecule must be tightly regulated if it is not to be injurious. Indeed, there are several reports of Interleukin-1 inhibitors that regulate the action of Interleukin-1. Interleukin-1 inhibitory activity has been reported in monocyte conditioned medium, wherein the monocytes are grown on adherent immune complexes. Arena, W. P., et al., 1985, Journal of Immun., 134:3868. Additionally, an inhibitor has been reported to be present urine. Seckinger, P., et al., 1987, Journal of Immun., 139:1546. Lastly, a protein inhibitor, purified and cloned, that has interleukin-1 receptor antagonist activity has been reported. Hannum, et at., 1990, Nature, 343:336, and Eisenberg, S., et al., 1990, Nature, 343:341.

It is thought that the Interleukin-1 inhibitor present in urine, and which has been partially purified and characterized by Seckinger, P. et al., and Seckinger, P., et al., 1987, Journal of Immun., 139:1541 is similar, if not identical to the cloned Interleukin-1 receptor antagonist reported by Eisenberg, S., et al. (1990), Nature, 343:341; and Carter, D., et al (1990), Nature, 344:633.

Interleukin-1 receptor antagonist is a naturally occurring peptide secreted by macrophages in response to many of the same stimuli which cause the secretion of lnterleukin-1 itself. Interleukin-1 receptor antagonist is a naturally occurring antagonist to the cytokines and recognizes receptors on various cell types and blocks Interleukin-1 mediated responses by occupying the receptor. (Wakabayashi et al., FASEB J 1991 ;5:338; Okusawa et al. J Clin Invest 1988;81:1162; Ohlsson et al., Nature 1990;348:550; Aiura, et al. Cytokine 1991;4:498; Fischer et al. Am J Physiol 1991;261:R442). In humans, Interleukin-1 receptor antagonist is a naturally occurring group of molecules; three forms have been characterized (two glycosylated and one non-glycosylated).

Fischer et al. (Am J Physiol 1991;261:R442) demonstrated that the administration of a naturally occurring antagonist to Interleukin-1 will significantly blunt the cytokine cascade and improve survival in baboons given a lethal dose of live bacteria. Interleukin-1 receptor antagonist significantly attenuates the decrease in mean arterial pressure and cardiac output and improves survival for severe acute pancreatitis. (U.S. Pat. No. 5,508,262) The systemic Interleukin-1 response observed as a result of bacterial sepsis was also diminished significantly, correlating with a decrease in the systemic response to bacterial sepsis.

Studies by Aiura et al. (Cytokine 1991;4:498) have shown that Interleukin-1 receptor antagonist is protective in a rabbit model of hypotensive gram-positive septic shock. The administration of Interleukin-1 receptor antagonist in this animal model has been shown to maintain mean arterial pressure compared to control, as well as decreasing lung water and maintaining urine output. This work demonstrated the role of Interleukin-1 and the protective role of Interleukin-1 receptor antagonist in gram-positive septic shock. Interleukin-1 is the principal mediator in a patient's clinical response to multiple different stresses regardless of the etiology (including acute pancreatitis, sepsis, endotoxin shock, and cytokine induced shock).

The isolated polypeptides of the invention include, but are not limited to, a polypeptide comprising the amino acid sequence of SEQ ID NOS: 2, 4, or 13, or the amino acid sequence encoded by the cDNA insert of clone pIL-1 Hy2, or a portion thereof corresponding to the full length or mature protein. Polypeptides of the invention also include polypeptides with IL-1 Hy2 activity that are encoded by (a) the polynucleotide of SEQ ID NOS: 1, 12 or 14, or (b) polynucleotides encoding SEQ ID NOS: 2, 4, or 13 (b) polynucleotides that hybridize to the complement of the polynucleotides of either (a) or (b) under stringent hybridization conditions. Biologically active or immunologically active variants of the IL-1Ra protein sequence of SEQ ID NOS: 2, 4 or 13 and "substantial equivalents" thereof (e.g., with 65%, 70%, 75%, 80%, 85%, 90%, typically 95%, more typically 98% or most typically 99% amino acid identity) that retain IL-1 Hy2 activity, preferably IL-1 antagonist activity, are also contemplated. Polypeptides encoded by allelic variants, such as those described in Example 2 below, may have a similar or increased or decreased activity compared to the polypeptides of SEQ ID NOS: 2, 4 or 13.

Protein compositions of the present invention may further comprise an acceptable carrier, such as a hydrophilic, e.g., pharmaceutically acceptable, carrier.

The invention also relates to methods for producing a polypeptide comprising growing a culture of the cells of the invention in a suitable culture medium, and purifying the protein from the culture. For example, the methods of the invention include a process for producing a polypeptide in which a host cell containing a suitable expression vector that includes a polynucleotide of the invention is cultured under conditions that allow expression of the encoded polypeptide. The polypeptide can be recovered from the culture, conveniently from the culture medium, and further purified. Preferred embodiments include those in which the protein produced by such process is a full length or mature form of the protein.

The present invention further provides isolated polypeptides encoded by the nucleic acid fragments of the present invention or by degenerate variants of the nucleic acid fragments of the present invention. By "degenerate variant" is intended nucleotide fragments which differ from a nucleic acid fragment of the present invention (e.g., an ORF) by nucleotide sequence but, due to the degeneracy of the genetic code, encode an identical polypeptide sequence. Preferred nucleic acid fragments of the present invention are the ORFs that encode proteins. A variety of methodologies known in the art can be utilized to obtain any one of the isolated polypeptides or proteins of the present invention. At the simplest level, the amino acid sequence can be synthesized using commercially available peptide synthesizers. This is particularly useful in producing small peptides and fragments of larger polypeptides. Fragments are useful, for example, in generating antibodies against the native polypeptide. In an alternative method, the polypeptide or protein is purified from bacterial cells which naturally produce the polypeptide or protein. One skilled in the art can readily follow known methods for isolating polypeptides and proteins in order to obtain one of the isolated polypeptides or proteins of the present invention. These include, but are not limited to, immunochromatography, HPLC, size-exclusion chromatography, ion-exchange chromatography, and immuno-affinity chromatography. See, e.g., Scopes, Protein Purification: Principles and Practice, Springer-Verlag (1994); Sambrook, et al., in Molecular Cloning: A Laboratory Manual; Ausubel et al., Current Protocols in Molecular Biology.

The polypeptides and proteins of the present invention can alternatively be purified from cells which have been altered to express the desired polypeptide or protein. As used herein, a cell is said to be altered to express a desired polypeptide or protein when the cell, through genetic manipulation, is made to produce a polypeptide or protein which it normally does not produce or which the cell normally produces at a lower level. One skilled in the art can readily adapt procedures for introducing and expressing either recombinant or synthetic sequences into eukaryotic or prokaryotic cells in order to generate a cell which produces one of the polypeptides or proteins of the present invention. The purified polypeptides can be used in in vitro binding assays which are well known in the art to identify molecules which bind to the polypeptides. These molecules include but are not limited to, for e.g., small molecules, molecules from combinatorial libraries, antibodies or other proteins. The molecules identified in the binding assay are then tested for antagonist or agonist activity in in vivo tissue culture or animal models that are well known in the art. In brief, the molecules are titrated into a plurality of cell cultures or animals and then tested for either cell/animal death or prolonged survival of the animal/cells.

In addition, the binding molecules may be complexed with toxins, e.g., ricin or cholera, or with other compounds that are toxic to cells. The toxin-binding molecule complex is then targeted to a tumor or other cell by the specificity of the binding molecule for SEQ ID NOS: 2, 4 or 13.

The protein of the invention may also be expressed as a product of transgenic animals, e.g., as a component of the milk of transgenic cows, goats, pigs, or sheep which are characterized by somatic or germ cells containing a nucleotide sequence encoding the protein.

The protein may also be produced by known conventional chemical synthesis. Methods for constructing the proteins of the present invention by synthetic means are known to those skilled in the art. The synthetically-constructed protein sequences, by virtue of sharing primary, secondary or tertiary structural and/or conformational characteristics with proteins may possess biological properties in common therewith, including protein activity. Thus, they may be employed as biologically active or immunological substitutes for natural, purified proteins in screening of therapeutic compounds and in immunological processes for the development of antibodies.

The proteins provided herein also include proteins characterized by amino acid sequences similar to those of purified proteins but into which modification are naturally provided or deliberately engineered. For example, modifications in the peptide or DNA sequences can be made by those skilled in the art using known techniques. Modifications of interest in the protein sequences may include the alteration, substitution, replacement, insertion or deletion of a selected amino acid residue in the coding sequence. For example, one or more of the cysteine residues may be deleted or replaced with another amino acid to alter the conformation of the molecule. Techniques for such alteration, substitution, replacement, insertion or deletion are well known to those skilled in the art (see, e.g., U.S. Pat. No. 4,518,584). Preferably, such alteration, substitution, replacement, insertion or deletion retains the desired activity of the protein.

Other fragments and derivatives of the sequences of proteins which would be expected to retain protein activity in whole or in part and may thus be useful for screening or other immunological methodologies may also be easily made by those skilled in the art given the disclosures herein. Such modifications are believed to be encompassed by the present invention.

The protein may also be produced by operably linking the isolated polynucleotide of the invention to suitable control sequences in one or more insect expression vectors, and employing an insect expression system. Materials and methods for baculovirus/insect cell expression systems are commercially available in kit form from, e.g., Invitrogen, San Diego, Calif., U.S.A. (the MAXBAT™ kit), and such methods are well known in the art, as described in Summers and Smith, Texas Agricultural Experiment Station Bulletin No. 1555 (1987), incorporated herein by reference. As used herein, an insect cell capable of expressing a polynucleotide of the present invention is "transformed."

The protein of the invention may be prepared by culturing transformed host cells under culture conditions suitable to express the recombinant protein. The resulting expressed protein may then be purified from such culture (i.e., from culture medium or cell extracts) using known purification processes, such as gel filtration and ion exchange chromatography. The purification of the protein may also include an affinity column containing agents which will bind to the protein; one or more column steps over such affinity resins as concanavalin A-agarose, HEPARIN-TOYOPEARL™, or CIBACROM BLUE 3GA SEPHAROSE™; one or more steps involving hydrophobic interaction chromatography using such resins as phenyl ether, butyl ether, or propyl ether; or immunoaffinity chromatography.

Alternatively, the protein of the invention may also be expressed in a form which will facilitate purification. For example, it may be expressed as a fusion protein, such as those of maltose binding protein (MBP), glutathione-S-transferase (GST) or thioredoxin (TRX). Kits for expression and purification of such fusion proteins are commercially available from New England BioLab (Beverly, Mass.), Pharmacia (Piscataway, N.J.) and In Vitrogen, respectively. The protein can also be tagged with an epitope and subsequently purified by using a specific antibody directed to such epitope. One such epitope ("Flag") is commercially available from Kodak (New Haven, Conn.).

Finally, one or more reverse-phase high performance liquid chromatography (RP-HPLC) steps employing hydrophobic RP-HPLC media, e.g., silica gel having pendant methyl or other aliphatic groups, can be employed to further purify the protein. Some or all of the foregoing purification steps, in various combinations, can also be employed to provide a substantially homogeneous isolated recombinant protein. The protein thus purified is substantially free of other mammalian proteins and is defined in accordance with the present invention as an "isolated protein."

The polypeptides of the invention include Interleukin-1 Hy2 analogs or variants. This embraces fragments of IL-1 Hy2 of the invention, as well as analogs (variants) of IL-1 Hy2 in which one or more amino acids has been deleted, inserted, or substituted. Analogs of the invention also embrace fusions or modifications of IL-1 Hy2 wherein the IL-1 Hy2 or analog is fused to another moiety or moieties, e.g., targeting moiety or another therapeutic agent. Such analogs may exhibit improved properties such as activity and/or stability. Examples of moieties which may be fused to IL-1 Hy2 or an analog include, for example, targeting moieties which provide for the delivery of polypeptide to pancreatic cells, e.g., antibodies to pancreatic cells, antibodies to immune cells such as T-cells, monocytes, dendritic cells, granulocytes, etc., as well as receptor and ligands expressed on pancreatic or immune cells. Other moieties which may be fused to IL-1 Hy2 or an analog include therapeutic agents which are used for treatment, for example, immunosuppressive drugs such as cyclosporin, SK506, azathioprine, CD3 antibodies and steroids, or immunostimulants, immune modulators, and other cytokines such as alpha or beta interferon.

5. DEPOSIT OF CLONE

The following clone, pIL-1 Hy2 was deposited with the American Type Culture Collection (ATCC) 10801 University Avenue, Manassas, Va., on May 21, 1999 under the terms of the Budapest Treaty. The clone represents a plasmid clone as described in the Examples set forth below.

| Microorganism/Clone | ATCC Accession No. |
| --- | --- |
| pIL-lHy2 | PTA-96 |

6. USES AND BIOLOGICAL ACTIVITY

The polynucleotides and proteins of the present invention are expected to exhibit one or more of the uses or biological activities (including those associated with assays cited herein) identified below. Uses or activities described for proteins of the present invention may be provided by administration or use of such proteins or by administration or use of polynucleotides encoding such proteins (such as, for example, in gene therapies or vectors suitable for introduction of DNA).

6.1. Research Uses and Utilities

The polynucleotides provided by the present invention can be used by the research community for various purposes. The polynucleotides can be used to express recombinant protein for analysis, characterization or therapeutic use; as markers for tissues in which the corresponding protein is preferentially expressed (either constitutively or at a particular stage of tissue differentiation or development or in disease states); as molecular weight markers on Southern gels; as chromosome markers or tags (when labeled) to identify chromosomes or to map related gene positions; to compare with endogenous DNA sequences in patients to identify potential genetic disorders; as probes to hybridize and thus discover novel, related DNA sequences; as a source of information to derive PCR primers for genetic fingerprinting; as a probe to "subtract-out" known sequences in the process of discovering other novel polynucleotides; for selecting and making oligomers for attachment to a "gene chip" or other support, including for examination of expression patterns; to raise anti-protein antibodies using DNA immunization techniques; and as an antigen to raise anti-DNA antibodies or elicit another immune response. Where the polynucleotide encodes a protein which binds or potentially binds to another protein (such as, for example, in a receptor-ligand interaction), the polynucleotide can also be used in interaction trap assays (such as, for example, that described in Gyuris et al., Cell 75:791–803 (1993)) to identify polynucleotides encoding the other protein with which binding occurs or to identify inhibitors of the binding interaction.

The proteins provided by the present invention can similarly be used in assay to determine biological activity, including in a panel of multiple proteins for high-throughput screening; to raise antibodies or to elicit another immune response; as a reagent (including the labeled reagent) in assays designed to quantitatively determine levels of the protein (or its receptor) in biological fluids; as markers for tissues in which the corresponding protein is preferentially expressed (either constitutively or at a particular stage of tissue differentiation or development or in a disease state); and, of course, to isolate correlative receptors or ligands. Where the protein binds or potentially binds to another protein (such as, for example, in a receptor-ligand interaction), the protein can be used to identify the other protein with which binding occurs or to identify inhibitors of the binding interaction. Proteins involved in these binding interactions can also be used to screen for peptide or small molecule inhibitors or agonists of the binding interaction.

Any or all of these research utilities are capable of being developed into reagent grade or kit format for commercialization as research products.

Methods for performing the uses listed above are well known to those skilled in the art. References disclosing such methods include without limitation "Molecular Cloning: A Laboratory Manual", 2d ed., Cold Spring Harbor Laboratory Press, Sambrook, J., E. F. Fritsch and T. Maniatis eds., 1989, and "Methods in Enzymology: Guide to Molecular Cloning Techniques", Academic Press, Berger, S. L. and A. R. Kimmel eds., 1987.

6.2. Nutritional Uses

Polynucleotides and proteins of the present invention can also be used as nutritional sources or supplements. Such uses include without limitation use as a protein or amino acid supplement, use as a carbon source, use as a nitrogen source and use as a source of carbohydrate. In such cases the protein or polynucleotide of the invention can be added to the feed of a particular organism or can be administered as a separate solid or liquid preparation, such as in the form of powder, pills, solutions, suspensions or capsules. In the case of microorganisms, the protein or polynucleotide of the invention can be added to the medium in or on which the microorganism is cultured.

6.3. Cytokine and Cell Proliferation/Differentiation Activity

A protein of the present invention may exhibit cytokine, cell proliferation (either inducing or inhibiting) or cell differentiation (either inducing or inhibiting) activity or may induce production of other cytokines in certain cell populations. A polynucleotide of the invention can encode a polypeptide exhibiting such attributes. Many protein factors discovered to date, including all known cytokines, have exhibited activity in one or more factor-dependent cell proliferation assays, and hence the assays serve as a convenient confirmation of cytokine activity. The activity of a protein of the present invention is evidenced by any one of a number of routine factor dependent cell proliferation assays for cell lines including, without limitation, 32D, DA2, DA1G, T10, B9, B9/11, BaF3, MC9/G, M+(preB M+), 2E8, RB5, DA1, 123, T1165, HT2, CTLL2, TF-1, Mo7e and CMK. The activity of a protein of the invention may, among other means, be measured by the following methods:

Assays for T-cell or thymocyte proliferation include without limitation those described in: Current Protocols in Immunology, Ed by J. E. Coligan, A. M. Kruisbeek, D. H. Margulies, E. M. Shevach, W. Strober, Pub. Greene Publishing Associates and Wiley-Interscience (Chapter 3, In Vitro assays for Mouse Lymphocyte Function 3.1–3.19; Chapter 7, Immunologic studies in Humans); Takai et al., J. Immunol. 137:3494–3500, 1986; Bertagnolli et al., J. Immunol. 145:1706–1712, 1990; Bertagnolli et al., Cellular Immunology 133:327–341, 1991; Bertagnolli, et al., I. Immunol. 149:3778–3783, 1992; Bowman et al., I. Immunol. 152:1756–1761, 1994.

Assays for cytokine production and/or proliferation of spleen cells, lymph node cells or thymocytes include, without limitation, those described in: Polyclonal T cell stimulation, Kruisbeek, A. M. and Shevach, E. M. In Current Protocols in Immunology. J. E. e.a. Coligan eds. Vol 1 pp. 3.12.1–3.12.14, John Wiley and Sons, Toronto. 1994; and Measurement of mouse and human interleukin gamma., Schreiber, R. D. In Current Protocols in Immunology. J. E. e.a. Coligan eds. Vol 1 pp. 6.8.1–6.8.8, John Wiley and Sons, Toronto. 1994.

Assays for proliferation and differentiation of hematopoietic and lymphopoietic cells include, without limitation, those described in: Measurement of Human and Murine Interleukin 2 and Interleukin 4, Bottomly, K., Davis, L. S. and Lipsky, P. E. In Current Protocols in Immunology. J. E. e.a. Coligan eds. Vol 1 pp. 6.3.1–6.3.12, John Wiley and Sons, Toronto. 1991; deVries et al., J. Exp. Med. 173:1205–1211, 1991; Moreau et al., Nature 336:690–692, 1988; Greenberger et al., Proc. Natl. Acad. Sci. U.S.A. 80:2931–2938, 1983; Measurement of mouse and human interleukin 6—Nordan, R. In Current Protocols in Immunology. J. E. e.a. Coligan eds. Vol 1 pp. 6.6.1–6.6.5, John Wiley and Sons, Toronto. 1991; Smith et al., Proc. Natl. Aced. Sci. U.S.A. 83:1857–1861, 1986; Measurement of human Interleukin 11—Bennett, F., Giannotti, J., Clark, S. C. and Turner, K. J. In Current Protocols in Immunology. J. E. e.a. Coligan eds. Vol 1 pp. 6.15.1 John Wiley and Sons, Toronto. 1991; Measurement of mouse and human Interleukin 9—Ciarletta, A., Giannotti, J., Clark, S. C. and Turner, K. J. In Current Protocols in Immunology. J. E. e.a. Coligan eds. Vol 1 pp. 6.13.1, John Wiley and Sons, Toronto. 1991.

Assays for T-cell clone responses to antigens (which will identify, among others, proteins that affect APC-T cell interactions as well as direct T-cell effects by measuring proliferation and cytokine production) include, without limitation, those described in: Current Protocols in Immunology, Ed by J. E. Coligan, A. M. Kruisbeek, D. H. Margulies, E. M. Shevach, W Strober, Pub. Greene Publishing Associates and Wiley-Interscience (Chapter 3, In Vitro assays for Mouse Lymphocyte Function; Chapter 6, Cytokines and their cellular receptors; Chapter 7, Immunologic studies in Humans); Weinberger et al., Proc. Natl. Acad. Sci. USA 77:6091–6095, 1980; Weinberger et al., Eur. J. Immun. 11:405–411, 1981; Takai et al., J. Immunol. 137:3494–3500, 1986; Takai et al., J. Immunol. 140:508–512, 1988.

6.4. Immune Stimulating or Suppressing Activity

A protein of the present invention may also exhibit immune stimulating or immune suppressing activity, including without limitation the activities for which assays are described herein. A polynucleotide of the invention can encode a polypeptide exhibiting such activities. A protein may be useful in the treatment of various immune deficiencies and disorders (including severe combined immunodeficiency (SCID)), e.g., in regulating (up or down) growth and proliferation of T and/or B lymphocytes, as well as effecting the cytolytic activity of NK cells and other cell populations. These immune deficiencies may be genetic or be caused by viral (e.g., HIV) as well as bacterial or fungal infections, or may result from autoimmune disorders. More specifically, infectious diseases causes by viral, bacterial, fungal or other infection may be treatable using a protein of the present invention, including infections by HIV, hepatitis viruses, herpesviruses, mycobacteria, Leishmania spp., malaria spp. and various fungal infections such as candidiasis. Of course, in this regard, a protein of the present invention may also be useful where a boost to the immune system generally may be desirable, i.e., in the treatment of cancer. IL-1 has been indicated to promote tumor cell growth in cancers of various organs including breast adenocarcinoma, brain tumors, melanoma, myeloma, giant cell tumors of bone, acute myelogenous leukemia, oral epidermoid carcinoma, and squamous cell carcinoma; thus treatment of such cancer disease states involving elevated levels of IL-1 with IL-1 Hy2 polypeptides of the present invention is expected to ameliorate signs and symptoms of cancer.

Autoimmune disorders which may be treated using a protein of the present invention include, for example, connective tissue disease, multiple sclerosis, systemic lupus erythematosus, rheumatoid arthritis, autoimmune pulmonary inflammation, Guillain-Barre syndrome, autoimmune thyroiditis, insulin dependent diabetes mellitus, myasthenia gravis, graft-versus-host disease and autoimmune inflammatory eye disease. Such a protein (or antagonists thereof, including antibodies) of the present invention may also be useful in the treatment of allergic reactions (e.g., anaphylaxis, serum sickness, drug reactions, food allergies, insect venom allergies, mastocytosis, allergic rhinitis, hypersensitivity pneumonitis, urticaria, angioedema, eczema, atopic dermatitis, allergic contact dermatitis, erythema multiforme, Stevens-Johnson syndrome, allergic conjunctivitis, atopic keratoconjunctivitis, venereal keratoconjunctivitis, giant papillary conjunctivitis and contact allergies) and conditions, such as asthma (particularly allergic asthma) or other respiratory problems. Other conditions, in which immune suppression is desired (including, for example, organ transplantation), may also be treatable using a protein of the present invention. The therapeutic effects of IL-1 Hy2 polypeptides or antagonists thereof on allergic reactions can be evaluated by in vivo animals models such as the cumulative contact enhancement test (Lastbom et al., Toxicology 125:59–66, 1998), skin prick test (Hoffmann et al., Allergy 54:446–54, 1999), guinea pig skin sensitization test (Vohr et al., Arch. Toxocol. 73: 501–9), and murine local lymph node assay (Kimber et al., J. Toxicol. Environ. Health 53:563–79).

Using the proteins of the invention it may also be possible to modulate immune responses, in a number of ways. Down regulation may be in the form of inhibiting or blocking an immune response already in progress or may involve preventing the induction of an immune response. The functions of activated T cells may be inhibited by suppressing T cell responses or by inducing specific tolerance in T cells, or both. Immunosuppression of T cell responses is generally an active, non-antigen-specific, process which requires continuous exposure of the T cells to the suppressive agent. Tolerance, which involves inducing non-responsiveness or anergy in T cells, is distinguishable from immunosuppression in that it is generally antigen-specific and persists after exposure to the tolerizing agent has ceased. Operationally, tolerance can be demonstrated by the lack of a T cell response upon reexposure to specific antigen in the absence of the tolerizing agent.

Down regulating or preventing one or more antigen functions (including without limitation B lymphocyte antigen functions (such as, for example, B7)), e.g., preventing high level lymphokine synthesis by activated T cells, will be useful in situations of tissue, skin and organ transplantation and in graft-versus-host disease (GVHD). For example, blockage of T cell function should result in reduced tissue destruction in tissue transplantation. Typically, in tissue transplants, rejection of the transplant is initiated through its recognition as foreign by T cells, followed by an immune reaction that destroys the transplant. The administration of a molecule which inhibits or blocks interaction of a B7 lymphocyte antigen with its natural ligand(s) on immune cells (such as a soluble, monomeric form of a peptide having B7-2 activity alone or in conjunction with a monomeric form of a peptide having an activity of another B lymphocyte antigen (e.g., B7-1, B7-3) or blocking antibody), prior to transplantation can lead to the binding of the molecule to the natural ligand(s) on the immune cells without transmitting the corresponding costimulatory signal. Blocking B lymphocyte antigen function in this matter prevents cytokine synthesis by immune cells, such as T cells, and thus acts as an immunosuppressant. Moreover, the lack of costimulation may also be sufficient to anergize the T cells, thereby inducing tolerance in a subject. Induction of long-term tolerance by B lymphocyte antigen-blocking reagents may avoid the necessity of repeated administration of these blocking reagents. To achieve sufficient immunosuppression or tolerance in a subject, it may also be necessary to block the function of a combination of B lymphocyte antigens.

The efficacy of particular blocking reagents in preventing organ transplant rejection or GVHD can be assessed using animal models that are predictive of efficacy in humans. Examples of appropriate systems which can be used include allogeneic cardiac grafts in rats and xenogeneic pancreatic islet cell grafts in mice, both of which have been used to examine the immunosuppressive effects of CTLA41 g fusion proteins in vivo as described in Lenschow et al., Science 257:789–792 (1992) and Turka et al., Proc. Natl. Acad. Sci USA, 89:11102–11105 (1992). In addition, murine models of GVHD (see Paul ed., Fundamental Immunology, Raven Press, New York, 1989, pp. 846–847) can be used to determine the effect of blocking B lymphocyte antigen function in vivo on the development of that disease.

Blocking antigen function may also be therapeutically useful for treating autoimmune diseases. Many autoimmune disorders are the result of inappropriate activation of T cells that are reactive against self tissue and which promote the production of cytokines and autoantibodies involved in the pathology of the diseases. Preventing the activation of autoreactive T cells may reduce or eliminate disease symptoms. Administration of reagents which block costimulation of T cells by disrupting receptor:ligand interactions of B lymphocyte antigens can be used to inhibit T cell activation and prevent production of autoantibodies or T cell-derived cytokines which may be involved in the disease process. Additionally, blocking reagents may induce antigen-specific tolerance of autoreactive T cells which could lead to long-term relief from the disease. The efficacy of blocking reagents in preventing or alleviating autoimmune disorders can be determined using a number of well-characterized animal models of human autoimmune diseases. Examples include murine experimental autoimmune encephalitis, systemic lupus erythmatosis in MRL/1pr/1pr mice or NZB hybrid mice, murine autoimmune collagen arthritis, diabetes mellitus in NOD mice and BB rats, and murine experimental myasthenia gravis (see Paul ed., Fundamental Immunology, Raven Press, New York, 1989, pp. 840–856).

Upregulation of an antigen function (preferably a B lymphocyte antigen function), as a means of up regulating immune responses, may also be useful in therapy. Upregulation of immune responses may be in the form of enhancing an existing immune response or eliciting an initial immune response. For example, enhancing an immune response through stimulating B lymphocyte antigen function may be useful in cases of viral infection. In addition, systemic viral diseases such as influenza, the common cold, and encephalitis might be alleviated by the administration of stimulatory forms of B lymphocyte antigens systemically.

Alternatively, anti-viral immune responses may be enhanced in an infected patient by removing T cells from the patient, costimulating the T cells in vitro with viral antigen-pulsed APCs either expressing a peptide of the present invention or together with a stimulatory form of a soluble peptide of the present invention and reintroducing the in vitro activated T cells into the patient. Another method of enhancing anti-viral immune responses would be to isolate infected cells from a patient, transfect them with a nucleic acid encoding a protein of the present invention as described herein such that the cells express all or a portion of the protein on their surface, and reintroduce the transfected cells into the patient. The infected cells would now be capable of delivering a costimulatory signal to, and thereby activate, T cells in vivo.

The presence of the peptide of the present invention having the activity of a B lymphocyte antigen(s) on the surface of the tumor cell provides the necessary costimulation signal to T cells to induce a T cell mediated immune response against the transfected tumor cells. In addition, tumor cells which lack MHC class I or MHC class II molecules, or which fail to reexpress sufficient mounts of MHC class I or MHC class II molecules, can be transfected with nucleic acid encoding all or a portion of (e.g., a cytoplasmic-domain truncated portion) of an MHC class I α chain protein and $\beta_2$ microglobulin protein or an MHC class II .alpha. chain protein and an MHC class II β chain protein to thereby express MHC class I or MHC class II proteins on the cell surface. Expression of the appropriate class I or class II MHC in conjunction with a peptide having the activity of a B lymphocyte antigen (e.g., B7-1, B7-2, B7-3) induces a T cell mediated immune response against the transfected tumor cell. Optionally, a gene encoding an antisense construct which blocks expression of an MHC class II associated protein, such as the invariant chain, can also be cotransfected with a DNA encoding a peptide having the activity of a B lymphocyte antigen to promote presentation of tumor associated antigens and induce tumor specific immunity. Thus, the induction of a T cell mediated immune response in a human subject may be sufficient to overcome tumor-specific tolerance in the subject.

The activity of a protein of the invention may, among other means, be measured by the following methods:

Suitable assays for thymocyte or splenocyte cytotoxicity include, without limitation, those described in: Current Protocols in Immunology, Ed by J. E. Coligan, A. M. Kruisbeek, D. H. Margulies, E. M. Shevach, W. Strober, Pub. Greene Publishing Associates and Wiley-Interscience (Chapter 3, In Vitro assays for Mouse Lymphocyte Function 3.1–3.19; Chapter 7, Immunologic studies in Humans); Herrmann et al., Proc. Natl. Acad. Sci. USA 78:2488–2492, 1981; Herrmann et al., J. Immunol. 128:1968–1974, 1982; Handa et al., J. Immunol. 135:1564–1572, 1985; Takai et al., I. Immunol. 137:3494–3500, 1986; Takai et al., J. Immunol. 140:508–512, 1988; Herrmann et al., Proc. Natl. Acad. Sci. USA 78:2488–2492, 1981; Herrmann et al., J. Immunol. 128:1968–1974, 1982; Handa et al., J. Immunol. 135:1564–1572, 1985; Takai et al., J. Immunol. 137:3494–3500, 1986; Bowman et al., J. Virology 61:1992–1998; Takai et al., J. Immunol. 140:508–512, 1988; Bertagnolli et al., Cellular Immunology 133:327–341, 1991; Brown et al., J. Immunol. 153:3079–3092, 1994.

Assays for T-cell-dependent immunoglobulin responses and isotype switching (which will identify, among others, proteins that modulate T-cell dependent antibody responses and that affect Th1/Th2 profiles) include, without limitation, those described in: Maliszewski, J. Immunol. 144:3028–3033, 1990; and Assays for B cell function: In vitro antibody production, Mond, J. J. and Brunswick, M. In Current Protocols in Immunology. J. E. e.a. Coligan eds. Vol 1 pp. 3.8.1–3.8.16, John Wiley and Sons, Toronto. 1994.

Mixed lymphocyte reaction (MLR) assays (which will identify, among others, proteins that generate predominantly Th1 and CTL responses) include, without limitation, those described in: Current Protocols in Immunology, Ed by J. E. Coligan, A. M. Kruisbeek, D. H. Margulies, E. M. Shevach, W. Strober, Pub. Greene Publishing Associates and Wiley-Interscience (Chapter 3, In Vitro assays for Mouse Lymphocyte Function 3.1–3.19; Chapter 7, Immunologic studies in Humans); Takai et al., J. Immunol. 137:3494–3500, 1986; Takai et al., J. Immunol. 140:508–512, 1988; Bertagnolli et al., J. Immunol. 149:3778–3783, 1992.

Dendritic cell-dependent assays (which will identify, among others, proteins expressed by dendritic cells that activate naive T-cells) include, without limitation, those described in: Guery et al., J. Immunol. 134:536–544, 1995; Inaba et al., Journal of Experimental Medicine 173:549–559, 1991; Macatonia et al., Journal of Immunology 154:5071–5079, 1995; Porgador et al., Journal of Experimental Medicine 182:255–260, 1995; Nair et al., Journal of Virology 67:4062–4069, 1993; Huang et al., Science 264:961–965, 1994; Macatonia et al., Journal of Experimental Medicine 169:1255–1264, 1989; Bhardwaj et al., Journal of Clinical Investigation 94:797–807, 1994; and Inaba et al., Journal of Experimental Medicine 172:631–640, 1990.

Assays for lymphocyte survival/apoptosis (which will identify, among others, proteins that prevent apoptosis after superantigen induction and proteins that regulate lymphocyte homeostasis) include, without limitation, those described in: Darzynkiewicz et al., Cytometry 13:795–808, 1992; Gorczyca et al., Leukemia 7:659–670, 1993; Gorczyca et al., Cancer Research 53:1945–1951, 1993; Itoh et al., Cell 66:233–243, 1991; Zacharchuk, Journal of Immunology 145:4037–4045, 1990; Zamai et al., Cytometry 14:891–897, 1993; Gorczyca et al., International Journal of Oncology 1:639–648, 1992.

Assays for proteins that influence early steps of T-cell commitment and development include, without limitation, those described in: Antica et al., Blood 84:111–117, 1994; Fine et al., Cellular Immunology 155:111–122, 1994; Galy et al., Blood 85:2770–2778, 1995; Toki et al., Proc. Nat. Acad Sci. USA 88:7548–7551, 1991.

6.5. Hematopoiesis Regulating Activity

A protein of the present invention may be useful in regulation of hematopoiesis and, consequently, in the treatment of myeloid or lymphoid cell deficiencies. Even marginal biological activity in support of colony forming cells or of factor-dependent cell lines indicates involvement in regulating hematopoiesis, e.g. in supporting the growth and proliferation of erythroid progenitor cells alone or in combination with other cytokines, thereby indicating utility, for example, in treating various anemias or for use in conjunction with irradiation/chemotherapy to stimulate the production of erythroid precursors and/or erythroid cells; in supporting the growth and proliferation of myeloid cells such as granulocytes and monocytes/macrophages (i.e., traditional CSF activity) useful, for example, in conjunction with chemotherapy to prevent or treat consequent myelosuppression; in supporting the growth and proliferation of megakaryocytes and consequently of platelets thereby allowing prevention or treatment of various platelet disorders such as thrombocytopenia, and generally for use in place of or complimentary to platelet transfusions; and/or in supporting the growth and proliferation of hematopoietic stem cells which are capable of maturing to any and all of the above-mentioned hematopoietic cells and therefore find therapeutic utility in various stem cell disorders (such as those usually treated with transplantation, including, without limitation, aplastic anemia and paroxysmal nocturnal hemoglobinuria), as well as in repopulating the stem cell compartment post irradiation/chemotherapy, either in-vivo or ex-vivo (i.e., in conjunction with bone marrow transplantation or with peripheral progenitor cell transplantation (homologous or heterologous)) as normal cells or genetically manipulated for gene therapy.

The activity of a protein of the invention may, among other means, be measured by the following methods:

Suitable assays for proliferation and differentiation of various hematopoietic lines are cited above.

Assays for embryonic stem cell differentiation (which will identify, among others, proteins that influence embryonic differentiation hematopoiesis) include, without limitation, those described in: Johansson et al. Cellular Biology 15:141–151, 1995; Keller et al., Molecular and Cellular Biology 13:473–486, 1993; McClanahan et al., Blood 81:2903–2915, 1993.

Assays for stem cell survival and differentiation (which will identify, among others, proteins that regulate lymphohematopoiesis) include, without limitation, those described in: Methylcellulose colony forming assays, Freshney, M. G. In Culture of Hematopoietic Cells. R. I. Freshney, et al. eds. Vol pp. 265–268, Wiley-Liss, Inc., New York, N.Y. 1994; Hirayama et al., Proc. Natl. Acad. Sci. USA 89:5907–5911, 1992; Primitive hematopoietic colony forming cells with high proliferative potential, McNiece, I. K. and Briddell, R. A. In Culture of Hematopoietic Cells. R. I. Freshney, et al. eds. Vol pp. 23–39, Wiley-Liss, Inc., New York, N.Y. 1994; Neben et al., Experimental Hematology 22:353–359, 1994; Cobblestone area forming cell assay, Ploemacher, R. E. In Culture of Hematopoietic Cells. R. I. Freshney, et al. eds. Vol pp. 1–21, Wiley-Liss, Inc., New York, N.Y. 1994; Long term bone marrow cultures in the presence of stromal cells, Spooncer, E., Dexter, M. and Allen, T. In Culture of Hematopoietic Cells. R. 1. Freshney, et al. eds. Vol pp. 163–179, Wiley-Liss, Inc., New York, N.Y. 1994; Long term culture initiating cell assay, Sutherland, H. J. In Culture of Hematopoietic Cells. R. I. Freshney, et al. eds. Vol pp. 139–162, Wiley-Liss, Inc., New York, N.Y. 1994.

6.6. Tissue Growth Activity

A protein of the present invention also may have utility in compositions used for bone, cartilage, tendon, ligament and/or nerve tissue growth or regeneration, as well as for wound healing and tissue repair and replacement, and in the treatment of burns, incisions and ulcers.

A protein of the present invention, which induces cartilage and/or bone growth in circumstances where bone is not normally formed, has application in the healing of bone fractures and cartilage damage or defects in humans and other animals. Such a preparation employing a protein of the invention may have prophylactic use in closed as well as open fracture reduction and also in the improved fixation of artificial joints. De novo bone formation induced by an osteogenic agent contributes to the repair of congenital, trauma induced, or oncologic resection induced craniofacial defects, and also is useful in cosmetic plastic surgery.

A protein of this invention may also be used in the treatment of periodontal disease, and in other tooth repair processes. Such agents may provide an environment to attract bone-forming cells, stimulate growth of bone-forming cells or induce differentiation of progenitors of bone-forming cells. A protein of the invention may also be useful in the treatment of osteoporosis or osteoarthritis, such as through stimulation of bone and/or cartilage repair or by blocking inflammation or processes of tissue destruction (collagenase activity, osteoclast activity, etc.) mediated by inflammatory processes.

Another category of tissue regeneration activity that may be attributable to the protein of the present invention is tendon/ligament formation. A protein of the present invention, which induces tendon/ligament-like tissue or other tissue formation in circumstances where such tissue is not normally formed, has application in the healing of tendon or ligament tears, deformities and other tendon or ligament defects in humans and other animals. Such a preparation employing a tendon/ligament-like tissue inducing protein may have prophylactic use in preventing damage to tendon or ligament tissue, as well as use in the improved fixation of tendon or ligament to bone or other tissues, and in repairing defects to tendon or ligament tissue. De novo tendon/ligament-like tissue formation induced by a composition of the present invention contributes to the repair of congenital, trauma induced, or other tendon or ligament defects of other origin, and is also useful in cosmetic plastic surgery for attachment or repair of tendons or ligaments. The compositions of the present invention may provide environment to attract tendon- or ligament-forming cells, stimulate growth of tendon- or ligament-forming cells, induce differentiation of progenitors of tendon- or ligament-forming cells, or induce growth of tendon/ligament cells or progenitors ex vivo for return in vivo to effect tissue repair. The compositions of the invention may also be useful in the treatment of tendinitis, carpal tunnel syndrome and other tendon or ligament defects. The compositions may also include an appropriate matrix and/or sequestering agent as a carrier as is well known in the art.

The protein of the present invention may also be useful for proliferation of neural cells and for regeneration of nerve and brain tissue, i.e. for the treatment of central and peripheral nervous system diseases and neuropathies, as well as mechanical and traumatic disorders, which involve degeneration, death or trauma to neural cells or nerve tissue. More specifically, a protein may be used in the treatment of diseases of the peripheral nervous system, such as peripheral nerve injuries, peripheral neuropathy and localized neuropathies, and central nervous system diseases, such as Alzheimer's, Parkinson's disease, Huntington's disease, amyotrophic lateral sclerosis, and Shy-Drager syndrome. Further conditions which may be treated in accordance with the present invention include mechanical and traumatic disorders, such as spinal cord disorders, head trauma and cerebrovascular diseases such as stroke. Peripheral neuropathies resulting from chemotherapy or other medical therapies may also be treatable using a protein of the invention.

Proteins of the invention may also be useful to promote better or faster closure of non-healing wounds, including without limitation pressure ulcers, ulcers associated with vascular insufficiency, surgical and traumatic wounds, and the like.

It is expected that a protein of the present invention may also exhibit activity for generation or regeneration of other tissues, such as organs (including, for example, pancreas, liver, intestine, kidney, skin, endothelium), muscle (smooth, skeletal or cardiac) and vascular (including vascular endothelium) tissue, or for promoting the growth of cells comprising such tissues. Part of the desired effects may be by inhibition or modulation of fibrotic scarring to allow normal tissue to regenerate. A protein of the invention may also exhibit angiogenic activity.

A protein of the present invention may also be useful for gut protection or regeneration and treatment of lung or liver fibrosis, reperfusion injury in various tissues, and conditions resulting from systemic cytokine damage.

A protein of the present invention may also be useful for promoting or inhibiting differentiation of tissues described above from precursor tissues or cells; or for inhibiting the growth of tissues described above.

The activity of a protein of the invention may, among other means, be measured by the following methods:

Assays for tissue generation activity include, without limitation, those described in: International Patent Publication No. WO95/16035 (bone, cartilage, tendon); International Patent Publication No. WO95/05846 (nerve, neuronal); International Patent Publication No. WO91/07491 (skin, endothelium).

Assays for wound healing activity include, without limitation, those described in: Winter, Epidermal Wound Healing, pps. 71–112 (Maibach, H. 1. and Rovee, D. T., eds.), Year Book Medical Publishers, Inc., Chicago, as modified by Eaglstein and Mertz, J. Invest. Dermatol 71:382–84 (1978).

6.7. Activin/Inhibin Activity

A protein of the present invention may also exhibit activin- or inhibin-related activities. A polynucleotide of the invention may encode a polypeptide exhibiting such characteristics. Inhibins are characterized by their ability to inhibit the release of follicle stimulating hormone (FSH), while activins and are characterized by their ability to stimulate the release of follicle stimulating hormone (FSH). Thus, a protein of the present invention, alone or in heterodimers with a member of the inhibin c-family, may be useful as a contraceptive based on the ability of inhibins to decrease fertility in female mammals and decrease spermatogenesis in male mammals. Administration of sufficient amounts of other inhibins can induce infertility in these mammals. Alternatively, the protein of the invention, as a homodimer or as a heterodimer with other protein subunits of the inhibin-β group, may be useful as a fertility inducing therapeutic, based upon the ability of activin molecules in stimulating FSH release from cells of the anterior pituitary. See, for example, U.S. Pat. No. 4,798,885. A protein of the invention may also be useful for advancement of the onset of fertility in sexually immature mammals, so as to increase the lifetime reproductive performance of domestic animals such as cows, sheep and pigs.

The activity of a protein of the invention may, among other means, be measured by the following methods:

Assays for activin/inhibin activity include, without limitation, those described in: Vale et al., Endocrinology 91:562–572, 1972; Ling et al., Nature 321:779–782, 1986; Vale et al., Nature 321:776–779, 1986; Mason et al., Nature 318:659–663, 1985; Forage et al., Proc. Natl. Acad. Sci. USA 83:3091–3095, 1986.

6.8. Chemotactic Chemokinetic Activity

A protein of the present invention may have chemotactic or chemokinetic activity (e.g., act as a chemokine) for mammalian cells, including, for example, monocytes, fibroblasts, neutrophils, T-cells, mast cells, eosinophils, epithelial and/or endothelial cells. A polynucleotide of the invention can encode a polypeptide exhibiting such attributes. Chemotactic and chemokinetic proteins can be used to mobilize or attract a desired cell population to a desired site of action. Chemotactic or chemokinetic proteins provide particular advantages in treatment of wounds and other trauma to tissues, as well as in treatment of localized infections. For example, attraction of lymphocytes, monocytes or neutrophils to tumors or sites of infection may result in improved immune responses against the tumor or infecting agent.

A protein or peptide has chemotactic activity for a particular cell population if it can stimulate, directly or indirectly, the directed orientation or movement of such cell population. Preferably, the protein or peptide has the ability to directly stimulate directed movement of cells. Whether a particular protein has chemotactic activity for a population of cells can be readily determined by employing such protein or peptide in any known assay for cell chemotaxis.

The activity of a protein of the invention may, among other means, be measured by the following methods:

Assays for chemotactic activity (which will identify proteins that induce or prevent chemotaxis) consist of assays that measure the ability of a protein to induce the migration of cells across a membrane as well as the ability of a protein to induce the adhesion of one cell population to another cell population. Suitable assays for movement and adhesion include, without limitation, those described in: Current Protocols in Immunology, Ed by J. E. Coligan, A. M. Kruisbeek, D. H. Marguiles, E. M. Shevach, W. Strober, Pub. Greene Publishing Associates and Wiley-Interscience (Chapter 6.12, Measurement of alpha and beta Chemokines 6.12.1–6.12.28); Taub et al. J. Clin. Invest. 95:1370–1376, 1995; Lind et al. APMIS 103:140–146, 1995; Muller et al Eur. J. Immunol. 25:1744–1748; Gruber et al. J. of Immunol. 152:5860–5867, 1994; Johnston et al. J. of Immunol. 153:1762–1768, 1994.

6.9. Hemostatic and Thrombolytic Activity

A protein of the invention may also exhibit hemostatic or thrombolytic activity. A polynucleotide of the invention can encode a polypeptide exhibiting such attributes. Such a protein is expected to be useful in treatment of various coagulation disorders (including hereditary disorders, such as hemophilias) or to enhance coagulation and other hemostatic events in treating wounds resulting from trauma, surgery or other causes. A protein of the invention may also be useful for dissolving or inhibiting formation of thromboses and for treatment and prevention of conditions resulting therefrom (such as, for example, infarction of cardiac and central nervous system vessels (e.g., stroke).

The activity of a protein of the invention may, among other means, be measured by the following methods:

Assay for hemostatic and thrombolytic activity include, without limitation, those described in: Linet et al., J. Clin. Pharmacol. 26:131–140, 1986; Burdick et al., Thrombosis Res. 45:413–419, 1987; Humphrey et al., Fibrinolysis 5:71–79 (1991); Schaub, Prostaglandins 35:467–474, 1988.

6.10. Receptor/Ligand Activity

A protein of the present invention may also demonstrate activity as receptors, receptor ligands or inhibitors or agonists of receptor/ligand interactions. A polynucleotide of the invention can encode a polypeptide exhibiting such characteristics. Examples of such receptors and ligands include, without limitation, cytokine receptors and their ligands, receptor kinases and their ligands, receptor phosphatases and their ligands, receptors involved in cell-cell interactions and their ligands (including without limitation, cellular adhesion molecules (such as selecting, integrins and their ligands) and receptor/ligand pairs involved in antigen presentation, antigen recognition and development of cellular and humoral immune responses). Receptors and ligands are also useful for screening of potential peptide or small molecule inhibitors of the relevant receptor/ligand interaction. A protein of the present invention (including, without limitation, fragments of receptors and ligands) may themselves be useful as inhibitors of receptor/ligand interactions.

The activity of a protein of the invention may, among other means, be measured by the following methods:

Suitable assays for receptor-ligand activity include without limitation those described in: Current Protocols in Immunology, Ed by J. E. Coligan, A. M. Kruisbeek, D. H. Margulies, E. M. Shevach, W. Strober, Pub. Greene Publishing Associates and Wiley-Interscience (Chapter 7.28, Measurement of Cellular Adhesion under static conditions 7.28.1–7.28.22), Takai et al., Proc. Natl. Acad. Sci. USA 84:6864–6868, 1987; Bierer et al., J. Exp. Med. 168:1145–1156, 1988; Rosenstein et al., J. Exp. Med. 169:149–160 1989; Stoltenborg et al., J. Immunol. Methods 175:59–68, 1994; Stitt et al., Cell 80:661–670, 1995.

By way of example, the IL-1 Hy2 polypeptides of the invention may be used as a ligand for a cytokine receptor thereby modulating (i.e., enhancing or inhibiting) the biological activity of that receptor. Examples of cytokine receptors that may be used include, but are not limited to, the Interleukin-1 Type I or Type II Receptors. Whether the IL-1 Hy2 polypeptides of the invention exhibit agonist, partial agonist, antagonist, or partial antagonist activity for a particular receptor, such as a cytokine receptor, in a particular cell type can be determined by conventional techniques known to those skilled in the art, such as those described below in sections 6.11.1 and 6.11.2 and in the Examples below. In one embodiment, one or more cells expressing a cytokine receptor (e.g., Interleukin-1 Type I or Type II Receptors) are contacted with the protein of the invention. Examples of cells that may be contacted with the protein of the invention include, but are not limited to, mammalian cells such as fibroblasts and T-cells. Preferably the novel protein of the invention acts as an antagonist for a cytokine receptor (e.g.-the Interleukin-1 Receptor) so that the biological activities of that receptor are inhibited.

Studies characterizing drugs or proteins as agonist or antagonist or partial agonists a partial antagonist require the use of other proteins as competing ligands. The polypeptides of the present invention are expected to exhibit an affinity for Interleukin-1 Receptor. Thus, the polypeptides of the present invention may be used, for example, as competitors in assays involving Interleukin-1 Receptors. Alternatively, the polypeptides of the invention may be labelled by being coupled to radioisotopes, colorimetric molecules or a toxin molecules by conventional methods ("Guide to Protein Purification" Murray P. Deutscher (ed) Methods in Enzymology Vol. 182 (1990) Academic Press, Inc. San Diego) and used in both in vivo and in vitro to bind to the Interleukin-1 Receptor. Examples of radioisotopes include, but are not limited to, tritium and carbon-14. Examples of colorimetric molecules include, but are not limited to, fluorescent molecules such as fluorescamine, or rhodamine or other calorimetric molecules. Examples of toxins include, but are not limited, to ricin. By way of example, the proteins coupled to such molecules are useful in studies involving in vivo or in vitro metabolism of the Interleukin-1 Receptor.

6.11 Drug Screening with Interleukin-1 Hy2 Polypeptides

This invention is particularly useful for screening compounds by using the IL-1 Hy2 polypeptides of the invention, particularly binding fragments, in any of a variety of drug screening techniques. The polypeptides employed in such a test may either be free in solution, affixed to a solid support, borne on a cell surface or located intracellularly. One method of drug screening utilizes eukaryotic or prokaryotic host cells which are stably transformed with recombinant nucleic acids expressing the desired IL-1 Hy2 polypeptide. Drugs are screened against such transformed cells in competitive binding assays. Such cells, either in viable or fixed form, can be used for standard binding assays. One may measure, for example, the formation of complexes between IL-1 Hy2 polypeptides of the invention and the agent being tested or examine the diminution in complex formation between the IL-1 Hy2 polypeptides and an appropriate cell line, which are well known in the art.

6.11.1 Assay for Anti-Interleukin-1 Receptor Activity

In one embodiment, the Interleukin-1 receptor antagonist activity of the polypeptides of the invention is determined using a method that involve (1) forming a mixture comprising Interleukin-1, the Interleukin-1 receptor, and the IL-1 Hy2 polypeptides of the invention and/or its agonists and antagonists (or agonist or antagonist drug candidates) and/or antibodies specific for the IL-1 Hy2 polypeptides of the invention; (2) incubating the mixture under conditions whereby, but for the presence of said IL-1 Hy2 polypeptide of the invention and/or its agonists and antagonists (or agonist or antagonist drug candidates) and/or antibodies specific for the IL-1 Hy2 polypeptides of the invention, the Interleukin-1 binds to the Interleukin-1 receptor; and (3) detecting the presence or absence of specific binding of Interleukin-1 to the Interleukin-1 receptor.

6.11.2 Assay For Antagonists and Agonists

Human HepG2 cells are incubated at 37 degree(s) C. for 18–24 hours in serum-free Dulbecco's modified Eagle medium. Separate monolayers of cells are incubated in the same medium supplemented with Interleukin-1 at various concentrations and in the same medium supplemented with a IL-1 Hy2 polypeptide of the invention at various concentrations.

Monolayers are rinsed vigorously with isotonic buffer and incubated in (35-S) methionine, 250 mu ci/ml methionine-free medium and pulsed for a period of 15–30 minutes to assess net synthesis. Cell culture fluid is discarded and monolayers are again rinsed and resuspended in cell lysis buffer. The newly synthesized radiolabelled hepatic proteins in these cell lysates are detected by immunoprecipitation, SDS-PAGE and fluorography.

6.12. Anti-Inflammatory Activity

Proteins of the present invention may also exhibit anti-inflammatory activity. The anti-inflammatory activity may be achieved by providing a stimulus to cells involved in the inflammatory response, by inhibiting or promoting cell-cell interactions (such as, for example, cell adhesion), by inhibiting or promoting chemotaxis of cells involved in the inflammatory process, inhibiting or promoting cell extravasation, or by stimulating or suppressing production of other factors which more directly inhibit or promote an inflammatory response. Proteins exhibiting such activities can be used to treat inflammatory conditions including chronic or acute conditions), including without limitation intimation associated with infection (such as septic shock, sepsis or systemic inflammatory response syndrome (SIRS)), ischemia-reperfusion injury, endotoxin lethality, arthritis, complement-mediated hyperacute rejection, nephritis, cytokine or chemokine-induced lung injury, inflammatory bowel disease, Crohn's disease or resulting from over production of cytokines such as TNF or IL-1. Proteins of the invention may also be useful to treat anaphylaxis and hypersensitivity to an antigenic substance or material. In particular, the IL-1 Hy2 polypeptides of this invention may be utilized to prevent or treat condition such as, but not limited to, utilized, for example, as part of methods for the prevention and/or treatment of disorders involving sepsis, acute pancreatitis, endotoxic shock, cytokine induced shock, rheumatoid arthritis, chronic inflammatory arthritis, pancreatic cell damage from diabetes mellitus type 1, graft versus host disease, inflammatory bowel disease, inflamation associated with pulmonary disease, other autoimmune disease or inflammatory disease, an anti-proliferative agent such as for acute or chronic mylegenous leukemia or in the prevention of premature labor secondary to intrauterine infections.

6.13 Modulation of IL-18, IL-12 and IFN-γ Related Disorders

Administration of IL-1 Hy2 polynucleotides, polypeptides and agonists is also expected to be useful for the treatment of IL-18 and/or IL-12 and/or IFN-γ related disorders. IL-1 Hy2 inhibits IL-18 and IL-12 activity, including IL-18 and IL-12 induced IFN-γ production.

IL-18 has been found to have a variety of biological activities including the stimulation of activated T cell proliferation, enhancement of NK cell lytic activity, induction of IFNγ secretion, enhancement of Fas ligand expression and function, and stimulation of granulocyte-macrophage colony-stimulating factor (GM-CSF) production by activated T cells. IL-18 has been shown to counteract viral and intracellular infections and suppress tumor formation. However, IL-18 is also involved in the pathogenic progression of chronic inflammatory diseases, including endotoxin-induced shock, liver injury (including endotoxin-induced liver injury, hepatitis, biliary atresia and obesity-related fatty liver) and autoimmune diseases. Other disorders related to IL-18 production include meliodosis, purine nucleoside phosphorylase deficiency, increased susceptibility to Leishmania major and Staphylococcus aureus infection, hemophagocytic lymphohistiocytosis, mononucleosis, viral meningitis/encephalitis, bacterial meningitis/encephalitis and ischemia or ischemia/reperfusion injury.

Inflammation may result from infection with pathogenic organisms (including gram-positive bacteria, gram-negative bacteria, viruses, fungi, and parasites such as protozoa and helminths), transplant rejection (including rejection of solid organs such as kidney, liver, heart, lung or cornea, as well as rejection of bone marrow transplants including graft versus host disease (GVHD)), or from localized chronic or acute autoimmune or allergic reactions. Autoimmune diseases include acute glomerulonephritis; rheumatoid or reactive arthritis; chronic glomerulonephritis;

inflammatory bowel diseases such as Crohn's disease, ulcerative colitis and necrotizing enterocolitis; granulocyte transfusion associated syndromes; inflammatory dermatoses such as contact dermatitis, atopic dermatitis, psoriasis; systemic lupus erythematosus (SLE), autoimmune thyroiditis, multiple sclerosis, some forms of diabetes, or any other autoimmune state where attack by the subject's own immune system results in pathologic tissue destruction. Allergic reactions include allergic asthma, chronic bronchitis, allergic rhinitis, acute and delayed hypersensitivity. Systemic inflammatory disease states include inflammation associated with trauma, burns, reperfusion following ischemic events (e.g. thrombotic events in heart, brain, intestines or peripheral vasculature, including myocardial infarction and stroke), sepsis, ARDS or multiple organ dysfunction syndrome. Inflammatory cell recruitment also occurs in atherosclerotic plaques.

Endotoxin activation of the systemic inflammatory response leads to a number of disorders including bacterial and/or endotoxin-related shock, fever, tachycardia, tachypnea, cytokine overstimulation, increased vascular permeability, hypotension, complement activation, disseminated intravascular coagulation, anemia, thrombocytopenia, leukopenia, pulmonary edema, adult respiratory distress syndrome, intestinal ischemia, renal insufficiency and failure, and metabolic acidosis.

Hepatitis represents liver disorders that are characterized by hepatic inflammation and necrosis that can be manifested as an acute or chronic condition. These liver disorders include virus-induced hepatitis such as hepatitis A, hepatitis B, hepatitis C (non-A, non-B hepatitis), hepatitis D, hepatitis E; toxin and drug induced hepatitis such as acetaminophohen hepatotoxicity, halothane hepatotoxicity, mehtyldopa hepatoxicity, iaoniazid hepatoxicity, sodium valproate hepatoxicity, phenytion hepatoxicity, chlorpromazine hepatoxicity, amiodarone hepatoxicity, amioidarone hepatoxicity, erythromycin hepatoxicity, oral contraceptive hepatoxicity, 17,α-alkyl-substituted anabolic steroid hepatoxicity and trimethoprim-sulfamethoxazole hepatoxicity; cholestatic hepatitis; alcoholic hepatitis; autoimmune chronic active hepatitis; and T cell mediated hepatitis. Other conditions that cause liver injury include congenital bilary atresia, obesity-related fatty liver and the autosomal recessive disease heamophagocytic lymphohistocytosis (HLH).

IL-18 induced IFN-γ plays a role in liver injury IFN-γ has been shown to mediate LPS-induced liver injury following Propionibacterium acnes infection as described in Tsuji et al. (J. Immunol. 162:1049–55, 1999). Large number of macrophages and lymphocytes infiltrate the portal area in response to P. acnes infection which results in intrahepatic formation of granulomas. IFNγ knock out mice exhibited less macrophage infiltration and a reduction in the number and size of granulomas. Subsequent treatment with low doses of LPS caused massive hepatic necrosis and increased IL-12, IL-18 and TNF-α serum levels in the normal mice, while the knock out mice exhibited drastic decreases in IL-12, IL-18 and TNF-α serum levels. The addition of IFNγ neutralizing antibody also caused a decrease in IL-18 and IL-12 levels. This model of liver injury indicates that LPS-induced liver injury is associated with increased levels of IL-18, IL-12 and IFN-γγ. Currently, a role for IL-1β is not known in this liver injury model. Since IL-1β is known to be induced by LPS, it is possible IL-1β also plays a role in the disorder. Treatment with IL-Ra may modulate the severity of liver injury due to IL-18 induced IFN-γ production and IL-1β.

IL-18 has also been shown to be involved in the immunomediated hepatitis model where treatment with concavalin A induced hepatitis in mice as described by Fiorucci et al. (Gastroenterology 118:404–21, 2000). In this model, CD+ Tcells and Th1-like cytokines cause Fas mediated liver cell death. Treatment with a nitric oxide derivative of aspirin protected against this cell death by reducing production of IFNγ, IL-18, IL-12, IL-2β and TNF-α. In addition, a neutralizing antibody to IL-18 caused a decrease in IFNγ production and reduced liver injury induced by conA.

HLH is a fatal autosomal recessive disease that manifests in early childhood. This disease is characterized by fever, hepatosplenomegaly, cytopenia and widespread infiltration of vital organs by activated lymphocytes and macrophages. Patients with HLH exhibit elevated serum levels of IL-18. IL-18 plays an important role in the induction of Thl cells in HLH patients. (Takada et al., Br. J. Haematol. 106:182–9, 1999).

IL-1 Hy2 inhibits IL-18 induced production of IFNγ. In the models described above, the degree of IL-1β activity is not known. Since IL-1β is known to be induced by LPS, it is possible that IL-1β also play a role in the pathogenicity of these conditions. The presence of the appropriate amount of IL-1 Hy2 polynucleotides, polypeptides or other agonists may modulate the severity of the disease states due to both IL-18 induced IFNγ production and IL-1β.

IL-12 is known to potentiate IFNγ production, and the cytolytic activity of NK cells and cytotoxic T lymphocytes. These immunomodulatory effects have implicated a role for IL-12 in therapies for cancer and infectious disease. However, these same therapeutic effects can also promote autoimmune diseases and chronic inflammatory conditions such as multiple sclerosis, transplant rejection and cytotoxicity.

IL-12 and IFN-γ are involved in the pathogenesis of multiple sclerosis (MS). In the experimental allergic encephalomyelitis animal model (EAE), the demyelinating effect on the central nervous system is carried out similar to that in humans suffering from MS. Currently, IFNP is used to treat MS. The mechanism of IFNβ treatment may be to decrease the number of IFNγ producing T cells in MS patients. (Rep et al., J. Neuroimmunol. 96:92–100, 1999). In addition, IFNγ production in blood lymphocytes was found to correlate with disability score in MS patients. (Petcreit et al., Mult. Scler. 6:19–23, 2000). Antibodies against IL-12 were found to prevent superantigen-induced and spontaneous relapses of EAE in mice (Constantineseu et al., J. Immunol. 161:5097–5104, 1998). All these studies point to the involvement of IL-12 induced IFNγ production in the progression of MS in human patients. Therefore, treatment with IL-1 Hy2 polynucleotides, polypeptides or other agonists to reduce IFNγ production may be an useful therapy for MS patients.

The combination of IL-12 and IL-2 has synergistic antitumor activity in vivo. However, in clinical trials the combination resulted in significant toxicity and subsequently shock and mortality. (Cohen, Science 270:908 1995). In a murine model investigated by Carson et al. (J. Immunol., 162:4943–5, 1999) determined that the fatal systemic inflammatory response was NK cell dependent but not related to other effector molecules in the system such as IL-1, TNF-α, and IFNγ. IL-1 Hy2 polynucleotides, polypeptides or other agonists is expected to inhibit IL-12 induced IFN-γ production and is expected to inhibit other biological activities of IL-12 such as NK cell cytolytic activity. Inhibition of NK cell activity, through IL-Ra administration, may reduce toxicity resulting from IL-12 antitumor treatment.

The effect of IL-1 Hy2 on IL-12 and/or IL-18 activity may be determined by measuring the biological activities of these cytokines. Both IL-12 and IL-18 are known to induce IFNγ production in T cells. In addition to IFN-γ, the combination of IL-12 and IL-18 increases production of IL-3, IL-6 and TNF. Treatment with IL-1 Hy2 is expected to reduce IFNγ production induced by IL-12 and IL-18. Circulating or local levels of IFNγ in tissue or fluid samples from patients treated with IL-1 Hy2 polynucleotides, polypeptides or other agonists will be an indication of the therapeutic effects of IL-1 Hy2 on the IL-18 and IL-12 related disorders. Tissue samples include tissue samples from an area involved in inflammation or other disease. Fluid samples include, for example, whole blood, plasma, serum, cerebrospinal fluid, synovial fluid, peritoneal fluids (including lavage fluids or exudate), pleural fluids (including lavage fluids or exudate), wound fluids (including lavage fluids or exudate).

Furthermore, IL-12 is known to activate NK cells and to decrease serum IgE levels. These assays may also be used to measure the effectiveness of IL-1 Hy2 treatment for IL-12 related disorders. The NK cell cytolytic activity in patients treated with IL-1 Hy2 polynucleotides, polypeptides or other agonists can be assayed by measuring patient's blood samples ability to lysis colon carcinoma or lymphoma cells in vitro. (Lieberman et al., J. Sur. Res., 50:410–415, 1992) In addition, the serum levels of IgE from patients treated with IL-1 Hy2 can be measured to determine the effectiveness of treatment for IL-12 related disorders. (Kiniwa et al. J. Clin. Invest., 90:262–66, 1992)

6.14. Leukemias

Leukemias and related disorders may be treated or prevented by administration of a therapeutic that promotes or inhibits function of the polynucleotides and/or polypeptides of the invention. Such leukemias and related disorders include but are not limited to acute leukemia, acute lymphocytic leukemia, acute myelocytic leukemia, myeloblastic, promyelocytic, myelomonocytic, monocytic, erythroleukemia, chronic leukemia, chronic myelocytic (granulocytic) leukemia and chronic lymphocytic leukemia (for a review of such disorders, see Fishman et al., 1985, Medicine, 2d Ed., J.B. Lippincott Co., Pa.).

6.15. Nervous System Disorders

Nervous system disorders, involving cell types which can be tested for efficacy of intervention with compounds that modulate the activity of the polynucleotides and/or polypeptides of the invention, and which can be treated upon thus observing an indication of therapeutic utility, include but are not limited to nervous system injuries, and diseases or disorders which result in either a disconnection of axons, a diminution or degeneration of neurons, or demyelination. Nervous system lesions which may be treated in a patient (including human and non-human mammalian patients) according to the invention include but are not limited to the following lesions of either the central (including spinal cord, brain) or peripheral nervous systems:

(i) traumatic lesions, including lesions caused by physical injury or associated with surgery, for example, lesions which sever a portion of the nervous system, or compression injuries;

(ii) ischemic lesions, in which a lack of oxygen in a portion of the nervous system results in neuronal injury or death, including cerebral infarction or ischemia, or spinal cord infarction or ischemia;

(iii) infectious lesions, in which a portion of the nervous system is destroyed or injured as a result of infection, for example, by an abscess or associated with infection by human immunodeficiency virus, herpes zoster, or herpes simplex virus or with Lyme disease, tuberculosis, syphilis;

(iv) degenerative lesions, in which a portion of the nervous system is destroyed or injured as a result of a degenerative process including but not limited to degeneration associated with Parkinson's disease, Alzheimer's disease, Huntington's chorea, or amyotrophic lateral sclerosis;

(v) lesions associated with nutritional diseases or disorders, in which a portion of the nervous system is destroyed or injured by a nutritional disorder or disorder of metabolism including but not limited to, vitamin B12 deficiency, folic acid deficiency, Wernicke disease, tobacco-alcohol amblyopia, Marchiafava-Bignami disease (primary degeneration of the corpus callosum), and alcoholic cerebellar degeneration;

(vi) neurological lesions associated with systemic diseases including but not limited to diabetes (diabetic neuropathy, Bell's palsy), systemic lupus erythematosus, carcinoma, or sarcoidosis;

(vii) lesions caused by toxic substances including alcohol, lead, or particular neurotoxins; and (viii) demyelinated lesions in which a portion of the nervous system is destroyed or injured by a demyelinating disease including but not limited to multiple sclerosis, human immunodeficiency virus-associated myelopathy, transverse myelopathy or various etiologies, progressive multifocal leukoencephalopathy, and central pontine myelinolysis.

Therapeutics which are useful according to the invention for treatment of a nervous system disorder may be selected by testing for biological activity in promoting the survival or differentiation of neurons. For example, and not by way of limitation, therapeutics which elicit any of the following effects may be useful according to the invention:

(i) increased survival time of neurons in culture;

(ii) increased sprouting of neurons in culture or in vivo;

(iii) increased production of a neuron-associated molecule in culture or in vivo, e.g., choline acetyltransferase or acetylcholinesterase with respect to motor neurons; or (iv) decreased symptoms of neuron dysfunction in vivo.

Such effects may be measured by any method known in the art. In preferred, non-limiting embodiments, increased survival of neurons may be measured by the method set forth in Arakawa et al. (1990, J. Neurosci. 10:3507–3515); increased sprouting of neurons may be detected by methods set forth in Pestronk et al. (1980, Exp. Neurol. 70:65–82) or Brown et al. (1981, Ann. Rev. Neurosci. 4:17–42); increased production of neuron-associated molecules may be measured by bioassay, enzymatic assay, antibody binding, Northern blot assay, etc., depending on the molecule to be measured; and motor neuron dysfunction may be measured by assessing the physical manifestation of motor neuron disorder, e.g., weakness, motor neuron conduction velocity, or functional disability.

In a specific embodiments, motor neuron disorders that may be treated according to the invention include but are not limited to disorders such as infarction, infection, exposure to toxin, trauma, surgical damage, degenerative disease or malignancy that may affect motor neurons as well as other components of the nervous system, as well as disorders that selectively affect neurons such as amyotrophic lateral sclerosis, and including but not limited to progressive spinal muscular atrophy, progressive bulbar palsy, primary lateral sclerosis, infantile and juvenile muscular atrophy, progressive bulbar paralysis of childhood (Fazio-Londe syndrome), poliomyelitis and the post polio syndrome, and Hereditary Motorsensory Neuropathy (Charcot-Marie-Tooth Disease).

6.16. Other Activities

A protein of the invention may also exhibit one or more of the following additional activities or effects: inhibiting the growth, infection or function of, or killing, infectious agents, including, without limitation, bacteria, viruses, fungi and other parasites; effecting (suppressing or enhancing) bodily characteristics, including, without limitation, height, weight, hair color, eye color, skin, fat to lean ratio or other tissue pigmentation, or organ or body part size or shape (such as, for example, breast augmentation or diminution, change in bone form or shape); effecting biorhythms or caricadic cycles or rhythms; effecting the fertility of male or female subjects; effecting the metabolism, catabolism, anabolism, processing, utilization, storage or elimination of dietary fat, lipid, protein, carbohydrate, vitamins, minerals, co-factors or other nutritional factors or component(s); effecting behavioral characteristics, including, without limitation, appetite, libido, stress, cognition (including cognitive disorders), depression (including depressive disorders) and violent behaviors; providing analgesic effects or other pain reducing effects; promoting differentiation and growth of embryonic stem cells in lineages other than hematopoietic lineages; hormonal or endocrine activity; in the case of enzymes, correcting deficiencies of the enzyme and treating deficiency-related diseases; treatment of hyperproliferative disorders (such as, for example, psoriasis); immunoglobulin-like activity (such as, for example, the ability to bind antigens or complement); and the ability to act as an antigen in a vaccine composition to raise an immune response against such protein or another material or entity which is cross-reactive with such protein.

6.17 Identification of Polymorphisms

The demonstration of polymorphisms, for example the T125C, C184T and A205C polymorphisms illustrated in Example 2 below makes possible the identification of such polymorphisms in human subjects and the pharmacogenetic use of this information for diagnosis and treatment. Such polymorphisms may be associated with, e.g., differential predisposition or susceptibility to various disease states (such as disorders involving inflammation or immune response) or a differential response to drug administration, and this genetic information can be used to tailor preventive or therapeutic treatment appropriately. For example, the existence of a polymorphism associated with a predisposition to inflammation or autoimmune disease makes possible the diagnosis of this condition in humans by identifying the presence of the polymorphism.

Polymorphisms can be identified in a variety of ways known in the art which all generally involve obtaining a sample from a patient, analyzing DNA from the sample, optionally involving isolation or amplification of the DNA, and identifying the presence of the polymorphism in the DNA. For example, PCR may be used to amplify an appropriate fragment of genomic DNA which may then be sequenced. Alternatively, the DNA may be subjected to allele-specific oligonucleotide hybridization (in which appropriate oligonucleotides are hybridized to the DNA under conditions permitting detection of a single base mismatch) or to a single nucleotide extension assay (in which an oligonucleotide that hybridizes immediately adjacent to the position of the polymorphism is extended with one or more labelled nucleotides). In addition, traditional restriction fragment length polymorphism analysis (using restriction enzymes that provide differential digestion of the genomic DNA depending on the presence or absence of the polymorphism) may be performed.

Alternatively a polymorphism resulting in a change in the amino acid sequence could also be detected by detecting a corresponding change in amino acid sequence of the protein, e.g., by an antibody specific to the variant sequence.

7. THERAPEUTIC METHODS

The novel IL-1 Hy2 polypeptides (including fragments, analogs and variants) of the invention have numerous applications in a variety of therapeutic methods. Examples of therapeutic applications include, but are not limited to, those exemplified below.

7.1 Sepsis

One embodiment of the invention is the administration of an effective amount of the IL-1 Hy2 polypeptides of the invention to individuals that are at a high risk of developing sepsis, or that have developed sepsis. An example of the former category are patients about to undergo surgery. While the mode of administration is not particularly important, parenteral administration is preferred because of the rapid progression of sepsis, and thus, the need to have the inhibitor disseminate quickly throughout the body. Thus, the preferred mode of administration is to deliver an I.V. bolus slightly before, during, or after surgery. The dosage of the IL-1 Hy2 polypeptides of the invention will normally be determined by the prescribing physician. It is to be expected that the dosage will vary according to the age, weight and response of the individual patient. Typically, the amount of inhibitor administered per dose will be in the range of about 0.1 to 25 mg/kg of body weight, with the preferred dose being about 0.1 to 10 mg/kg of patient body weight. For parenteral administration, the IL-1 Hy2 polypeptides of the invention will be formulated in an injectable form combined with a pharmaceutically acceptable parenteral vehicle. Such vehicles are well known in the art and examples include water, saline, Ringer's solution, dextrose solution, and solutions consisting of small amounts of the human serum albumin. The vehicle may contain minor amounts of additives that maintain the isotonicity and stability of the inhibitor. The preparation of such solutions is within the skill of the art. Typically, the cytokine inhibitor will be formulated in such vehicles at a concentration of about 1–8 mg/ml to about 10 mg/ml.

7.2 Arthritis and Inflammation

The immunosuppressive effects of the Interleukin-1 inhibitor against rheumatoid arthritis is determined in an experimental animal model system. The experimental model system is adjuvant induced arthritis in rats, and the protocol is described by J. Holoshitz, et at., 1983, Science, 219:56, or by B. Waksman et al., 1963, Int. Arch. Allergy Appl. Immunol., 23:129. Induction of the disease can be caused by a single injection, generally intradermally, of a suspension of killed Mycobacterium tuberculosis in complete Freund's adjuvant (CFA). The route of injection can vary, but rats may be injected at the base of the tail with an adjuvant mixture. The inhibitor is administered in phosphate buffered solution (PBS) at a dose of about 1–5 mg/kg. The control consists of administering PBS only.

The procedure for testing the effects of the Interleukin-1 inhibitor would consist of intradermally injecting killed Mycobacterium tuberculosis in CFA followed by immediately administering the inhibitor and subsequent treatment every other day until day 24. At 14, 15, 18, 20, 22, and 24 days after injection of Mycobacterium CFA, an overall arthritis score may be obtained as described by J. Holoskitz above. An analysis of the data would reveal that the inhibitor would have a dramatic affect on the swelling of the joints as measured by a decrease of the arthritis score.

7.3 Diabetes lnterleukin-1 has been shown to be involved in the destruction of islet cells in diabetes mellitus (DM) (Mandrup-Paulsen, T., K. Bendtzen, J. Nerup, C. A. Dinarello, M. Svenson, and J. H. Nielson [1986] Diabetologia 29:63–67). The IL-1 Hy2 polypeptides of the invention limit lymphocyte and macrophage mediated damage to islet cells in incipient cases of DM identified by disease susceptibility via genetic background and family history. The inflammatory destruction of the pancreatic beta islet cells in such individuals with early DM is reduced by parenterally administering the IL-2 Hy2 polypeptides of the invention which have an anti-Interleukin-1 effect in the pancreas.

7.4 Anti-Hypotensive Arginine-Free Formulations

The parenteral formulation of the therapeutic regimen is defined as including: about 3–4 g/l isoleucine, about 4–6 g/l leucine, about 3–4 g/l lysine, about 1–2 g/l methionine, about 1–2 g/l phenylalanine, about 2–3 g/l threonine, about 0.5–1.5 g/l tryptophan, about 3–4 g/l valine, about 4–5 g/l alanine, about 1–2 g/l histidine, about 3–4 g/l proline, about 1–2 g/l serine, about 0.25–0.75 g/l tyrosine, about 4–5 g/l glycine and about 2–3 g/l aspartic acid, together in a pharmacologically acceptable excipient. In another preferred embodiment of the described parenteral formulation, the formulation may further include omithine, most particularly at a concentration of about 1–2 g/l. In still another embodiment of the described parenteral formulation, the formulation may include citrulline, most preferably at a concentration of between about 1 g/l and about 2 g/l. Both citrulline and omithine may be included in still another embodiment of the formulation, again at the concentrations indicated.

The method includes an arginine-free formulation which comprises the amino acids and concentrations thereof already described herein, together in a pharmacologically acceptable excipient. Again, the formulation may further include ornithine, citrulline, or both, to even further supply physiologically required concentrations of urea cycle substrates in the animal. Most preferably, the formulation is provided as a parenteral formulation.

Another aspect of the method comprises a method for treating chemotherapeutic agent-related hypotension. In a most preferred embodiment, the method comprises monitoring an animal receiving a chemotherapeutic agent for a decrease in systolic blood pressure to less than about 100 mm Hg to detect an animal with systemic hypotension, treating the animal having systemic hypotension with a therapeutic regimen comprising a therapeutically effective amount of an arginine-free formulation sufficient to reduce plasma or serum arginine concentrations administered concurrently with or followed by the administration of a therapeutically effective concentration of an IL-1 Hy2 polypeptide, and maintaining the animal on the therapeutic regimen until an increase of systolic blood pressure to at least about 100 mm Hg is detectable. Most preferably, the arginine-free formulation is a parenteral formulation.

In a preferred embodiment, the L-1 Hy2 polypeptides of the invention are used in combination with the anti-hypotensive arginine free formulation to treat hypotension in an animal, particularly that hypotension caused by exposure to endotoxin or septic shock.

A patient having a systolic blood pressure of less than about 100 mm Hg will be targeted for the present treatment. Such a patient is to be placed on a continuous feed of an arginine-free formulation which includes a mixture of essential and nonessential amino acids as described in U.S. Pat. No. 5,334,380. The patient is treated concurrently with the interleukin-1 antagonist polypeptides of the invention. Blood samples are to be obtained from the patient and arginine levels in the serum or plasma fraction are determined.

7.5 Pharmaceutical Formulations and Routes of Administration

A protein of the present invention (from whatever source derived, including without limitation from recombinant and non-recombinant sources) may be administered to a patient in need, by itself, or in pharmaceutical compositions where it is mixed with suitable carriers or excipient(s) at doses to treat or ameliorate a variety of disorders. Such a composition may also contain (in addition to protein and a carrier) diluents, fillers, salts, buffers, stabilizers, solubilizers, and other materials well known in the art. The term "pharmaceutically acceptable" means a non-toxic material that does not interfere with the effectiveness of the biological activity of the active ingredient(s). The characteristics of the carrier will depend on the route of administration. The pharmaceutical composition of the invention may also contain cytokines, lymphokines, or other hematopoietic factors such as M-CSF, GM-CSF, TNF, IL-1, IL-2, IL-3, IL-4, IL-5, IL-6, IL-7, IL-8, IL-9, IL-10, IL-11, IL-12, IL-13, IL-14, IL-15, IFN, TNF0, TNF1, TNF2, G-CSF, Meg-CSF, thrombopoietin, stem cell factor, and erythropoietin.

The pharmaceutical composition may further contain other agents which either enhance the activity of the protein or compliment its activity or use in treatment. Such additional factors and/or agents may be included in the pharmaceutical composition to produce a synergistic effect with protein of the invention, or to minimize side effects. Protein that can be administered with IL-1 Hy2 include other IL-1 receptor antagonist polypeptides such as IL-1Ra and IL-1 Hy1 Conversely, protein of the present invention may be included in formulations of the particular cytokine, lymphokine, other hematopoietic factor, thrombolytic or anti-thrombotic factor, or anti-inflammatory agent to minimize side effects of the cytokine, lymphokine, other hematopoietic factor, thrombolytic or anti-thrombotic factor, or anti-inflammatory agent. A protein of the present invention may be active in multimers (e.g., heterodimers or homodimers) or complexes with itself or other proteins. As a result, pharmaceutical compositions of the invention may comprise a protein of the invention in such multimeric or complexed form. Techniques for formulation and administration of the compounds of the instant application may be found in "Remington's Pharmaceutical Sciences," Mack Publishing Co., Easton, Pa., latest edition. A therapeutically effective dose further refers to that amount of the compound sufficient to result in amelioration of symptoms, e.g., treatment, healing, prevention or amelioration of the relevant medical condition, or an increase in rate of treatment, healing, prevention or amelioration of such conditions. When applied to an individual active ingredient, administered alone, a therapeutically effective dose refers to that ingredient alone. When applied to a combination, a therapeutically effective dose refers to combined amounts of the active ingredients that result in the therapeutic effect, whether administered in combination, serially or simultaneously.

In practicing the method of treatment or use of the present invention, a therapeutically effective amount of protein of the present invention is administered to a mammal having a condition to be treated. Protein of the present invention may be administered in accordance with the method of the invention either alone or in combination with other therapies such as treatments employing cytokines, lymphokines or other hematopoietic factors. When co-administered with one or more cytokines, lymphokines or other hematopoietic factors, protein of the present invention may be administered either simultaneously with the cytokine(s), lymphokine(s), other hematopoietic factor(s), thrombolytic or anti-thrombotic factors, or sequentially. If administered sequentially, the attending physician will decide on the appropriate sequence of administering protein of the present invention in combination with cytokine(s), lymphokine(s), other hematopoietic factor(s), thrombolytic or anti-thrombotic factors.

7.6. Routes of Administration

Suitable routes of administration may, for example, include oral, rectal, transmucosal, or intestinal administration; parenteral delivery, including intramuscular, subcutaneous, intramedullary injections, as well as intrathecal, direct intraventricular, intravenous, intraperitoneal, intranasal, or intraocular injections. Administration of protein of the present invention used in the pharmaceutical composition or to practice the method of the present invention can be carried out in a variety of conventional ways, such as oral ingestion, inhalation, topical application or cutaneous, subcutaneous, intraperitoneal, parenteral or intravenous injection. Intravenous administration to the patient is preferred.

Alternately, one may administer the compound in a local rather than systemic manner, for example, via injection of the compound directly into a arthritic joints or in fibrotic tissue, often in a depot or sustained release formulation. In order to prevent the scarring process frequently occurring as complication of glaucoma surgery, the compounds may be administered topically, for example, as eye drops. Furthermore, one may administer the drug in a targeted drug delivery system, for example, in a liposome coated with a specific antibody, targeting, for example, arthritic or fibrotic tissue. The liposomes will be targeted to and taken up selectively by the afflicted tissue.

7.7. Compositions/Formulations

Pharmaceutical compositions for use in accordance with the present invention thus may be formulated in a conventional manner using one or more physiologically acceptable carriers comprising excipients and auxiliaries which facilitate processing of the active compounds into preparations which can be used pharmaceutically. These pharmaceutical compositions may be manufactured in a manner that is itself known, e.g., by means of conventional mixing, dissolving, granulating, dragee-making, levigating, emulsifying, encapsulating, entrapping or lyophilizing processes. Proper formulation is dependent upon the route of administration chosen. When a therapeutically effective amount of protein of the present invention is administered orally, protein of the present invention will be in the form of a tablet, capsule, powder, solution or elixir. When administered in tablet form, the pharmaceutical composition of the invention may additionally contain a solid carrier such as a gelatin or an adjuvant. The tablet, capsule, and powder contain from about 5 to 95% protein of the present invention, and preferably from about 25 to 90% protein of the present invention. When administered in liquid form, a liquid carrier such as water, petroleum, oils of animal or plant origin such as peanut oil, mineral oil, soybean oil, or sesame oil, or synthetic oils may be added. The liquid form of the pharmaceutical composition may further contain physiological saline solution, dextrose or other saccharide solution, or glycols such as ethylene glycol, propylene glycol or polyethylene glycol. When administered in liquid form, the pharmaceutical composition contains from about 0.5 to 90% by weight of protein of the present invention, and preferably from about 1 to 50% protein of the present invention.

When a therapeutically effective amount of protein of the present invention is administered by intravenous, cutaneous or subcutaneous injection, protein of the present invention will be in the form of a pyrogen-free, parenterally acceptable aqueous solution. The preparation of such parenterally acceptable protein solutions, having due regard to pH, isotonicity, stability, and the like, is within the skill in the art. A preferred pharmaceutical composition for intravenous, cutaneous, or subcutaneous injection should contain, in addition to protein of the present invention, an isotonic vehicle such as Sodium Chloride Injection, Ringer's Injection, Dextrose Injection, Dextrose and Sodium Chloride Injection, Lactated Ringer's Injection, or other vehicle as known in the art. The pharmaceutical composition of the present invention may also contain stabilizers, preservatives, buffers, antioxidants, or other additives known to those of skill in the art. For injection, the agents of the invention may be formulated in aqueous solutions, preferably in physiologically compatible buffers such as Hanks's solution, Ringer's solution, or physiological saline buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethylcellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration. For buccal administration, the compositions may take the form of tablets or lozenges formulated in conventional manner.

For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e.g., gelatin for use in an inhaler or insufflator may be formulated containing a powder mix of the compound and a suitable powder base such as lactose or starch. The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

A pharmaceutical carrier for the hydrophobic compounds of the invention is a cosolvent system comprising benzyl alcohol, a nonpolar surfactant, a water-miscible organic polymer, and an aqueous phase. The cosolvent system may be the VPD co-solvent system. VPD is a solution of 3% w/v benzyl alcohol, 8% w/v of the nonpolar surfactant polysorbate 80, and 65% w/v polyethylene glycol 300, made up to volume in absolute ethanol. The VPD co-solvent system (VPD:5W) consists of VPD diluted 1:1 with a 5% dextrose in water solution. This co-solvent system dissolves hydrophobic compounds well, and itself produces low toxicity upon systemic administration. Naturally, the proportions of a co-solvent system may be varied considerably without destroying its solubility and toxicity characteristics. Furthermore, the identity of the co-solvent components may be varied: for example, other low-toxicity nonpolar surfactants may be used instead of polysorbate 80; the fraction size of polyethylene glycol may be varied; other biocompatible polymers may replace polyethylene glycol, e.g. polyvinyl pyrrolidone; and other sugars or polysaccharides may substitute for dextrose. Alternatively, other delivery systems for hydrophobic pharmaceutical compounds may be employed. Liposomes and emulsions are well known examples of delivery vehicles or carriers for hydrophobic drugs. Certain organic solvents such as dimethylsulfoxide also may be employed, although usually at the cost of greater toxicity. Additionally, the compounds may be delivered using a sustained-release system, such as semipermeable matrices of solid hydrophobic polymers containing the therapeutic agent. Various of sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols. Many of the proteinase inhibiting compounds of the invention may be provided as salts with pharmaceutically compatible counterions. Such pharmaceutically acceptable base addition salts are those salts which retain the biological effectiveness and properties of the free acids and which are obtained by reaction with inorganic or organic bases such as sodium hydroxide, magnesium hydroxide, ammonia, trialkylamine, dialkylamine, monoalkylamine, dibasic amino acids, sodium acetate, potassium benzoate, triethanol amine and the like.

The pharmaceutical composition of the invention may be in the form of a complex of the protein(s) of present invention along with protein or peptide antigens. The protein and/or peptide antigen will deliver a stimulatory signal to both B and T lymphocytes. B lymphocytes will respond to antigen through their surface immunoglobulin receptor. T lymphocytes will respond to antigen through the T cell receptor (TCR) following presentation of the antigen by MHC proteins. MHC and structurally related proteins including those encoded by class I and class II MHC genes on host cells will serve to present the peptide antigen(s) to T lymphocytes. The antigen components could also be supplied as purified MHC-peptide complexes alone or with co-stimulatory molecules that can directly signal T cells. Alternatively antibodies able to bind surface immunoglobulin and other molecules on B cells as well as antibodies able to bind the TCR and other molecules on T cells can be combined with the pharmaceutical composition of the invention. The pharmaceutical composition of the invention may be in the form of a liposome in which protein of the present invention is combined, in addition to other pharmaceutically acceptable carriers, with amphipathic agents such as lipids which exist in aggregated form as micelles, insoluble monolayers, liquid crystals, or lamellar layers in aqueous solution. Suitable lipids for liposomal formulation include, without limitation, monoglycerides, diglycerides, sulfatides, lysolecithin, phospholipids, saponin, bile acids, and the like. Preparation of such liposomal formulations is within the level of skill in the art, as disclosed, for example, in U.S. Pat. Nos. 4,235,871; 4,501,728; 4,837,028; and 4,737,323, all of which are incorporated herein by reference.

The amount of protein of the present invention in the pharmaceutical composition of the present invention will depend upon the nature and severity of the condition being treated, and on the nature of prior treatments which the patient has undergone. Ultimately, the attending physician will decide the amount of protein of the present invention with which to treat each individual patient. Initially, the attending physician will administer low doses of protein of the present invention and observe the patient's response. Larger doses of protein of the present invention may be administered until the optimal therapeutic effect is obtained for the patient, and at that point the dosage is not increased further. It is contemplated that the various pharmaceutical compositions used to practice the method of the present invention should contain about 0.01 $\mu$g to about 100 mg (preferably about 0.1 $\mu$g to about 10 mg, more preferably about 0.1 $\mu$g to about 1 mg) of protein of the present invention per kg body weight. For compositions of the present invention which are useful for bone, cartilage, tendon or ligament regeneration, the therapeutic method includes administering the composition topically, systematically, or locally as an implant or device. When administered, the therapeutic composition for use in this invention is, of course, in a pyrogen-free, physiologically acceptable form. Further, the composition may desirably be encapsulated or injected in a viscous form for delivery to the site of bone, cartilage or tissue damage. Topical administration may be suitable for wound healing and tissue repair. Therapeutically useful agents other than a protein of the invention which may also optionally be included in the composition as described above, may alternatively or additionally, be administered simultaneously or sequentially with the composition in the methods of the invention. Preferably for bone and/or cartilage formation, the composition would include a matrix capable of delivering the protein-containing composition to the site of bone and/or cartilage damage, providing a structure for the developing bone and cartilage and optimally capable of being resorbed into the body. Such matrices may be formed of materials presently in use for other implanted medical applications.

The choice of matrix material is based on biocompatibility, biodegradability, mechanical properties, cosmetic appearance and interface properties. The particular application of the compositions will define the appropriate formulation. Potential matrices for the compositions may be biodegradable and chemically defined calcium sulfate, tricalciumphosphate, hydroxyapatite, polylactic acid, polyglycolic acid and polyanhydrides. Other potential materials are biodegradable and biologically well-defined, such as bone or dermal collagen. Further matrices are comprised of pure proteins or extracellular matrix components. Other potential matrices are nonbiodegradable and chemically defined, such as sintered hydroxyapatite, bioglass, aluminates, or other ceramics. Matrices may be comprised of combinations of any of the above mentioned types of material, such as polylactic acid and hydroxyapatite or collagen and tricalciumphosphate. The bioceramics may be altered in composition, such as in calcium-aluminate-phosphate and processing to alter pore size, particle size, particle shape, and biodegradability. Presently preferred is a 50:50 (mole weight) copolymer of lactic acid and glycolic acid in the form of porous particles having diameters ranging from 150 to 800 microns. In some applications, it will be useful to utilize a sequestering agent, such as carboxymethyl cellulose or autologous blood clot, to prevent the protein compositions from disassociating from the matrix.

A preferred family of sequestering agents is cellulosic materials such as alkylcelluloses (including hydroxyalkylcelluloses), including methylcellulose, ethylcellulose, hydroxyethylcellulose, hydroxypropylcellulose, hydroxypropyl-methylcellulose, and carboxymethylcellulose, the most preferred being cationic salts of carboxymethylcellulose (CMC). Other preferred sequestering agents include hyaluronic acid, sodium alginate, poly(ethylene glycol), polyoxyethylene oxide, carboxyvinyl polymer and poly(vinyl alcohol). The amount of sequestering agent useful herein is 0.5–20 wt %, preferably 1–10 wt % based on total formulation weight, which represents the amount necessary to prevent desorbtion of the protein from the polymer matrix and to provide appropriate handling of the composition, yet not so much that the progenitor cells are prevented from infiltrating the matrix, thereby providing the protein the opportunity to assist the osteogenic activity of the progenitor cells. In further compositions, proteins of the invention may be combined with other agents beneficial to the treatment of the bone and/or cartilage defect, wound, or tissue in question. These agents include various growth factors such as epidermal growth factor (EGF), platelet derived growth factor (PDGF), transforming growth factors (TGF-.alpha. and TGF-.beta.), and insulin-like growth factor (IGF).

The therapeutic compositions are also presently valuable for veterinary applications. Particularly domestic animals and thoroughbred horses, in addition to humans, are desired patients for such treatment with proteins of the present invention. The dosage regimen of a protein-containing pharmaceutical composition to be used in tissue regeneration will be determined by the attending physician considering various factors which modify the action of the proteins, e.g., amount of tissue weight desired to be formed, the site of damage, the condition of the damaged tissue, the size of a wound, type of damaged tissue (e.g., bone), the patient's age, sex, and diet, the severity of any infection, time of administration and other clinical factors. The dosage may vary with the type of matrix used in the reconstitution and with inclusion of other proteins in the pharmaceutical composition. For example, the addition of other known growth factors, such as IGF I (insulin like growth factor I), to the final composition, may also effect the dosage. Progress can be monitored by periodic assessment of tissue/bone growth and/or repair, for example, X-rays, histomorphometric determinations and tetracycline labeling.

Polynucleotides of the present invention can also be used for gene therapy. Such polynucleotides can be introduced either in vivo or ex vivo into cells for expression in a mammalian subject. Polynucleotides of the invention may also be administered by other known methods for introduction of nucleic acid into a cell or organism (including, without limitation, in the form of viral vectors or naked DNA). Cells may also be cultured ex vivo in the presence of proteins of the present invention in order to proliferate or to produce a desired effect on or activity in such cells. Treated cells can then be introduced in vivo for therapeutic purposes.

7.8. Effective Dosage

Pharmaceutical compositions suitable for use in the present invention include compositions wherein the active ingredients are contained in an effective amount to achieve its intended purpose. More specifically, a therapeutically effective amount means an amount effective to prevent development of or to alleviate the existing symptoms of the subject being treated. Determination of the effective amounts is well within the capability of those skilled in the art, especially in light of the detailed disclosure provided herein.For any compound used in the method of the invention, the therapeutically effective dose can be estimated initially from cell culture assays. For example, a dose can be formulated in animal models to achieve a circulating concentration range that includes the $IC_{50}$ as determined in cell culture (i.e., the concentration of the test compound which achieves a half-maximal inhibition of the C-proteinase activity). Such information can be used to more accurately determine useful doses in humans.

A therapeutically effective dose refers to that amount of the compound that results in amelioration of symptoms or a prolongation of survival in a patient. Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio between $LD_{50}$ and $ED_{50}$. Compounds which exhibit high therapeutic indices are preferred. The data obtained from these cell culture assays and animal studies can be used in formulating a range of dosage for use in human. The dosage of such compounds lies preferably within a range of circulating concentrations that include the $ED_{50}$ with little or no toxicity. The dosage may vary within this range depending upon the dosage form employed and the route of administration utilized. The exact formulation, route of administration and dosage can be chosen by the individual physician in view of the patient's condition. See, e.g., Fingl et al., 1975, in "The Pharmacological Basis of Therapeutics", Ch. 1 p.1. Dosage amount and interval may be adjusted individually to provide plasma levels of the active moiety which are sufficient to maintain the C-proteinase inhibiting effects, or minimal effective concentration (MEC). The MEC will vary for each compound but can be estimated from in vitro data; for example, the concentration necessary to achieve 50–90% inhibition of the C-proteinase using the assays described herein. Dosages necessary to achieve the MEC will depend on individual characteristics and route of administration. However, HPLC assays or bioassays can be used to determine plasma concentrations.

Dosage intervals can also be determined using MEC value. Compounds should be administered using a regimen which maintains plasma levels above the MEC for 10–90% of the time, preferably between 30–90% and most preferably between 50–90%.In cases of local administration or selective uptake, the effective local concentration of the drug may not be related to plasma concentration.

An exemplary dosage regimen for the human IL-1 Hy2 polypeptides of the invention will be in the range of about 0.01 to 100 mg/kg of body weight daily, with the preferred dose being about 0.1 to 25 mg/kg of patient body weight daily, varying in adults and children. Dosing may be once daily, or equivalent doses may be delivered at longer or shorter intervals.

The amount of composition administered will, of course, be dependent on the subject being treated, on the subject's age and weight, the severity of the affliction, the manner of administration and the judgment of the prescribing physician.

7.9. Packaging

The compositions may, if desired, be presented in a pack or dispenser device which may contain one or more unit dosage forms containing the active ingredient. The pack may, for example, comprise metal or plastic foil, such as a blister pack. The pack or dispenser device may be accompanied by instructions for administration. Compositions comprising a compound of the invention formulated in a compatible pharmaceutical carrier may also be prepared, placed in an appropriate container, and labelled for treatment of an indicated condition.

8. ANTIBODIES

Another aspect of the invention is an antibody that specifically binds the polypeptide of the invention. Such antibodies can be either monoclonal or polyclonal antibodies, as well fragments thereof and humanized forms or fully human forms, such as those produced in transgenic animals. The invention further provides a hybridoma that produces an antibody according to the invention. Antibodies of the invention are useful for detection and/or purification of the polypeptides of the invention.

Protein of the invention may also be used to immunize animals to obtain polyclonal and monoclonal antibodies which specifically react with the protein. Such antibodies may be obtained using either the entire protein or fragments thereof as an immunogen. The peptide immunogens additionally may contain a cysteine residue at the carboxyl terminus, and are conjugated to a hapten such as keyhole limpet hemocyanin (KLH). Methods for synthesizing such peptides are known in the art, for example, as in R. P. Merrifield, J. Amer. Chem. Soc. 85, 2149–2154 (1963); J. L. Krstenansky, et al., FEBS Lett. 211, 10 (1987). Monoclonal antibodies binding to the protein of the invention may be useful diagnostic agents for the immunodetection of the protein. Neutralizing monoclonal antibodies binding to the protein may also be useful therapeutics for both conditions associated with the protein and also in the treatment of some forms of cancer where abnormal expression of the protein is involved. In the case of cancerous cells or leukemic cells, neutralizing monoclonal antibodies against the protein may be useful in detecting and preventing the metastatic spread of the cancerous cells, which may be mediated by the protein. In general, techniques for preparing polyclonal and monoclonal antibodies as well as hybridomas capable of producing the desired antibody are well known in the art (Campbell, A. M., Monoclonal Antibodies Technology: Laboratory Techniques in Biochemistry and Molecular Biology, Elsevier Science Publishers, Amsterdam, The Netherlands (1984); St. Groth et al., J. Immunol. 35:1–21 (1990); Kohler and Milstein, Nature 256:495–497 (1975)), the trioma technique, the human B-cell hybridoma technique (Kozbor et al., Immunology Today 4:72 (1983); Cole et al., in Monoclonal Antibodies and Cancer Therapy, Alan R. Liss, Inc. (1985), pp. 77–96).

Any animal (mouse, rabbit, etc.) which is known to produce antibodies can be immunized with a peptide or polypeptide of the invention. Methods for immunization are well known in the art. Such methods include subcutaneous or intraperitoneal injection of the polypeptide. One skilled in the art will recognize that the amount of the protein encoded by the ORF of the present invention used for immunization will vary based on the animal which is immunized, the antigenicity of the peptide and the site of injection. The protein that is used as an immunogen may be modified or administered in an adjuvant in order to increase the protein's antigenicity. Methods of increasing the antigenicity of a protein are well known in the art and include, but are not limited to, coupling the antigen with a heterologous protein (such as globulin or β-galactosidase) or through the inclusion of an adjuvant during immunization.

For monoclonal antibodies, spleen cells from the immunized animals are removed, fused with myeloma cells, such as SP2/0-Ag14 myeloma cells, and allowed to become monoclonal antibody producing hybridoma cells. Any one of a number of methods well known in the art can be used to identify the hybridoma cell which produces an antibody with the desired characteristics. These include screening the hybridomas with an ELISA assay, western blot analysis, or radioimmunoassay (Lutz et al., Exp. Cell Research. 175:109–124 (1988)).

Hybridomas secreting the desired antibodies are cloned and the class and subclass is determined using procedures known in the art (Campbell, A. M., Monoclonal Antibody Technology: Laboratory Techniques in Biochemistry and Molecular Biology, Elsevier Science Publishers, Amsterdam, The Netherlands (1984)). Techniques described for the production of single chain antibodies (U.S. Pat. No. 4,946,778) can be adapted to produce single chain antibodies to proteins of the present invention.

For polyclonal antibodies, antibody containing antiserum is isolated from the immunized animal and is screened for the presence of antibodies with the desired specificity using one of the above-described procedures. The present invention further provides the above-described antibodies in delectably labeled form. Antibodies can be delectably labeled through the use of radioisotopes, affinity labels (such as biotin, avidin, etc.), enzymatic labels (such as horseradish peroxidase, alkaline phosphatase, etc.) fluorescent labels (such as FITC or rhodamine, etc.), paramagnetic atoms, etc. Procedures for accomplishing such labeling are well-known in the art, for example, see (Sternberger, L. A. et al., J. Histochem. Cytochem. 18:315 (1970); Bayer, E. A. et al., Meth. Enzym. 62:308 (1979); Engval, E. et al., Immunol. 109:129 (1972); Goding, J. W. J. Immunol. Meth. 13:215 (1976)).

The labeled antibodies of the present invention can be used for in vitro, in vivo, and in situ assays to identify cells or tissues in which a fragment of the polypeptide of interest is expressed. The antibodies may also be used directly in therapies or other diagnostics. The present invention further provides the above-described antibodies immobilized on a solid support. Examples of such solid supports include plastics such as polycarbonate, complex carbohydrates such as agarose and sepharose, acrylic resins and such as polyacrylamide and latex beads. Techniques for coupling antibodies to such solid supports are well known in the art (Weir, D. M. et al., "Handbook of Experimental Immunology" 4 th Ed., Blackwell Scientific Publications, Oxford, England, Chapter 10 (1986); Jacoby, W. D. et al., Meth. Enzym. 34 Academic Press, N.Y. (1974)). The immobilized antibodies of the present invention can be used for in vitro, in vivo, and in situ assays as well as for immuno-affinity purification of the proteins of the present invention.

9. COMPUTER READABLE SEQUENCES

In one application of this embodiment, a nucleotide sequence of the present invention can be recorded on computer readable media. As used herein, "computer readable media" refers to any medium which can be read and accessed directly by a computer. Such media include, but are not limited to: magnetic storage media, such as floppy discs, hard disc storage medium, and magnetic tape; optical storage media such as CD-ROM; electrical storage media such as RAM and ROM; and hybrids of these categories such as magnetic/optical storage media. A skilled artisan can readily appreciate how any of the presently known computer readable mediums can be used to create a manufacture comprising computer readable medium having recorded thereon a nucleotide sequence of the present invention. As used herein, "recorded" refers to a process for storing information on computer readable medium. A skilled artisan can readily adopt any of the presently known methods for recording information on computer readable medium to generate manufactures comprising the nucleotide sequence information of the present invention.

A variety of data storage structures are available to a skilled artisan for creating a computer readable medium having recorded thereon a nucleotide sequence of the present invention. The choice of the data storage structure will generally be based on the means chosen to access the stored information. In addition, a variety of data processor programs and formats can be used to store the nucleotide sequence information of the present invention on computer readable medium. The sequence information can be represented in a word processing text file, formatted in commercially-available software such as WordPerfect and Microsoft Word, or represented in the form of an ASCII file, stored in a database application, such as DB2, Sybase, Oracle, or the like. A skilled artisan can readily adapt any number of dataprocessor structuring formats (e.g. text file or database) in order to obtain computer readable medium having recorded thereon the nucleotide sequence information of the present invention. By providing the nucleotide sequence of SEQ ID: 1, 12, 14 or a representative fragment thereof, or a nucleotide sequence at least 99.9% identical to SEQ ID NOS: 1, 12 or 14 in computer readable form, a skilled artisan can routinely access the sequence information for a variety of purposes. Computer software is publicly available which allows a skilled artisan to access sequence information provided in a computer readable medium. The examples which follow demonstrate how software which implements the BLAST (Altschul et al., J. Mol. Biol. 215:403–410 (1990)) and BLAZE (Brutlag et al., Comp. Chem. 17:203–207 (1993)) search algorithms on a Sybase system is used to identify open reading frames (ORFs) within a nucleic acid sequence. Such ORFs may be protein encoding fragments and may be useful in producing commercially important proteins such as enzymes used in fermentation reactions and in the production of commercially useful metabolites.

As used herein, "a computer-based system" refers to the hardware means, software means, and data storage means used to analyze the nucleotide sequence information of the present invention. The minimum hardware means of the computer-based systems of the present invention comprises a central processing unit (CPU), input means, output means, and data storage means. A skilled artisan can readily appreciate that any one of the currently available computer-based systems are suitable for use in the present invention. As stated above, the computer-based systems of the present invention comprise a data storage means having stored therein a nucleotide sequence of the present invention and the necessary hardware means and software means for supporting and implementing a search means. As used herein, "data storage means" refers to memory which can store nucleotide sequence information of the present invention, or a memory access means which can access manufactures having recorded thereon the nucleotide sequence information of the present invention.

As used herein, "search means" refers to one or more programs which are implemented on the computer-based system to compare a target sequence or target structural motif with the sequence information stored within the data storage means. Search means are used to identify fragments or regions of a known sequence which match a particular target sequence or target motif. A variety of known algorithms are disclosed publicly and a variety of commercially available software for conducting search means are and can be used in the computer-based systems of the present invention. Examples of such software includes, but is not limited to, MacPattern (EMBL), BLASTN and BLASTA (NPOLYPEPTIDEIA). A skilled artisan can readily recognize that any one of the available algorithms or implementing software packages for conducting homology searches can be adapted for use in the present computer-based systems. As used herein, a "target sequence" can be any nucleic acid or amino acid sequence of six or more nucleotides or two or more amino acids. A skilled artisan can readily recognize that the longer a target sequence is, the less likely a target sequence will be present as a random occurrence in the database. The most preferred sequence length of a target sequence is from about 10 to 100 amino acids or from about 30 to 300 nucleotide residues. However, it is well recognized that searches for commercially important fragments, such as sequence fragments involved in gene expression and protein processing, may be of shorter length.

As used herein, "a target structural motif," or "target motif," refers to any rationally selected sequence or combination of sequences in which the sequence(s) are chosen based on a three-dimensional configuration which is formed upon the folding of the target motif. There are a variety of target motifs known in the art. Protein target motifs include, but are not limited to, enzyme active sites and signal sequences. Nucleic acid target motifs include, but are not limited to, promoter sequences, hairpin structures and inducible expression elements (protein binding sequences).

10. TRIPLE HELIX FORMATION

In addition, the fragments of the present invention, as broadly described, can be used to control gene expression through triple helix formation or antisense DNA or RNA, both of which methods are based on the binding of a polynucleotide sequence to DNA or RNA. Polynucleotides suitable for use in these methods are usually 20 to 40 bases in length and are designed to be complementary to a region of the gene involved in transcription (triple helix—see Lee et al., Nucl. Acids Res. 6:3073 (1979); Cooney et al., Science 15241:456 (1988); and Dervan et al., Science 251:1360 (1991)) or to the mRNA itself (antisense—Olmno, J. Neurochem. 56:560 (1991); Oligodeoxynucleotides as Antisense Inhibitors of Gene Expression, CRC Press, Boca Raton, Fla. (1988)). Triple helix-formation optimally results in a shut-off of RNA transcription from DNA, while antisense RNA hybridization blocks translation of an mRNA molecule into polypeptide. Both techniques have been demonstrated to be effective in model systems. Information contained in the sequences of the present invention is necessary for the design of an antisense or triple helix oligonucleotide.

11. DIAGNOSTIC ASSAYS AND KITS

The present invention further provides methods to identify the presence or expression of one of the ORFs of the present invention, or homolog thereof, in a test sample, using a nucleic acid probe or antibodies of the present invention.

In general, methods for detecting a polynucleotide of the invention can comprise contacting a sample with a compound that binds to and forms a complex with the polynucleotide for a period sufficient to form the complex, and detecting the complex, so that if a complex is detected, a polynucleotide of the invention is detected in the sample. Such methods can also comprise contacting a sample under stringent hybridization conditions with nucleic acid primers that anneal to a polynucleotide of the invention under such conditions, and amplifying annealed polynucleotides, so that if a polynucleotide is amplified, a polynucleotide of the invention is detected in the sample.

In general, methods for detecting a polypeptide of the invention can comprise contacting a sample with a compound that binds to and forms a complex with the polypeptide for a period sufficient to form the complex, and detecting the complex, so that if a complex is detected, a polypeptide of the invention is detected in the sample. In detail, such methods comprise incubating a test sample with one or more of the antibodies or one or more of nucleic acid probes of the present invention and assaying for binding of the nucleic acid probes or antibodies to components within the test sample.

Conditions for incubating a nucleic acid probe or antibody with a test sample vary. Incubation conditions depend on the format employed in the assay, the detection methods employed, and the type and nature of the nucleic acid probe or antibody used in the assay. One skilled in the art will recognize that any one of the commonly available hybridization, amplification or immunological assay formats can readily be adapted to employ the nucleic acid probes or antibodies of the present invention. Examples of such assays can be found in Chard, T., An Introduction to Radioimmunoassay and Related Techniques, Elsevier Science Publishers, Amsterdam, The Netherlands (1986); Bullock, G. R. et al., Techniques in Immunocytochemistry, Academic Press, Orlando, Fla. Vol. 1 (1982), Vol. 2 (1983), Vol. 3 (1985); Tijssen, P., Practice and Theory of immunoassays: Laboratory Techniques in Biochemistry and Molecular Biology, Elsevier Science Publishers, Amsterdam, The Netherlands (1985). The test samples of the present invention include cells, protein or membrane extracts of cells, or biological fluids such as sputum, blood, serum, plasma, or urine. The test sample used in the above-described method will vary based on the assay format, nature of the detection method and the tissues, cells or extracts used as the sample to be assayed. Methods for preparing protein extracts or membrane extracts of cells are well known in the art and can be readily be adapted in order to obtain a sample which is compatible with the system utilized.

In another embodiment of the present invention, kits are provided which contain the necessary reagents to carry out the assays of the present invention. Specifically, the invention provides a compartment kit to receive, in close confinement, one or more containers which comprises: (a) a first container comprising one of the probes or antibodies of the present invention; and (b) one or more other containers comprising one or more of the following: wash reagents, reagents capable of detecting presence of a bound probe or antibody.

In detail, a compartment kit includes any kit in which reagents are contained in separate containers. Such containers include small glass containers, plastic containers or strips of plastic or paper. Such containers allows one to efficiently transfer reagents from one compartment to another compartment such that the samples and reagents are not cross-contaminated, and the agents or solutions of each container can be added in a quantitative fashion from one compartment to another. Such containers will include a container which will accept the test sample, a container which contains the antibodies used in the assay, containers which contain wash reagents (such as phosphate buffered saline, Tris-buffers, etc.), and containers which contain the reagents used to detect the bound antibody or probe. Types of detection reagents include labeled nucleic acid probes, labeled secondary antibodies, or in the alternative, if the primary antibody is labeled, the enzymatic, or antibody binding reagents which are capable of reacting with the labeled antibody. One skilled in the art will readily recognize that the disclosed probes and antibodies of the present invention can be readily incorporated into one of the established kit formats which are well known in the art.

12. MEDICAL IMAGING

The novel IL-1 Hy2 polypeptides of the invention are useful in medical imaging, e.g., imaging the site of infection, inflammation, and other sites having Interleukin-1 receptor antagonist receptor molecules. See, e.g., Kunkel et al., U.S. Pat. No. 5,413,778. Such methods involve chemical attachment of a labelling agent, administration of the labelled IL-1 Hy2 polypeptide to a subject in a pharmaceutically acceptable carrier, and imaging the labelled IL-1 Hy2 polypeptide in vivo at the target site.

13. SCREENING ASSAYS

Using the isolated proteins and polynucleotides of the invention, the present invention further provides methods of obtaining and identifying agents which bind to a polypeptide encoded by the ORF from a polynucleotide with a sequence of SEQ ID NOS: 1, 12 or 14 to a specific domain of the polypeptide encoded by the nucleic acid, or to a nucleic acid with a sequence of SEQ ID NOS: 1, 12 or 14. In detail, said method comprises the steps of:

(a) contacting an agent with an isolated protein encoded by an ORF of the present invention, or nucleic acid of the invention; and (b) determining whether the agent binds to said protein or said nucleic acid.

In general, therefore, such methods for identifying compounds that bind to a polynucleotide of the invention can comprise contacting a compound with a polynucleotide of the invention for a time sufficient to form a polynucleotide/compound complex, and detecting the complex, so that if a polynucleotide/compound complex is detected, a compound that binds to a polynucleotide of the invention is identified.

Likewise, in general, therefore, such methods for identifying compounds that bind to a polypeptide of the invention can comprise contacting a compound with a polypeptide of the invention for a time sufficient to form a polypeptide/compound complex, and detecting the complex, so that if a polypeptide/compound complex is detected, a compound that binds to a polynucleotide of the invention is identified.

Methods for identifying compounds that bind to a polypeptide of the invention can also comprise contacting a compound with a polypeptide of the invention in a cell for a time sufficient to form a polypeptide/compound complex, wherein the complex drives expression of a receptor gene sequence in the cell, and detecting the complex by detecting reporter gene sequence expression, so that if a polypeptide/compound complex is detected, a compound that binds a polypeptide of the invention is identified.

Compounds identified via such methods can include compounds which modulate the activity of a polypeptide of the invention (that is, increase or decrease its activity, relative to activity observed in the absence of the compound). Alternatively, compounds identified via such methods can include compounds which modulate the expression of a polynucleotide of the invention (that is, increase or decrease expression relative to expression levels observed in the absence of the compound). Compounds, such as compounds identified via the methods of the invention, can be tested using standard assays well known to those of skill in the art for their ability to modulate activity/expression.

The agents screened in the above assay can be, but are not limited to, peptides, carbohydrates, vitamin derivatives, or other pharmaceutical agents. The agents can be selected and screened at random or rationally selected or designed using protein modeling techniques.

For random screening, agents such as peptides, carbohydrates, pharmaceutical agents and the like are selected at random and are assayed for their ability to bind to the protein encoded by the ORF of the present invention. Alternatively, agents may be rationally selected or designed. As used herein, an agent is said to be "rationally selected or designed" when the agent is chosen based on the configuration of the particular protein. For example, one skilled in the art can readily adapt currently available procedures to generate peptides, pharmaceutical agents and the like capable of binding to a specific peptide sequence in order to generate rationally designed antipeptide peptides, for example see Hurby et al., Application of Synthetic Peptides: Antisense Peptides," In Synthetic Peptides, A User's Guide, W. H. Freeman, NY (1992), pp. 289–307, and Kaspczak et al., Biochemistry 28:9230–8 (1989), or pharmaceutical agents, or the like.

In addition to the foregoing, one class of agents of the present invention, as broadly described, can be used to control gene expression through binding to one of the ORFs or EMFs of the present invention. As described above, such agents can be randomly screened or rationally designed/selected. Targeting the ORF or EMF allows a skilled artisan to design sequence specific or element specific agents, modulating the expression of either a single ORF or multiple ORFs which rely on the same EMF for expression control. One class of DNA binding agents are agents which contain base residues which hybridize or form a triple helix formation by binding to DNA or RNA. Such agents can be based on the classic phosphodiester, ribonucleic acid backbone, or can be a variety of sulfhydryl or polymeric derivatives which have base attachment capacity.

Agents suitable for use in these methods usually contain 20 to 40 bases and are designed to be complementary to a region of the gene involved in transcription (triple helix—see Lee et al., Nucl. Acids Res. 6:3073 (1979); Cooney et al., Science 241:456 (1988); and Dervan et al., Science 251:1360 (1991)) or to the mRNA itself (antisense—Okano, J. Neurochem. 56:560 (1991); Oligodeoxynucleotides as Antisense Inhibitors of Gene Expression, CRC Press, Boca Raton, Fla. (1988)). Triple helix-formation optimally results in a shut-off of RNA transcription from DNA, while antisense RNA hybridization blocks translation of an mRNA molecule into polypeptide. Both techniques have been demonstrated to be effective in model systems. Information contained in the sequences of the present invention is necessary for the design of an antisense or triple helix oligonucleotide and other DNA binding agents. Agents which bind to a protein encoded by one of the ORFs of the present invention can be used as a diagnostic agent, in the control of bacterial infection by modulating the activity of the protein encoded by the ORF. Agents which bind to a protein encoded by one of the ORFs of the present invention can be formulated using known techniques to generate a pharmaceutical composition.

14. USE OF NUCLEIC ACIDS AS PROBES

Another aspect of the subject invention is to provide for polypeptide-specific nucleic acid hybridization probes capable of hybridizing with naturally occurring nucleotide sequences. The hybridization probes of the subject invention may be derived from the nucleotide sequence of the SEQ ID NOS: 1, 12 or 14. Because the corresponding gene is only expressed in a limited number of tissues, especially adult tissues, a hybridization probe derived from SEQ ID NOS: 1, 12 or 14 can be used as an indicator of the presence of RNA of cell type of such a tissue in a sample.

Any suitable hybridization technique can be employed, such as, for example, in situ hybridization.PCR as described U.S. Pat. Nos. 4,683,195 and 4,965,188 provides additional uses for oligonucleotides based upon the nucleotide sequences. Such probes used in PCR may be of recombinant origin, may be chemically synthesized, or a mixture of both. The probe will comprise a discrete nucleotide sequence for the detection of identical sequences or a degenerate pool of possible sequences for identification of closely related genomic sequences.

Other means for producing specific hybridization probes for nucleic acids include the cloning of nucleic acid sequences into vectors for the production of mRNA probes. Such vectors are known in the art and are commercially available and may be used to synthesize RNA probes in vitro by means of the addition of the appropriate RNA polymerase as T7 or SP6 RNA polymerase and the appropriate radioactively labeled nucleotides. The nucleotide sequences may be used to construct hybridization probes for mapping their respective genomic sequences. The nucleotide sequence provided herein may be mapped to a chromosome or specific regions of a chromosome using well known genetic and/or chromosomal mapping techniques. These techniques include in situ hybridization, linkage analysis against known chromosomal markers, hybridization screening with libraries or flow-sorted chromosomal preparations specific to known chromosomes, and the like. The technique of fluorescent in situ hybridization of chromosome spreads has been described, among other places, in Verma et al (1988) Human Chromosomes: A Manual of Basic Techniques, Pergamon Press, New York N.Y.

Fluorescent in situ hybridization of chromosomal preparations and other physical chromosome mapping techniques may be correlated with additional genetic map data. Examples of genetic map data can be found in the 1994 Genome Issue of Science (265:1981f). Correlation between the location of a nucleic acid on a physical chromosomal map and a specific disease (or predisposition to a specific disease) may help delimit the region of DNA associated with that genetic disease. The nucleotide sequences of the subject invention may be used to detect differences in gene sequences between normal, carrier or affected individuals.The nucleotide sequence may be used to produce purified polypeptides using well known methods of recombinant DNA technology. Among the many publications that teach methods for the expression of genes after they have been isolated is Goeddel (1990) Gene Expression Technology, Methods and Enzymology, Vol 185, Academic Press, San Diego. Polypeptides may be expressed in a variety of host cells, either prokaryotic or eukaryotic. Host cells may be from the same species from which a particular polypeptide nucleotide sequence was isolated or from a different species. Advantages of producing polypeptides by recombinant DNA technology include obtaining adequate amounts of the protein for purification and the availability of simplified purification procedures.

14.1 Preparation of Sequencing Chips and Arrays

A basic example is using 6-mers attached to 50 micron surfaces to give a chip with dimensions of 3×3 mm which can be combined to give an array of 20×20 cm. Another example is using 9-mer oligonucleotides attached to 10×10 microns surface to create a 9-mer chip, with dimensions of 5×5 mm. 4000 units of such chips may be used to create a 30×30 cm array. In an array in which 4,000 to 16,000 oligochips are arranged into a square array. A plate, or collection of tubes, as also depicted, may be packaged with the array as part of the sequencing kit.

The arrays may be separated physically from each other or by hydrophobic surfaces. One possible way to utilize the hydrophobic strip separation is to use technology such as the Iso-Grid Microbiology System produced by QA Laboratories, Toronto, Canada.

Hydrophobic grid membrane filters (HGMF) have been in use in analytical food microbiology for about a decade where they exhibit unique attractions of extended numerical range and automated counting of colonies. One commercially-available grid is ISO-GRID™ from QA Laboratories Ltd. (Toronto, Canada) which consists of a square (60×60 cm) of polysulfone polymer (Gelman Tuffryn HT-450, 0.45 u pore size) on which is printed a black hydrophobic ink grid consisting of 1600 (40×40) square cells. HGMF have previously been inoculated with bacterial suspensions by vacuum filtration and incubated on the differential or selective media of choice.

Because the microbial growth is confined to grid cells of known position and size on the membrane, the HGMF functions more like an MPN apparatus than a conventional plate or membrane filter. Peterkin et al. (1987) reported that these HGMFs can be used to propagate and store genomic libraries when used with a HGMF replicator. One such instrument replicates growth from each of the 1600 cells of the ISO-GRID and enables many copies of the master HGMF to be made (Peterkin et al., 1987).

Sharpe et al. (1989) also used ISO-GRID HGMF form QA Laboratories and an automated HGMF counter (MI-100 Interpreter) and RP-100 Replicator. They reported a technique for maintaining and screening many microbial cultures.

Peterkin and colleagues later described a method for screening DNA probes using the hydrophobic grid-membrane filter (Peterkin el al., 1989). These authors reported methods for effective colony hybridization directly on HGMFs. Previously, poor results had been obtained due to the low DNA binding capacity of the epoxysulfone polymer on which the HGMFs are printed. However, Peterkin et al. (1989) reported that the binding of DNA to the surface of the membrane was improved by treating the replicated and incubated HGMF with polyethyleneimine, a polycation, prior to contact with DNA. Although this early work uses cellular DNA attachment, and has a different objective to the present invention, the methodology described may be readily adapted for Format 3 SBH.

In order to identify useful sequences rapidly, Peterkin et al. (1989) used radiolabeled plasmid DNA from various clones and tested its specificity against the DNA on the prepared HGMFs. In this way, DNA from recombinant plasmids was rapidly screened by colony hybridization against 100 organisms on HGMF replicates which can be easily and reproducibly prepared.

Manipulation with small (2–3 mm) chips, and parallel execution of thousands of the reactions. The solution of the invention is to keep the chips and the probes in the corresponding arrays. In one example, chips containing 250,000 9-mers are synthesized on a silicon wafer in the form of 8×8 mM plates (15 μM/oligonucleotide, Pease et al., 1994) arrayed in 8×12 format (96 chips) with a 1 mM groove in between. Probes are added either by multichannel pipette or pin array, one probe on one chip. To score all 4000 6-mers, 42 chip arrays have to be used, either using different ones, or by reusing one set of chip arrays several times.

In the above case, using the earlier nomenclature of the application, F=9; P=6; and F+P=15. Chips may have probes of formula BxNn, where x is a number of specified bases B; and n is a number of non-specified bases, so that x–4 to 10 and n=1 to 4. To achieve more efficient hybridization, and to avoid potential influence of any support oligonucleotides, the specified bases can be surrounded by unspecified bases, thus represented by a formula such as (N)nBx(N)m.

14.2 Preparation of Support Bound Oligonucleotides

Oligonucleotides, i.e., small nucleic acid segments, may be readily prepared by, for example, directly synthesizing the oligonucleotide by chemical means, as is commonly practiced using an automated oligonucleotide synthesizer.

Support bound oligonucleotides may be prepared by any of the methods known to those of skill in the art using any suitable support such as glass, polystyrene or Teflon. One strategy is to precisely spot oligonucleotides synthesized by standard synthesizers. Immobilization can be achieved using passive adsorption (Inouye & Hondo, 1990); using UV light (Nagata et al., 1985; Dahlen et al., 1987; Morriey & Collins, 1989) or by covalent binding of base modified DNA (Keller et al., 1988; 1989); all references being specifically incorporated herein.

Another strategy that may be employed is the use of the strong biotin-streptavidin interaction as a linker. For example, Broude et al. (1994) describe the use of Biotinylated probes, although these are duplex probes, that are immobilized on streptavidin-coated magnetic beads. Streptavidin-coated beads may be purchased from Dynal, Oslo. Of course, this same linking chemistry is applicable to coating any surface with streptavidin. Biotinylated probes may be purchased from various sources, such as, e.g., Operon Technologies (Alameda, Calif.).

Nunc Laboratories (Naperville, Ill.) is also selling suitable material that could be used. Nunc Laboratories have developed a method by which DNA can be covalently bound to the microwell surface termed Covalink NH. CovaLink NH is a polystyrene surface grafted with secondary amino groups (>NH) that serve as bridge-heads for further covalent coupling. CovaLink Modules may be purchased from Nunc Laboratories. DNA molecules may be bound to CovaLink exclusively at the 5'-end by a phosphoramidate bond, allowing immobilization of more than 1 pmol of DNA (Rasmussen et al., 1991).

The use of CovaLink NH strips for covalent binding of DNA molecules at the 5'-end has been described (Rasmussen et al., 1991). In this technology, a phosphoramidate bond is employed (Chu et al., 1983). This is beneficial as immobilization using only a single covalent bond is preferred. The phosphoramidate bond joins the DNA to the CovaLink NH secondary amino groups that are positioned at the end of spacer arms covalently grafted onto the polystyrene surface through a 2 nm long spacer arm. To link an oligonucleotide to CovaLink NH via an phosphoramidate bond, the oligonucleotide terminus must have a 5'-end phosphate group. It is, perhaps, even possible for biotin to be covalently bound to CovaLink and then streptavidin used to bind the probes.

More specifically, the linkage method includes dissolving DNA in water (7.5 ng/ul) and denaturing for 10 min. at 95°

C. and cooling on ice for 10 min. Ice-cold 0.1 M 1-methylimidazole, pH 7.0 (1-MeIm$_7$), is then added to a final concentration of 10 mM 1-MeIm$_7$. A ss DNA solution is then dispensed into CovaLink NH strips (75 ul/well) standing on ice.

Carbodiimide 0.2 M 1-ethyl-3-(3-dimethylaminopropyl)-carbodiimide (EDC), dissolved in 10 mM 1-MeIm$_7$, is made fresh and 25 ul added per well. The strips are incubated for 5 hours at 50° C. After incubation the strips are washed using, e.g., Nunc-Immuno Wash; first the wells are washed 3 times, then they are soaked with washing solution for 5 min., and finally they are washed 3 times (where in the washing solution is 0.4 N NaOH, 0.25% SDS heated to 50° C.).

It is contemplated that a further suitable method for use with the present invention is that described in PCT Patent Application WO 90/03382 (Southern & Maskos), incorporated herein by reference. This method of preparing an oligonucleotide bound to a support involves attaching a nucleoside 3'-reagent through the phosphate group by a covalent phosphodiester link to aliphatic hydroxyl groups carried by the support. The oligonucleotide is then synthesized on the supported nucleoside and protecting groups removed from the synthetic oligonucleotide chain under standard conditions that do not cleave the oligonucleotide from the support. Suitable reagents include nucleoside phosphoramidite and nucleoside hydrogen phosphorate.

An on-chip strategy for the preparation of DNA probe for the preparation of DNA probe arrays may be employed. For example, addressable laser-activated photodeprotection may be employed in the chemical synthesis of oligonucleotides directly on a glass surface, as described by Fodor et al. (1991), incorporated herein by reference. Probes may also be immobilized on nylon supports as described by Van Ness et al. (1991); or linked to Teflon using the method of Duncan & Cavalier (1988); all references being specifically incorporated herein.

To link an oligonucleotide to a nylon support, as described by Van Ness et al. (1991), requires activation of the nylon surface via alkylation and selective activation of the 5'-amine of oligonucleotides with cyanuric chloride.

One particular way to prepare support bound oligonucleotides is to utilize the light-generated synthesis described by Pease et al., (1994, incorporated herein by reference).

These authors used current photolithographic techniques to generate arrays of immobilized oligonucleotide probes (DNA chips). These methods, in which light is used to direct the synthesis of oligonucleotide probes in high-density, miniaturized arrays, utilize photolabile 5'-protected N-acyl-deoxynucleoside phosphoramidites, surface linker chemistry and versatile combinatorial synthesis strategies. A matrix of 256 spatially defined oligonucleotide probes may be generated in this manner and then used in the advantageous Format 3 sequencing, as described herein.

14.3 Preparation of Nucleic Acid Fragments

The nucleic acids to be sequenced may be obtained from any appropriate source, such as cDNAs, genomic DNA, chromosomal DNA, microdissected chromosome bands, cosmid or YAC inserts, and RNA, including mRNA without any amplification steps. For example, Sambrook et al. (1989) describes three protocols for the isolation of high molecular weight DNA from mammalian cells (p. 9.14–9.23).

DNA fragments may be prepared as clones in M 13, plasmid or lambda vectors and/or prepared directly from genomic DNA or cDNA by PCR or other amplification methods. Samples may be prepared or dispensed in multi-well plates. About 100–1000 ng of DNA samples may be prepared in 2–500 ml of final volume.

The nucleic acids would then be fragmented by any of the methods known to those of skill in the art including, for example, using restriction enzymes as described at 9.24–9.28 of Sambrook et al (1989), shearing by ultrasound and NaOH treatment.

Low pressure shearing is also appropriate, as described by Schriefer et al. (1990, incorporated herein by reference). In this method, DNA samples are passed through a small French pressure cell at a variety of low to intermediate pressures. A lever device allows controlled application of low to intermediate pressures to the cell. The results of these studies indicate that low-pressure shearing is a useful alternative to sonic and enzymatic DNA fragmentation methods.

One particularly suitable way for fragmenting DNA is contemplated to be that using the two base recognition endonuclease, CviJI, described by Fitzgerald et al. (1992). These authors described an approach for the rapid fragmentation and fractionation of DNA into particular sizes that they contemplated to be suitable for shotgun cloning and sequencing. The present inventor envisions that this will also be particularly useful for generating random, but relatively small, fragments of DNA for use in the present sequencing technology.

The restriction endonuclease CviJI normally cleaves the recognition sequence PuGCPy between the G and C to leave blunt ends. Atypical reaction conditions, which alter the specificity of this enzyme (CviJI), yield a quasi-random distribution of DNA fragments form the small molecule pUC19 (2688 base pairs). Fitzgerald et al. (1992) quantitatively evaluated the randomness of this fragmentation strategy, using a CviJI digest of pUC19 that was size fractionated by a rapid gel filtration method and directly ligated, without end repair, to a lac Z minus M13 cloning vector. Sequence analysis of 76 clones showed that CviJI** restricts pyGCPy and PuGCPu, in addition to PuGCPy sites, and that new sequence data is accumulated at a rate consistent with random fragmentation.

As reported in the literature, advantages of this approach compared to sonication and agarose gel fractionation include: smaller amounts of DNA are required (0.2–0.5 ug instead of 2–5 ug); and fewer steps are involved (no preligation, end repair, chemical extraction, or agarose gel electrophoresis and elution are needed). These advantages are also proposed to be of use when preparing DNA for sequencing by Format 3.

Irrespective of the manner in which the nucleic acid fragments are obtained or prepared, it is important to denature the DNA to give single stranded pieces available for hybridization. This is achieved by incubating the DNA solution for 2–5 minutes at 80–90° C. The solution is then cooled quickly to 2° C. to prevent renaturation of the DNA fragments before they are contacted with the chip. Phosphate groups must also be removed from genomic DNA by methods known in the art.

14.4 Preparation of DNA Arrays

Arrays may be prepared by spotting DNA samples on a support such as a nylon membrane. Spotting may be performed by using arrays of metal pins (the positions of which correspond to an array of wells in a microtiter plate) to repeated by transfer of about 20 nl of a DNA solution to a nylon membrane. By offset printing, a density of dots higher than the density of the wells is achieved. One to 25 dots may be accommodated in 1 mm2, depending on the type of label used. By avoiding spotting in some preselected number of rows and columns, separate subsets (subarrays) may be formed. Samples in one subarray may be the same genomic segment of DNA (or the same gene) from different individuals, or may be different, overlapped genomic clones. Each of the subarrays may represent replica spotting of the same samples. In one example, a selected gene segment may be amplified from 64 patients. For each patient, the amplified gene segment may be in one 96-well plate (all 96 wells containing the same sample). A plate for each of the 64 patients is prepared. By using a 96-pin device, all samples may be spotted on one 8×12 cm membrane. Subarrays may contain 64 samples, one from each patient. Where the 96 subarrays are identical, the dot span may be 1 mm$^2$ and there may be a 1 mm space between subarrays.

Another approach is to use membranes or plates (available from NUNC, Naperville, Ill.) which may be partitioned by physical spacers e.g. a plastic grid molded over the membrane, the grid being similar to the sort of membrane applied to the bottom of multiwell plates, or hydrophobic strips. A fixed physical spacer is not preferred for imaging by exposure to flat phosphor-storage screens or x-ray films.

14.5 Sequence Comparisons

Preferred identity and/or similarity are designed to give the largest match between the sequences tested. Methods to determine identity and similarity are codified in publicly available computer programs including, but are not limited to, the GCG program package, including GAP (Devereux, J., et al., Nucleic Acids Research 12 (1):387 (1984); Genetics Computer Group, University of Wisconsin, Madison, Wis.), BLASTP, BLASTN, BLASTX, and FASTA (Atschul, S. F. et al., J. Molec. Biol. 215:403–410 (1990). The BLAST X program is publicly available from the National Center for Biotechnology Information (NCBI) and other sources (BLAST Manual, Altschul, S., et al. NCB NLM NIH Bethesda, Md. 20894; Altschul, S., et al., J. Mol. Biol. 215:403–410 (1990). The preferred computer program is FASTA version 3, specifically the FASTy program within the FASTA program package. Another preferred algorithm is the well known Smith Waterman algorithm which can also be used to determine identity.

Sequences can be compared to sequences in GenBank using a search algorithm developed by Applied Biosystems and incorporated into the INHERIT™ 670 Sequence Analysis System. In this algorithm, Pattern Specification Language (developed by TRW Inc., Los Angeles, Calif.) is used to determine regions of homology. The three parameters that determine how the sequence comparisons run are window size, window offset, and error tolerance. Using a combination of these three parameters, the DNA database can be searched for sequences containing regions of homology to the query sequence, and the appropriate sequences scored with an initial value. Subsequently, these homologous regions are examined using dot matrix homology plots to distinguish regions of homology from chance matches. Smith-Waterman alignments can be used to display the results of the homology search. Peptide and protein sequence homologies can be ascertained using the INHERT™ 670 Sequence Analysis System in a way similar to that used in DNA sequence homologies. Pattern Specification Language and parameter windows are used to search protein databases for sequences containing regions of homology that were scored with an initial value. Dot-matrix homology plots can be examined to distinguish regions of significant homology from chance matches.

Alternatively, BLAST, which stands for Basic Local Alignment Search Tool, is used to search for local sequence alignments (Altschul S F (1993) J Mol Evol 36:290–300; Altschul, S F et al (1990) J Mol Biol 215:403–10). BLAST produces alignments of both nucleotide and amino acid sequences to determine sequence similarity. Because of the local nature of the alignments, BLAST is especially useful in determining exact matches or in identifying homologs. Whereas it is ideal for matches which do not contain gaps, it is inappropriate for performing motif-style searching. The fundamental unit of BLAST algorithm output is the High-scoring Segment Pair (HSP). An HSP consists of two sequence fragments of arbitrary but equal lengths whose alignment is locally maximal and for which the alignment score meets or exceeds a threshold or cutoff score set by the user. The BLAST approach is to look for HSPs between a query sequence and a database sequence, to evaluate the statistical significance of any matches found, and to report only those matches which satisfy the user-selected threshold of significance. The parameter E establishes the statistically significant threshold for reporting database sequence matches. E is interpreted as the upper bound of the expected frequency of chance occurrence of an HSP (or set of HSPs) within the context of the entire database search.

15. GENE THERAPY

Mutations in the polynucleotides of the invention gene may result in loss of normal function of the encoded protein. The invention thus provides gene therapy to restore normal activity of the polypeptides of the invention; or to treat disease states involving polypeptides of the invention. Delivery of a functional genes encoding polypeptides of the invention to appropriate cells is effected ex vivo, in situ, or in vivo by use of vectors, and more particularly viral vectors (e.g., adenovirus, adeno-associated virus, or a retrovirus), or ex vivo by use of physical DNA transfer methods (e.g., liposomes or chemical treatments). See, for example, Anderson, Nature, supplement to vol. 392, no. 6679, pp. 25–20 (1998). For additional reviews of gene therapy technology see Friedmann, Science, 244:1275–1281 (1989); Verma, Scientific American: 68–84 (1990); and Miller, Nature, 357:455–460 (1992). Introduction of any one of the nucleotides of the present invention or a gene encoding the polypeptides of the present invention can also be accomplished with extrachromosomal substrates (transient expression) or artificial chromosomes (stable expression). Cells may also be cultured ex vivo in the presence of proteins of the present invention in order to proliferate or to produce a desired effect on or activity in such cells. Treated cells can then be introduced in vivo for therapeutic purposes. Alternatively, it is contemplated that in other human disease states, preventing the expression of or inhibiting the activity of polypeptides of the invention will be useful in treating the disease states. It is contemplated that antisense therapy or gene therapy could be applied to negatively regulate the expression of polypeptides of the invention.

Other methods inhibiting expression of a protein include the introduction of antisense molecules to the nucleic acids of the present invention, their complements, or their translated RNA sequences, by methods known in the art, the removal of the nucleic acids of the present invention such as using targeted deletion methods, or the insertion of a negative regulatory element such as a silencer, which is tissue specific. Further, the polypeptides of the present invention can be inhibited by the introduction of antisense molecules that hybridize to nucleic acids that encode for the polypeptides of the present invention and by the removal of a gene that encode for the polypeptides of the present invention.

The present invention still further provides cells genetically engineered in vivo to express the polynucleotides of the invention, wherein such polynucleotides are in operative association with a regulatory sequence heterologous to the host cell which drives expression of the polynucleotides in the cell. These methods can be used to increase or decrease the expression of the polynucleotides of the present invention.

Knowledge of DNA sequences provided by the invention allows for modification of cells to permit, increase, or decrease, expression of endogenous polypeptide. Cells can be modified (e.g., by homologous recombination) to provide increased polypeptide expression by replacing, in whole or in part, the naturally occurring promoter with all or part of a heterologous promoter so that the cells express the protein at higher levels. The heterologous promoter is inserted in such a manner that it is operatively linked to the desired protein encoding sequences. See, for example, PCT International Publication No. WO 94/12650, PCT International Publication No. WO 92/20808, and PCT International Publication No. WO 91/09955. It is also contemplated that, in addition to heterologous promoter DNA, amplifiable marker DNA (e.g., ada, dhfr, and the multifunctional CAD gene which encodes carbamyl phosphate synthase, aspartate transcarbamylase, and dihydroorotase) and/or intron DNA may be inserted along with the heterologous promoter DNA. If linked to the desired protein coding sequence, amplification of the marker DNA by standard selection methods results in co-amplification of the desired protein coding sequences in the cells.

In another embodiment of the present invention, cells and tissues may be engineered to express an endogenous gene comprising the polynucleotides of the invention under the control of inducible regulatory elements, in which case the regulatory sequences of the endogenous gene may be replaced by homologous recombination. As described herein, gene targeting can be used to replace a gene's existing regulatory region with a regulatory sequence isolated from a different gene or a novel regulatory sequence synthesized by genetic engineering methods. Such regulatory sequences may be comprised of promoters, enhancers, scaffold-attachment regions, negative regulatory elements, transcriptional initiation sites, regulatory protein binding sites or combinations of said sequences. Alternatively, sequences which affect the structure or stability of the RNA or protein produced may be replaced, removed, added, or otherwise modified by targeting. These sequence include polyadenylation signals, mRNA stability elements, splice sites, leader sequences for enhancing or modifying transport or secretion properties of the protein, or other sequences which alter or improve the function or stability of protein or RNA molecules.

The targeting event may be a simple insertion of the regulatory sequence, placing the gene under the control of the new regulatory sequence, e.g., inserting a new promoter or enhancer or both upstream of a gene. Alternatively, the targeting event may be a simple deletion of a regulatory element, such as the deletion of a tissue-specific negative regulatory element. Alternatively, the targeting event may replace an existing element; for example, a tissue-specific enhancer can be replaced by an enhancer that has broader or different cell-type specificity than the naturally occurring elements. Here, the naturally occurring sequences are deleted and new sequences are added. In all cases, the identification of the targeting event may be facilitated by the use of one or more selectable marker genes that are contiguous with the targeting DNA, allowing for the selection of cells in which the exogenous DNA has integrated into the cell genome. The identification of the targeting event may also be facilitated by the use of one or more marker genes exhibiting the property of negative selection, such that the negatively selectable marker is linked to the exogenous DNA, but configured such that the negatively selectable marker flanks the targeting sequence, and such that a correct homologous recombination event with sequences in the host cell genome does not result in the stable integration of the negatively selectable marker. Markers useful for this purpose include the Herpes Simplex Virus thymidine kinase (TK) gene or the bacterial xanthine-guanine phosphoribosyl-transferase (gpt) gene.

The gene targeting or gene activation techniques which can be used in accordance with this aspect of the invention are more particularly described in U.S. Pat. No. 5,272,071 to Chappel; U.S. Pat. No. 5,578,461 to Sherwin et al.; International Application No. PCT/US92/09627 (WO93/09222) by Selden et al.; and International Application No. PCT/US90/06436 (WO91/06667) by Skoultchi et al., each of which is incorporated by reference herein in its entirety.

16. TRANSGENIC ANIMALS

In preferred methods to determine biological functions of the polypeptides of the invention in vivo, one or more genes provided by the invention are either over expressed or inactivated in the gern line of animals using homologous recombination [Capecchi, Science 244:1288–1292 (1989)]. Animals in which the gene is over expressed, under the regulatory control of exogenous or endogenous promoter elements, are known as transgenic animals. Animals in which an endogenous gene has been inactivated by homologous recombination are referred to as "knockout" animals. Knockout animals, preferably non-human mammals, can be prepared as described in U.S. Pat. No. 5,557,032, incorporated herein by reference. Transgenic animals are useful to determine the roles polypeptides of the invention play in biological processes, and preferably in disease states. Transgenic animals are useful as model systems to identify compounds that modulate lipid metabolism. Transgenic animals, preferably non-human mammals, are produced using methods as described in U.S. Pat. No 5,489,743 and PCT Publication No. WO94/28 122, incorporated herein by reference.

Transgenic animals can be prepared wherein all or part of a polynucleotides of the invention promoter is either activated or inactivated to alter the level of expression of the polypeptides of the invention. Inactivation can be carried out using homologous recombination methods described above. Activation can be achieved by supplementing or even replacing the homologous promoter to provid for increased protein expression. The homologous promoter can be supplemented by insertion of one or more heterologous enhancer elements known to confer promoter activation in a particular tissue.

The present invention is illustrated in the following examples. Upon consideration of the present disclosure, one of skill in the art will appreciate that many other embodiments and variations may be made in the scope of the present invention. Accordingly, it is intended that the broader aspects of the present invention not be limited to the disclosure of the following examples. Example I addresses cloning of IL-1 Hy2 cDNA, Example 2 addresses identification of polymorphisms, Example 3 addresses tissue expression of IL-1 Hy2 mRNA and polypeptide, Example 4 addresses chromosomal localization of IL-1 Hy2 DNA, Example 5 addresses identification of an IL-1 receptor binding region and binding to IL-1 receptor, Example 6 addresses IL-1 Hy2 polypeptide expression in E. coli, Example 7 addresses confirmation of IL-2 Hy2 biological activities through assessment of its modulating effect on IL-1 related activities and IL-1 related disorders, Example 8 addresses the sequencing of the IL-1 Hy2 human genomic BAC clone, Example 9 addresses the sequencing of IL-1 Hy2 mouse genomic BAC clone, Example 10 addresses inhibition of IL-1β induced IL-6 production by IL-1 Hy2, Example 11 addresses the inhibition of IL-18 activity by IL-1 Hy2, Example 12 addresses IL-1 Hy2 binding to the IL-1 receptor, Example 13 addresses expression of IL-1 Hy2 in mammalian cells.

EXAMPLE 1

Cloning of IL-1 Hy2 cDNA

A plurality of novel nucleic acids were obtained from the FSK001 cDNA library (prepared from human fetal skin tissue mRNA purchased from Invitrogen, San Diego, Calif.) using standard PCR, SBH sequence signature analysis and Sanger sequencing techniques. The inserts of the library were amplified with PCR using primers specific for pSport1 (GIBCO BRL, Grand Island, N.Y) vector sequences which flank the inserts. These samples were spotted onto nylon membranes and interrogated with oligonucleotide probes to give sequence signatures. The clones were clustered into groups of similar or identical sequences, and single representative clones were selected from each group for gel sequencing. The 5' sequence of the amplified inserts was then deduced using the reverse M13 sequencing primer in a typical Sanger sequencing protocol. PCR products were purified and subjected to flourescent dye terminator cycle sequencing. Single pass gel sequencing was done using a 377 Applied Biosystems (ABI) sequencer. One cDNA insert was identified by sequencing of several hundred base pairs (approximately 1–386 of SEQ ID NO: 1) as a novel sequence related to IL-1Ra that had not been previously reported in public databases. The remaining sequence of SEQ ID NO: 1 was obtained by further sequencing of the entire cDNA insert of the same clone; the sequence was confirmed in part by sequencing of 5' RACE PCR products from fetal skin and adult brain cDNA libraries. This sequence and the clone were designated by code name CG149 and clone name RTA00003379F.h.20(later redesignated pIL-1 Hy2 and deposited at the ATCC on May 21, 1999 under Accession No. PTA-96), and the encoded polypeptide was designated IL-1Ra-Hy2 (later redesignated IL-1 Hy2).

EXAMPLE 2

Identification of Polymorphisms

Sequencing of a number of PCR products from various cDNA libraries revealed several potential polymorphisms, which are described with reference to the nucleotide sequence numbering of SEQ ID NO: 1.

At nucleotide 125 of SEQ ID NO: 1, the "T" may be replaced with a "C", resulting in a codon change from "GAT" to "GAC" (a silent mutation, as both codons encode the amino acid Asp). At nucleotide 184 of SEQ ID NO: 1, the "C" may be replaced with a "T", resulting in a codon change from "ACA" (encoding Thr) to "ATA" (encoding Ile). At nucleotide 205 of SEQ ID NO: 1, the "A" may be replaced with a "C", resulting in a codon change from "GAC" (Asp) to "GCC" (Ala). The changes in the amino acid sequence may be reflected in differences in the biological activities of the molecules, which can be confirmed by testing in any of the activity assays described herein.

EXAMPLE 3

Tissue Expression Study 3.1 In Situ Hybridization

Gene expression of human IL-1 Hy2 was analyzed using a semi-quantitative PCR-based technique. A panel of cDNA libraries derived from human tissue (from Clontech and Invitrogen) was screened with IL-2 Hy2 specific primers [5'-CCGCACCAAGGTCCCCATTTTC-3' (nucleotides 206–227), SEQ ID NO: 10 and 3'-GAGCCCACAAGGATAACCCAGG-5' (nucleotides 728–707), SEQ ID NO: 11] to examine the mRNA expression of IL-1 Hy2 in the following human tissues and cell types: heart, kidney, lung, placenta, liver, ovary, lymph node, spleen, testes, thymus, fetal liver, fetal skin, fetal spleen and macrophage. PCR assays (94° C. for 30 sec., 58° C. for 30 sec., 72° C. for 30 sec., for 30 cycles) were performed with 20 ng of cDNA derived from human tissues and cell lines and 10 picomoles of the IL-1 Hy2 gene-specific primers. The 522 bp PCR product was identified through gel electrophoresis. Amplified products were separated on an agarose gel, transfered and chemically linked to a nylon filter. The filter was then hybridized with a radio-actively labeled ($^{33}$ Palpha-dCTP) double-stranded probe generated from the full-length SEQ ID NO: 1 sequence using a Klenow polymerase, random prime method. The filters were washed (high stringency) and used to expose a phosphorimaging screen for several hours. Bands indicated the presence of cDNA including SEQ ID NO: 1 sequences in a specific library, and thus mRNA expression in the corresponding cell type or tissue.

IL-1 Hy2 mRNA was observed to be expressed in kidney, spleen, and fetal skin. Similar to IL-1 Hy2, IL-1Ra and IL-1 Hy1 mRNA are also expressed in the human fetal skin tissues, suggesting that this family of proteins may share some physiologic functions.

Additional studies were performed to localize IL-1 Hy2 mRNA expression as described by D'Andrea et al. (J. Sur. Path, 1:191–203,1995). IL-1 Hy2 mRNA was detected in serial sections of human normal tonsil and kidney by DIG-labeled probes consisting of nucleotide 396 to 568 of SEQ ID NO: 14. The slides were hybridized with the IL-1 Hy2 probes for 2 hours at 54° C. Subsequently, the slides were washed with 2×SSC at room temperature and then washed with 01×SSC at 54° C. After the stringency rinses, 5-bromo-4-chloro-3-indolyl phosphate/nitro blue tetrazolium (BCIP/NBT) was used a chromagen. For visual detection, the slides were counter-stained with Eosin and examined under a light microscope.

3.2 Immunohistochemistry

The serial sections of normal tonsil were also stained with polyclonal antibodies specific for IL-1 Hy2 prepared by immunizing rabbits with IL-1 Hy2 peptide: 43–56 of SEQ. ID NO.: 2 using conventional methods [see, e.g. Harlow et al., "Antibodies: A Laboratory Manual". Cold Spring Harbor Laboratories, Cold Spring Harbor, N.Y. (1998)] and control preimmune serum form the immunized rabbits. In addition, the slides were stained with antibodies for CD20, Ki67, CD3, CD1a, CD14, CD68 and LN5. Antibody binding was detected with biotinylated secondary antibodies and streptavidin-HRP. AEC Haishen was used as the chromagen for detection and the slides were counter-stained with hema-toxylin. IL-1 Hy2 expression was visually detected under a light microscope.

IL-1 Hy2 mRNA was detected it the distal tubules of the kidney, the glomeruli of the kidney, the Bowman's capsule epithelia, capillary epithelia, and a subset of white blood cells within the blood vessels. In the tonsil, IL-1 Hy2 mRNA and protein were detected in a subset of B-cells (CD20 positive) in the germinal center, most of which were proliferating according to Ki67 staining. IL-1 Hy2 was also expressed in the basal squamous epithelial of the skin surrounding the tonsil.

EXAMPLE 4

Chromosomal Localization Study

Chromosome mapping technologies allow investigators to link genes to specific regions of chromosomes. Chromosomal mapping was performed using the NIGMS human/rodent somatic cell hybrid mapping panel as described by Drwinga, H. L. et al., Genomics, 16, 311–314, 1993 (human/rodent somatic cell hybrid mapping panel #2 purchased from the Coriell Institute for Medical Research, Camden, N.J.). 60 ng of DNA from each sample in the panel was used as template, and 10 picomoles of the same IL-1 Hy2 gene-specific oligonucleotides used in Example 3 were used as primers in a PCR assay (94° C. for 30 sec., 58° C. for 30 sec., 72° C. for 30 sec., for 30 cycles). PCR products were analyzed by gel electrophoresis. The 800 bp genomic PCR product was detected only in the human/rodent somatic cell hybrid DNA containing human chromosome 2.

Gene family members are often linked to specific regions of chromosomes owing to intrachromosomal gene duplication events that give rise to multimember gene families during the process of evolution. The interleukin-1 gene family has been mapped to chromosome 2. More specifically, all of the interleukin 1 genes (IL-1α, IL-1β) and the receptors (IL-1RI and IL-1 RII), as well as the receptor antagonist IL-1ra and the newly identified IL-1 Hy2 have been found to be situated in chromosome 2. The identification of IL-1 Hy2 sequences in this same region establishes its physical linkage to the interleukin-1 locus which indicates that IL-1 Hy2 functions as a modulator of the inflammatory response.

EXAMPLE 5

Interleukin-1 Receptor Binding Domain and Interleukin-1 Receptor Assay The receptor binding region of both IL-1β and IL-1Ra have been mapped to an 18 amino acid region in the carboxy terminal half of the proteins (i.e., residues 88–105 of IL-1β) by site-directed mutagenesis and protein modification studies.

IL-1 Hy2 and fragments thereof that include a receptor binding region are useful as reagents to identify cells and tissues expressing IL-1 receptors. The IL-1 receptor binding assay described in Hannum et al. Nature 343:336–340 (1990) may be used. Briefly, highly radioactive recombinant SEQ ID NOS: 2 or 4 is prepared by growing E. coli expressing either of SEQ ID NOS: 2 or 4 on M9 medium containing $^{3}$S-sulfate and purifying the labeled recombinant polypeptide by chromatography on a Mono-S column. The labeled polypeptide is incubated with the cells or tissue under standard IL-1 binding assay conditions, and $^{35}$S binding. Significant $^{35}$S binding indicates the presence of IL-1 receptors.

EXAMPLE 6

Expression of IL-1 Hy2 in E. Coli

SEQ ID NOS: 1, 12 or 14 are expressed in E. coli by subcloning the entire coding region into a prokaryotic expression vector. The expression vector (pQE16) used is from the QIAexpression prokaryotic protein expression system (Qiagen). The features of this vector that make it useful for protein expression include: an efficient promoter (phage T5) to drive transcription; expression control provided by the lac operator system, which can be induced by addition of IPTG (isopropyl-β-D-thiogalactopyranoside), and an encoded His$_6$ tag. The latter is a stretch of 6 histidine amino acid residues which can bind very tightly to a nickel atom. The vector can be used to express a recombinant protein with a His$_6$ tag fused to its carboxyl terminus, allowing rapid and efficient purification using Ni-coupled affinity columns.

PCR is used to amplify the coding region which is then ligated into digested pQE16 vector. The ligation product is transformed by electroporation into electrocompetent E.coli cells (strain M15[pREP4] from Qiagen), and the transformed cells are plated on ampicillin-containing plates. Colonies are screened for the correct insert in the proper orientation using a PCR reaction employing a gene-specific primer and a vector-specific primer. Positives are then sequenced to ensure correct orientation and sequence. To express IL-1 Hy2, a colony containing a correct recombinant clone is inoculated into L-Broth containing 100 μg/ml of ampicillin, 25 μg/ml of kanamycin, and the culture was allowed to grow overnight at 37° C. The saturated culture is then diluted 20-fold in the same medium and allowed to grow to an optical density at 600 nm of 0.5. At this point, IPTG is added to a final concentration of 1 mM to induce protein expression. The culture is allowed to grow for 5 more hours, and then the cells are harvested by centrifugation at 3000×g for 15 minutes.

The resultant pellet is lysed using a mild, nonionic detergent in 20 mM Tris HCl (pH 7.5) (B-PERTm Reagent from Pierce), or by sonication until the turbid cell suspension turned translucent. The lysate obtained is further purified using a nickel containing column (Ni-NTA spin column from Qiagen) under non-denaturing conditions. Briefly, the lysate is brought up to 300 mM NaCl and 10 mM imidazole and centrifuged at 700×g through the spin column to allow the His-tagged recombinant protein to bind to the nickel column. The column is then washed twice with Wash Buffer (50 mM NaH$_2$PO$_4$, pH8.0; 3000 mM NaCl; 20 mM imidazole) and is eluted with Elution Buffer (50 mM NaH$_2$PO$_4$, pH8.0; 300 mM NaCl; 250 mM imidazole). All the above procedures are performed at 4° C. The presence of a purified protein of the predicted size is confirmed with SDS-PAGE.

EXAMPLE 7

Evaluation of IL-1 Hy2 Activities In Vitro and In Vivo 7.1 Binding to the Interleukin-1 Receptor A cell binding assay is carried out to demonstrate that IL-1 Hy2 binds to the Interleukin-1 receptor. Briefly, cell binding of the recombinant protein with and without the presence of 100-fold greater amounts of non tagged Interleukin-1 Beta (IL-1β) ligand is analyzed by using fluorescent antibodies specific for a IL-1 Hy2 polypeptide (e.g. specific for an express tag within the recombinant polypeptide) on the fluorescent activated cell sorter (FACS). In each reaction, 106 cells NHDF (normal human dermal fibroblasts) are resuspended in 100 μl of FACS buffer (distilled PBS and 3% calf serum and 0.01% azide). Cell binding is done by adding 5 nM recombinant IL-1 Hy2 in 100 μl cell suspension and as a competition in one reaction, 500 nM of recombinant IL-1β is also added. The cells are incubated on ice for 1 hr.

The cells are pelleted, 200 μl of 0.2 mM BS3 (crosslinker) is added, and the cells are kept on ice for 30 min. Next, 10 μl 1 M Tris pH 7.5 is added and the cells are incubated for 15 minutes on ice. The cells are pelleted, washed 1 time in FACS buffer, resuspended in 100 μl volume of FACS buffer and 2 μl primary antibody (anti-express tag antibody 1 mg/ml) is added, and incubated on ice for 30 minutes. The cells are pelleted, washed with FACS buffer, and resuspended in FACS buffer (100 μl volume). The secondary antibody (phycoerythrin conjugated) 2 μl of anti-mouse Ig (1 mg/ml) is added and the cells are incubated for 30 minutes on ice. The cells are again pelleted, washed two times with FACS buffer, resuspended in 0.5 ml FACS buffer and analyzed on FACS. A shift in the fluorescence is expected to be observed in the cells treated with the recombinant tagged IL-1 Hy2. This binding is shown to be specific if it is competed off with the non tagged IL-1β protein. The results will indicate binding of IL-1 Hy2 to the IL-1 receptor.

7.2 IL-1 Antagonist Activity

IL-1 antagonist activity is determined using a prostaglandin E2 ($PGE_2$) based assay as follows. Cells are plated at 20,000 cells per well in a 96 well plate 24 hours before the assay. The cells are then treated with 25 pg/ml recombinant human IL-1β for 7 hours. To evaluate inhibition of IL-1 stimulated $PGE_2$ release by IL-1 Hy2 in comparison to IL-1Ra, the cells are pretreated with various amounts of IL-1 Hy2 or IL-1Ra for two hours before the addition of IL-1β. The supernatants are then collected and cell debris is removed by centrifugation. The amounts of $PGE_2$ in the supernatants are determined by ELISA using the $PGE_2$ assay system (R&D Systems) according to the manufacturer's protocol.

This assay was carried out with IL-1 Hy2 as follows. To stimulate IL-1β induced $PGE_2$ production, human fibroblasts (CCD 1098; accession no. CRL 2127) were plated at 20,000 cells per well in a 96 well plate 24 hours before the assay. The cells were then washed once with fresh media and incubated for 16 hours with fresh media containing 1 ng/ml recombinant human IL-1β. To evaluate inhibition of IL-1β stimulated $PGE_2$ release by IL-1 Hy2 in comparison to IL-1Ra, the cells were treated with various concentrations of IL-1 Hy2 or IL-1Ra together with IL-1β. After the 16 hour stimulation at 37° C. in a 5% $CO_2$ incubator, the culture plates were centrifuged for 5 minutes at 4000 rpm to remove cellular debris. The amounts of $PGE_2$ were determined by assaying 100 μl of supernatant with the $PGE_2$ ELISA assay kit (R & D Systems) according to the manufacturer's protocol.

The addition of L-1 Hy2 to the IL-1β stimulated cultures resulted in a dose-dependent partial decrease in $PGE_2$ production. At a concentration of 1000 fold excess, IL-1 Hy2 inhibited IL-1β induced PGE2 production 40–60%. As a control and a means for comparison, IL-1Ra completely inhibited $PGE_2$ production at a concentration of 100 fold excess. The fact that L-1 Hy2 only partially inhibits IL-1β activity may be beneficial in the treatment of inflammatory disease states due to fewer side effects. It is possible that more highly purified preparations of IL-2 Hyl may show complete inhibition in this assay.

7.3 Inhibition of Interleukin-1 Induced Cell Proliferation

Murine D10 T cells are obtained from the American Type Culture Collection (Rockville, Md.). Cells are maintained in Dulbecco's modified Eagle medium and Ham's F-12 medium (1:1) containing 10 mM HEPES buffer (pH 7.4) and 10% fetal bovine serum. All tissue culture reagents contained less than 0.25 ng/mL endotoxin as measured by the limulus amebocyte assay.

Murine D10 cells, an Interleukin-1 dependent T-cell line, are used to measure Interleukin-1 mitogenic activity. Cell proliferation in the present of Interleukin-1 with and without the IL-1 Hy2 polypeptides of the invention is assessed by incorporation of ($^3H$) thymidine as previously described (Bakouche, O., et al. J. Immunol. 138:4249–4255, 1987). In a preferred embodiment, antagonists and agonist of the IL-1 Hy2 polypeptides of the invention are identified in this assay by adding the candidate compounds with the Interleukin-1 and IL-1 Hy2 polypeptides of the invention and measuring the change in cell proliferation caused by the candidate compound.

7.4 Inhibition of Interleukin-1 Induced Cell Cytotoxicity

Inhibition of Interleukin-1-induced cytotoxicity is studied using an appropriate cell line, such as, for example, A375 tumor cells plated at a density of 6000 cells per well in 96-well microliter plates. After overnight attachment, Interleukin-1 (3–300 ng/mL) is added in the presence or absence of NAA or NMA. After cells are incubated for 3 days, ($^3H$) thymidine is added (1 mu Ci per well) for an additional 2 hours. Cells are harvested onto glass fiber disks (PHD Cell Harvested; Cambridge Technology, Inc., Watertown, Mass.) Disks are air dried overnight, and radioactivity is determined with a Model 1900TR Scintillation Counter (Packard Instrument Division, Downers Grove, Ill.).

7.5 Induction Of Nitrite Synthesis In Smooth Muscle Cells

Aortic smooth muscle cells are cultured by explanting segments of the medial layer of aortas from adult male Fischer 344 rats. Aortas are removed aseptically and freed of adventitial and endothelial cells by scraping both the luminal and abluminal surfaces. Medial fragments are allowed to attach to Primaria 25-$cm^2$ tissue culture flasks (Becton-Dickinson, Lincoln Park, N.J.) which are kept moist with growth medium until cells emerged. Cultures are fed twice weekly with medium 199 containing 10% fetal bovine serum, 25 mM HEPES buffer (pH 7.4), 2 mM L-glutamine, 40 mu g/mL endothelial cell growth supplement (Biomedical Technologies, Inc., Stoughton, Mass.) and 10 mu g/ml gentamicin (GIBCO BRL, Grand Island, N.Y.). When primary cultures become confluent, they are passaged by trypsinization, and explants are discarded. For these studies, cells from passages 12–14 are seeded at 20,000 per well in 96-well plates and are used at confluence (60,000–80,000 cells per well). The cells exhibit the classic smooth muscle cell phenotype with hill and valley morphology, and they stain positively for smooth muscle actin.

Rat aortic smooth muscle cells are incubated with RPMI-1640 medium containing 10% bovine calf serum, 25 mM HEPES buffer (pH 7.4), 2 mM glutamine, 80 mu g/mL penicillin, 80 mu g/mL steptomycin, 2 mu g/mL fungizone, 30 mu g/mL lipopolysaccharide (*Escherichia coli* 0111:B4), and 50 U/mL IFN-γ. Cells are harvested after 24 hours, and cytosol is prepared (Gross, S. S., et al. Biochem. Biophys. Res. Commun. 178:823–829, 1991). Cytosolic NO synthase activity is assayed by the $Fe^{2+}$-myoglobin method described previously (Gross, S. S., et al. Biochem. Biophys. Res. Commun. 178:823–829, 1991).

Rat aortic smooth muscle cells are incubated with RPMI-1640 medium containing 10% bovine calf serum, 25 mM HEPES buffer (pH 7.4), 2 mM glutamine, 80 mu g/mL penicillin, 80 mu g/mL steptomycin, 2 mu g/mL fungizone, 30 mu g/mL lipopolysaccharide (*Escherichia coli* 0111:B4), and 50 U/mL IFN-y. Cells are harvested after 24 hours, and cytosol is prepared (Gross, S. S., et al. Biochem. Biophys. Res. Commun. 178:823–829, 1991). Cytosolic NO synthase activity is assayed by the Fe sup 2+-myoglobin method described previously (Gross, S. S., et al. Biochem. Biophys. Res. Commun. 178:823–829, 1991).

7.6 Alloreactivity Determined by Lymph Node Weight Gain

Experiments are conducted to show that systemic administration of the IL-1 Hy2 polypeptides of the invention suppress a localized, T cell-dependent, immune response to alloantigen presented by allogeneic cells. Mice are injected in the footpad with irradiated, allogeneic spleen cells. The mice are then injected in the contralateral footpad with irradiated, syngeneic spleen cells. An alloreactive response (marked by proliferation of lymphocytes and inflammation) occurs in the footpad receiving the allogeneic cells, which can be measured by determining the increase in size and weight of the popliteal lymph node draining the site of antigen deposition relative to controls or by an increase in cellularity.

Specific pathogen free 8–12 week old BALB/c (H-2 sup d) and C57 BL/6 (H-2 sup b) mice (Jackson Laboratory, Bar Harbor, Me.) are used in this experiment. 48 BALB/c mice are divided into 16 groups, each having 3 mice (unless otherwise indicated). Each group of mice received a different mode of treatment. On day 0 the left footpads of all mice are injected intracutaneously with 107 irradiated (2500R), allogeneic spleen cells from C57BL/6 mice in 50 µl of RPMI-1640 (Gibco) as antigen and the right contralateral footpads of the same mice are injected with 10 sup 7 irradiated (2500R), syngeneic spleen cells from BALB/c mice.

Seven days after antigen administration, the mice are sacrificed and the popliteal lymph nodes (PLN) are removed from the right and left popliteal fossa by surgical dissection. Lymph nodes are weighed and the results expressed as the difference (DELTA) in weight (mg) of the lymph node draining the site of allogeneic cell injection and the weight of the node draining the syngeneic cell injection site. Lymph nodes draining the syngeneic cell injection site weighed approximately 1 mg, regardless of whether they are obtained from mice treated with MSA or IL-1 Hy2 polypeptides of the invention, and did not differ significantly in weight from nodes obtained from mice given no cell injection.

7.7 Suppression Of Organ Graft Rejection In Vivo

Neonatal C57BL/6 (H-2 sup b) hearts are transplanted into the ear pinnae of adult BALB/c (H-2 sup d) recipients utilizing the method of Fulmer et al., Am. J. Anat. 113:273, 1963, modified as described by Trager et al., Transplantation 47:587, 1989, and Van Buren et al., Transplant. Proc. 15:2967, 1983. Survival of the transplanted hearts is assessed by visually inspecting the grafts for pulsatile activity. Pulsatile activity is determined by examining the ear-heart grafts of anesthetized recipients under a dissecting microscope with soft reflected light beginning on day 5 or 6 post transplant. The time of graft rejection is defined as the day after transplantation on which contractile activity ceases.

Recipient mice are transplanted on day 0 and injected with either IL-1 Hy2 polypeptides of the invention plus MSA (mouse serum albumin, 100 ng) or with MSA alone on days 0 through 6, alternating i.p. and s.c. routes. In a second heart transplant experiment, the mice are injected with MSA alone on days 0 through 2, i.p. route only.

7.8 Suppression of Inflammatory Arthritis 20 rats are divided into 4 groups, designated Groups G–J, each having 5 rats. All rats are immunized by subcutaneous injection. On day 21 following immunization with mBSA, an inflammatory arthritis response is elicited. On the same day, a negative control group is injected with a 0.2 ml volume of saline. Groups are injected with increasing amounts of IL-1 Hy2 polypeptides of the invention. Interleukin-1 is injected in one group as a positive control. The diameter of the largest egion of the treated joints is measured using a caliper on days 2, 4, 6 and 8 relative to day 0 intra-articular injection of antigen.

7.9 Activity in a Pancreatitis Model

Acute edematous, necrotizing pancreatitis is induced in adult male Swiss mice weighing more than 35 grams using caerulein—an analog of cholecystokinin. Mice are divided into four groups with three of the groups receiving caerulein 50 mu g/kg by intraperitoneal (IP) injection in four doses over three hours as previously described. (Murayama et al., Arch Surg 1990;125:1570–1572; Tani et al., International J Pancreatology 1987;2:337–348; Schoenberg et al., Free Radical Biology & Medicine 1992;12:515–522; Heath et al., Pancreas 1993;66:41–45; Saluja et al., Amer Physiological Society 1985: G702-G710; Manso et al., Digestive Disease and Sciences 1992;37:364–368). Group 1 is a control group (n-9) which receives only IP saline injections. Group 2 (n=12) is an untreated disease control. Group 3 (n=12) receives three injections of drug (10 mg/kg/hr) starting one hour prior to induction of pancreatitis. Group 4 (n=12) receives three injections of drug (10 mg/kg/hr) starting one hour after induction of pancreatitis.

After a suitable time period, all animals are euthanized, the blood collected, and the pancreata surgically excised and weighed. Serum is assayed for amylase, lipase, IL-6, and TNF levels. Each pancreas is fixed, stained, and graded histologically in a blinded fashion or interstitial edema, granulocyte infiltration, acinar vacuolization, and acinar cell. Additionally, serum levels of IL-1 Hy2 are determined, therefore allowing comparisons between dosage, serum level, systemic cytokine response, and degree of pancreatic damage.

Interleukin-6, Interleukin-1, Interleukin-1 receptor antagonist, and TNF are measured by commercially available ELISA kits (Genzyme Corp., Boston, Mass.). All specimens are run in triplicate. Serum levels of amylase and lipase are measured on a Kodak Ectachem 700 automated analyzer (Eastman Kodak Company, Rochester, N.Y.).

Histologic slides are prepared as is known in the art after rapid excision and subsequent fixation in 10% formalin. The tissues are paraffin embedded as is known in the art and then stained with Hematoxylin and Eosin in a standard fashion. These slides are examined and graded in a blinded fashion by a board certified pathologist.

EXAMPLE 8

Sequencing of IL-1 Hy2 Human Genomic BAC Clone

To understand the genomic organization of the IL-1 Hy2 gene, a commercial human BAC library (Research Genetics) was screened with the full length IL-1 Hy2 cDNA using standard procedures. The BAC clone containing the human genomic IL-1 Hy2 gene was sequenced by conventional methods and is set forth as SEQ ID NO: 15. Based on the sequences, exons of the IL-1 Hy2 gene were predicted using the GenScan software (Stanford University). This analysis indicated that the IL-1 Hy2 cDNA should contain additional sequences at the 5' end in addition to those set forth in SEQ ID NO: 1.

The predicted cDNA sequence based on the genomic DNA sequence encoding IL-1 Hy2 was compared to the corresponding cDNA sequence. This analysis indicated that the predicted cDNA sequence based on the human genomic sequence of IL-1 Hy2 (SEQ ID NO: 12) contains a thyrnidine (T) at nucleotide 279 (see FIG. 2), while the IL-1 Hy2 cDNA sequence (SEQ ID NO: 14; FIG. 4) contains a cytosine (C) at position 279. The change in nucleotides (C→T) would extend the IL-1 Hy2 open reading frame in the 5' direction, resulting in a 200 amino acid polypeptide, while the cDNA sequence (SEQ ID NO: 14; FIG. 4) encodes a 152 amino acid polypeptide (SEQ ID NO: 2).

The predicted cDNA sequence (SEQ ID NO: 12) is 1366 nucleotides which contains an open reading frame (nucleotides 278 to 880) that encodes a predicted polypeptide of 200 amino acids (SEQ ID NO: 13; FIG. 2). However, the sequences surrounding the translation initiation codon at nucleotide 422 of SEQ ID NO: 12 are more similar to the Kozak translation start site consensus than the sequences surrounding nucleotide 278. Therefore, it is also possible that the IL-1 Hy2 polypeptide is encoded by a shorter open reading frame between nucleotides 422 and 880 of SEQ ID NO: 12, which encodes a predicted polypeptide of 152 amino acid (SEQ ID NO: 2).

EXAMPLE 9

Sequencing of IL-1 Hy2 Mouse Genomic BAC Clone

A commercial mouse BAC library (Research Genetics) was screened with the full length IL-1 Hy2 cDNA using standard procedures. The BAC clone containing the mouse IL-1 Hy2 gene was sequenced by conventional methods and is set forth as SEQ ID NO: 17. Based on the sequences, exons of the mouse IL-1 Hy2 gene were predicted using the GenScan software (Stanford University). This analysis indicated that the mouse IL-1 Hy2 gene contains 4 exons. The predicted cDNA encoding the mouse IL-1 Hy protein is set forth as SEQ ID NO: 16. The murine IL-1 Hy2 polypeptide translation initiates at nucleotide 1 and terminates at nucleotide 457 of SEQ ID NO: 17. The mouse and human IL-1 Hy2 polypeptide sequences share 81.7% homology. The murine genomic DNA sequence can be used to generate transgenic animals which overexpress the IL-1 Hy2 polypeptide or have the IL-1 Hy2 gene knocked out as described above in Section 16.

EXAMPLE 10

Inhibition of IL-1β Induced IL-6 Production

Inhibition of Interleukin-1β induced IL-6 production was studied using human endothelial cells from umbilical vein (Huvec). Huvec cells were seeded at $2\times10^4$ cells per well in a 96-well plate the day before cell stimulation. On the day of stimulation, cells were washed once with fresh medium (F12 medium with 100 μg/ml heparin, 50 μg/ml endothelial growth supplement and 10% fetal bovine serum) and replated with 200 μl of fresh medium [without supplements] in each well. The Huvec cells were then stimulated with 100 pg/ml (final volume) of IL-1β. Although this assay was done with IL-1β, any cytokine of interest can be used. To test IL-6 inhibition, different concentrations of IL-1 Hy2 (ranging from 10× to 1000× the concentration of IL-1β) or IL-1ra (ranging from 10× to 1000× IL-1β concentration) were added to the wells with the IL-1β.

After 16 hours of cell stimulation, the culture plate was spun for five minutes at 4000 rpm to remove cell debris. To test for the presence of IL-6, 100 μl of supernatant was removed and assayed with a human IL-6 immunoassay kit (R&D Systems) according to the manufacturer's instructions.

IL-1 Hy2 partially inhibited IL-2β-stimulated IL-6 production in a dose-dependent manner. In view of the fact that L-6 blocks production of tumor necrosis factor (TNF), a pro-inflammatory cytokine, the fact that IL-2 Hy2 only partially inhibits of IL-6 production by IL-1 Hy2 may be beneficial in the treatment of inflammatory disease states with IL-1 Hy2 due to reduced side effects. It is possible that more highly purified preparations of IL-1 Hy2 may show complete inhibition in this assay.

EXAMPLE 11

Inhibition of IL-18 Activity by IL-1 Hy2

The following experiment evaluated the ability of IL-2 Hy2 to inhibit IL-18 activity, as measured by induction of IFN-γ. Human lymphocytes (PBMC) were obtained by Ficoll-Hypaque density gradient separation of peripheral blood from healthy volunteer donors. Immediately after isolation, the PBMC were washed two times with growth media, containing RPMI 1640–10% fetal bovine serum, and $3\times10^5$ cells/well were seeded in a 96 well plate. The cells were stimulated by adding anti-CD3 antibody (R & D Systems, Minneapolis, Minn.) to all of the samples at a final concentration of 0.5 μg/ml. At the time of stimulation, all but one control well per plate were treated with 100 ng/ml recombinant IL-18 (R&D Systems) for 36 hours at 37° C. at 5% $CO_2$. The untreated well served as a measure of background levels of IFNγ produced by stimulated PBMC cells. IL-18 treatment causes the PBMC cells to increase production of IFN-γ relative to the background levels.

To assay for IL-1 Hy2 inhibition of IL-18 stimulated IFNγ production, 100× fold to 1000× fold concentration of IL-1 Hy2 (relative to IL-18 concentration) was added to wells together with IL-18 at the time of stimulation. After 36 hours of cell stimulation, the culture plate was centrifuged for 5 minutes at 4000 rpm to remove cell debris. The supernatant was assayed for IFNγ using the Quantikine ILFNγ ELISA kit (R & D Systems) according to the manufacturer's suggested protocol.

Results indicated that IL-18 alone stimulated IFNγ production and that IL-1 Hy2 had some inhibitory activities on the IL-18 stimulation. In order to assess the mechanism by which IL-1 Hy2 reduced FNy production, the following assay was carried out.

Human lymphocytes (PBMC) were obtained, washed, seeded, stimulated with anti-CD3 antibody and treated with a final concentration of 100 ng/ml IL-18 (R & D Systems) as described above. Several blocking antibodies were then used to test inhibition of IFNγ production, including anti-IL 18 receptor antibody, anti-IL-1 receptor accessory protein antibody, anti-Il-1 receptor type I antibody and anti-IL-1 receptor type II antibody (all obtained from R & D Systems, Minneapolis, Minn.). Different amounts of each antibody were added to the wells with IL-18, and after 36 hours of cell stimulation, the culture plate was centrifuged for 5 minutes at 4000 rpm to remove cell debris. The supernatant was assayed for IFNγ using the Quantikine IFNγ ELISA kit (R & D Systems) according to manufacturer's instructions.

In the absence of an antibody, IL-18 stimulated IFNγ production relative to background levels as observed above. However, anti-IL18 receptor antibody, anti-accessory protein antibody and anti-IL-1 receptor type I, but not type II, antibody inhibited IL-18 induced IFNγ production.

These results indicate that compounds which antagonize the action of the IL-1 receptor inhibit IL-18 activity as measured by induction of IFNγ production.

EXAMPLE 12

Binding of IL-1 Hy2 to the Interleukin-1 Receptor

A cell binding assay was carried out, in a modification of the procedure as described above in Example 7. 1, to determine if IL-1 Hy2 of the invention binds to the interleukin-1 (IL-1) receptor. Briefly, fluorescent activated cell sorting (FACS) was used to measure cell binding of the recombinant protein (see Example 6) using fluorescent antibodies specific for the express tag on the IL-1 Hy2 recombinant protein. In each reaction, $10^6$ cells of human fibroblast cells (CCD 1089) were suspended in 100 µl of FACS buffer (containing distilled PBS, 3% calf serum and 0.01% azide). Cell binding reactions included 5 nM recombinant IL-1 Hy2 in 100 µl cell suspension. The cells were incubated on ice for one hour. The cells were pelleted by centrifugation, 200 µl of 0.2 mM BS3 (crosslinker) was added, and the cells were kept on ice for 30 minutes. Next, 10 µl 1 M Tris pH 7.5 was added and the cells were incubated for 15 minutes on ice. The cells were pelleted by centrifugation, washed one time in FACS buffer, resuspended in 100 µl volume of FACS buffer, 2 µl primary antibody (anti-express tag antibody 1 mg/ml) was added, and incubation continued on ice for an additional 30 minutes. The cells were pelleted by centrifugation, washed with FACS buffer, and resuspended in FACS buffer (100 µl volume). The secondary antibody (phycoerythrin-conjugated), 2 µl of anti-mouse Ig (1 mg/ml), was added and the cells were incubated for 30 minutes on ice. The cells were again pelleted by centrifugation, washed two times with FACS buffer, resuspended in 0.5 ml FACS buffer and analyzed on FACS.

A shift in the fluorescence was observed for the cells treated with the recombinant tagged IL-1 Hy2. This binding was specific, as binding was not observed with the same molarity of non-related proteins, such as bovine serum-albumin (BSA). Specific IL-1 Hy2 binding was also demonstrated in the murine T cell line D10 and the murine monoclonal cell line RAW 264.7. These results indicate binding of the IL-1 Hy2 protein of the invention to the IL-1 receptor.

EXAMPLE 13

Expression of IL-Hy2 Polypeptide in Mammalian Cells

To express IL-1 Hy2 in mammalian cells, Chinese hamster ovary (CHO) cells were transfected with a mammalian expression vector and IL-1 Hy2 secretion was detected. The protein coding region of IL-2 Hy2 was obtained by PCR. The IL-2 Hy2 cDNA was used as a template for the IL-1 Hy2 specific primers (5' ATGGTTCCCTCCCCATGGCAAG3' and 5' GCTACCAGC TCTGTTCAAAGT AAAAC3'; SEQ ID NO: 19 and 20 respectively) designed to amplify the shorter ORF. The PCR reaction was run for 30 cycles at 94° C. for 30 seconds, 55° C. for 30 seconds and 72° C. for 30 seconds. The PCR product was inserted into the pcDNA3.1/V5-His-Topo vector (Invitrogen) per manufacturer's instructions. The resulting expression construct was sequenced to confirm that the inserted IL-1 Hy2 sequence was correct.

CHO cells were transiently transfected with the mammalian expression vector, pcDNA IL-1 Hy2, using the FuGene transfection reagent (Roche Molecular Biochemicals) according to manufacturer's instructions. The culture medium was collected 48 hours after the transfection and passed through a 0.2µ filter to remove cellular debris.

The collected conditioned medium was concentrated 10 fold using microcolumns (Amicon) according to the manufacturer's instructions and analyzed by electrophoresis on a 10% SDS-polyacrylamide gel followed by Western blot hybridization. IL-Hy2 was detected on the Western blot with a polyclonal antibody specific for IL-1 Hy2 using the BCIP/INBT (Sigma) according to the manufacturer's instructions. The polyclonal antibody used for the Western Blot was the IL-1 Hy2 specific antibody described in Example 3. The IL-1 Hy2 polypeptide was detected in both the cell culture medium and in the cell lysate, suggesting that IL-1 Hy2 is a secreted polypeptide of the apparent molecular weight 25 kD when expressed in mammalian cells. The IL-1 Hy2 polypeptide expressed in mammalian cells can be sequenced to confirm the amino terminus sequence of the mature protein.

The present invention is not to be limited in scope by the exemplified embodiments which are intended as illustrations of single aspects of the invention, and compositions and methods which are functionally equivalent are within the scope of the invention. Indeed, numerous modifications and variations in the practice of the invention are expected to occur to those skilled in the art upon consideration of the present preferred embodiments. Consequently, the only limitations which should be placed upon the scope of the invention are those which appear in the appended claims. All references cited within the body of the instant specification are hereby incorporated by reference in their entirety.

What is claimed is:

1. An isolated polynucleotide comprising a polynucleotide selected from the group consisting of:
   (a) a polynucleotide having the nucleotide sequence of SEQ ID NO: 1, 12 or 14;
   (b) a polynucleotide having the nucleotide sequence of the cDNA insert of clone pIL-1Hy2 (ATCC Accession No. PTA-96);
   (c) a polynucleotide having the IL-1Hy2 protein coding nucleotide sequence of a polynucleotide of (a) or (b).

2. An isolated polynucleotide which comprises a complement of the polynucleotide of claim 1.

3. An isolated polynucleotide encoding a polypeptide with IL-1Hy2 activity, comprising a polynucleotide selected from the group consisting of:
   (a) polynucleotides that encode the amino acid sequence of SEQ ID NO: 2;
   (b) polynucleotides that encode the amino acid sequence of SEQ ID NO: 13 and
   (c) polynucleotides that encode the protein encoded by the cDNA insert of clone pIL-1Hy2.

4. An isolated polynucleotide that specifically hybridizes to the complement of the polynucleotide of SEQ ID NO: 1, 12, or 14 under the following stringent conditions:
   (a) hybridization at 65° C. in a solution containing 0.5 M $NaHPO_4$, 7% sodium dodecyl sulfate (SDS), and 1 mM EDTA; and
   (b) washing at 68° C. in a solution containing 0.1×SSC and 0.1% SDS.

5. The polynucleotide of claim 3 which is selected from the group consisting of polynucleotides having the IL-1Hy2 protein coding sequence of SEQ ID NO: 1 and comprising one or more of the following nucleotide changes: T125C, C184T and A205C.

6. The polynucleotide of any one of claims 1 through 4 which is a DNA.

7. An expression vector comprising the DNA of claim 6.

8. A host cell genetically engineered to contain the DNA of claim 6.

9. A host cell genetically engineered to contain the DNA of claim 6 in operative association with a regulatory sequence that controls expression of the DNA in the host cell.

10. A method of producing IL-1Hy2 polypeptide wherein the method comprises:
   a) culturing the host cell of claim 9 for a period of time sufficient to express the polypeptide contained within said cell; and
   b) isolating the polypeptide from the cell of step a.

* * * * *

SEQUENCE LISTING

<160> NUMBER OF SEQ ID NOS: 20

<210> SEQ ID NO 1
<211> LENGTH: 998
<212> TYPE: DNA
<213> ORGANISM: Homo sapiens
<220> FEATURE:
<221> NAME/KEY: CDS
<222> LOCATION: (54)..(512)

<400> SEQUENCE: 1

```
ggttccagga actcaggatc tgcagtgagg accagacacc actgattgca g ga atg      56
                                                           Met
```

```
tgt tcc ctc ccc atg gca aga tac tac ata a tt aaa tat gca gac cag    104
Cys Ser Leu Pro Met Ala Arg Tyr Tyr Ile I le Lys Tyr Ala Asp Gln
              5                   10                15 aag gct cta tac aca aga gat ggc cag ctg c tg gtg gga gat cct gtt    152
Lys Ala Leu Tyr Thr Arg Asp Gly Gln Leu L eu Val Gly Asp Pro Val
         20                   25                 30 gca gac aac tgc tgt gca gag aag atc tgc a ca ctt cct aac aga ggc    200
Ala Asp Asn Cys Cys Ala Glu Lys Ile Cys T hr Leu Pro Asn Arg Gly
     35                   40                   45 ttg gac cgc acc aag gtc ccc att ttc ctg g gg atc cag gga ggg agc    248
Leu Asp Arg Thr Lys Val Pro Ile Phe Leu G ly Ile Gln Gly Gly Ser
 50                   55                   60                 65 cgc tgc ctg gca tgt gtg gag aca gaa gag g gg cct tcc cta cag ctg    296
Arg Cys Leu Ala Cys Val Glu Thr Glu Glu G ly Pro Ser Leu Gln Leu
              70                   75                80 gag gat gtg aac att gag gaa ctg tac aaa g gt ggt gaa gag gcc aca    344
Glu Asp Val Asn Ile Glu Glu Leu Tyr Lys G ly Gly Glu Glu Ala Thr
         85                   90                   95 cgc ttc acc ttc ttc cag agc agc tca ggc t cc gcc ttc agg ctt gag    392
Arg Phe Thr Phe Phe Gln Ser Ser Ser Gly S er Ala Phe Arg Leu Glu
    100                  105                  110 gct gct gcc tgg cct ggc tgg ttc ctg tgt g gc ccg gca gag ccc cag    440
Ala Ala Ala Trp Pro Gly Trp Phe Leu Cys G ly Pro Ala Glu Pro Gln
115                  120                  125 cag cca gta cag ctc acc aag gag agt gag c cc tca gcc cgt acc aag    488
Gln Pro Val Gln Leu Thr Lys Glu Ser Glu P ro Ser Ala Arg Thr Lys
130                  135                  140                  145 ttt tac ttt gaa cag agc tgg tag ggagacagga a actgcgttt tagccttgtg    542
Phe Tyr Phe Glu Gln Ser Trp
                150 cccccaaacc aagctcatcc tgctcagggt ctatggtagg cagaataatg t ccccgaaa    602 tatgtccaca tcctaatccc aagatctgtg catatgttac catacatgtc c aaagaggtt    662 ttgcaaatgt gattatgtta aggatcttga atgaggaga caatcctggg t tatccttgt    722 gggctcagtt taatcacaag aaggaggcag gaagggagag tcagagagag a atggaagat    782 accatgcttc taatttttgaa gatggagtga ggggccttga ccaacatat g caggtgttt    842 ttagaaggag gaaaagccaa gggaacggat tctcctctat agtctccgga a ggaacacag    902 ctcttgacac atggatttca gctcagtgac acccatttca gacttctgac c tccacaact    962 ataaaataat aaacttgtgt tattgtaaac ctctgg                              998

<210> SEQ ID NO 2
<211> LENGTH: 152
<212> TYPE: PRT
<213> ORGANISM: Homo sapiens

<400> SEQUENCE: 2

Met Cys Ser Leu Pro Met Ala Arg Tyr Tyr I le Ile Lys Tyr Ala Asp
 1               5                  10                   15

Gln Lys Ala Leu Tyr Thr Arg Asp Gly Gln L eu Leu Val Gly Asp Pro
             20                  25                   30

Val Ala Asp Asn Cys Cys Ala Glu Lys Ile C ys Thr Leu Pro Asn Arg
         35                  40                   45

Gly Leu Asp Arg Thr Lys Val Pro Ile Phe L eu Gly Ile Gln Gly Gly
     50                  55                   60

Ser Arg Cys Leu Ala Cys Val Glu Thr Glu G lu Gly Pro Ser Leu Gln
```

```
                65                  70                  75                  80
Leu Glu Asp Val Asn Ile Glu Glu Leu Tyr L ys Gly Gly Glu Glu Ala
                        85                  90                  95
Thr Arg Phe Thr Phe Gln Ser Ser Ser G ly Ser Ala Phe Arg Leu
                100                 105                 110
Glu Ala Ala Trp Pro Gly Trp Phe Leu C ys Gly Pro Ala Glu Pro
            115                 120                 125
Gln Gln Pro Val Gln Leu Thr Lys Glu Ser G lu Pro Ser Ala Arg Thr
        130                 135                 140
Lys Phe Tyr Phe Glu Gln Ser Trp
145                 150

<210> SEQ ID NO 3
<211> LENGTH: 998
<212> TYPE: DNA
<213> ORGANISM: Homo sapiens
<220> FEATURE:
<221> NAME/KEY: CDS
<222> LOCATION: (3)..(512)

<400> SEQUENCE: 3 gg ttc cag gaa ctc agg atc tgc agt gag ga c cag aca cca ctg att      47
   Phe Gln Glu Leu Arg Ile Cys Ser Glu  Asp Gln Thr Pro Leu Ile
    1               5                  10                  15 gca gga atg tgt tcc ctc ccc atg gca aga t ac tac ata att aaa tat    95
Ala Gly Met Cys Ser Leu Pro Met Ala Arg T yr Tyr Ile Ile Lys Tyr
             20                  25                  30 gca gac cag aag gct cta tac aca aga gat g gc cag ctg ctg gtg gga   143
Ala Asp Gln Lys Ala Leu Tyr Thr Arg Asp G ly Gln Leu Leu Val Gly
         35                  40                  45 gat cct gtt gca gac aac tgc tgt gca gag a ag atc tgc aca ctt cct   191
Asp Pro Val Ala Asp Asn Cys Cys Ala Glu L ys Ile Cys Thr Leu Pro
     50                  55                  60 aac aga ggc ttg gac cgc acc aag gtc ccc a tt ttc ctg ggg atc cag   239
Asn Arg Gly Leu Asp Arg Thr Lys Val Pro I le Phe Leu Gly Ile Gln
 65                  70                  75 gga ggg agc cgc tgc ctg gca tgt gtg gag a ca gaa gag ggg cct tcc   287
Gly Gly Ser Arg Cys Leu Ala Cys Val Glu T hr Glu Glu Gly Pro Ser
 80                  85                  90                  95 cta cag ctg gag gat gtg aac att gag gaa c tg tac aaa ggt ggt gaa   335
Leu Gln Leu Glu Asp Val Asn Ile Glu Glu L eu Tyr Lys Gly Gly Glu
                100                 105                 110 gag gcc aca cgc ttc acc ttc ttc cag agc a gc tca ggc tcc gcc ttc   383
Glu Ala Thr Arg Phe Thr Phe Phe Gln Ser S er Ser Gly Ser Ala Phe
            115                 120                 125 agg ctt gag gct gct gcc tgg cct ggc tgg t tc ctg tgt ggc ccg gca   431
Arg Leu Glu Ala Ala Ala Trp Pro Gly Trp P he Leu Cys Gly Pro Ala
        130                 135                 140 gag ccc cag cag cca gta cag ctc acc aag g ag agt gag ccc tca gcc   479
Glu Pro Gln Gln Pro Val Gln Leu Thr Lys G lu Ser Glu Pro Ser Ala
    145                 150                 155 cgt acc aag ttt tac ttt gaa cag agc tgg t ag ggagacagga aactgcgttt  532
Arg Thr Lys Phe Tyr Phe Glu Gln Ser Trp
160                 165                 170 tagccttgtg cccccaaacc aagctcatcc tgctcagggt ctatggtagg c agaataatg  592 tcccccgaaa tatgtccaca tcctaatccc aagatctgtg catatgttac c atacatgtc  652 caaagaggtt ttgcaaatgt gattatgtta aggatcttga aatgaggaga c aatcctggg  712 ttatccttgt gggctcagtt taatcacaag aaggaggcag gaagggagag t cagagagag  772
```

```
aatggaagat accatgcttc taattttgaa gatggagtga ggggccttga g ccaacatat      832 gcaggtgttt ttagaaggag gaaaagccaa gggaacggat tctcctctat a gtctccgga      892 aggaacacag ctcttgacac atggatttca gctcagtgac acccatttca g acttctgac      952 ctccacaact ataaaataat aaacttgtgt tattgtaaac ctctgg                      998
```

<210> SEQ ID NO 4
<211> LENGTH: 169
<212> TYPE: PRT
<213> ORGANISM: Homo sapiens

<400> SEQUENCE: 4

```
Phe Gln Glu Leu Arg Ile Cys Ser Glu Asp G ln Thr Pro Leu Ile Ala
 1               5                  10                  15

Gly Met Cys Ser Leu Pro Met Ala Arg Tyr T yr Ile Ile Lys Tyr Ala
             20                  25                  30

Asp Gln Lys Ala Leu Tyr Thr Arg Asp Gly G ln Leu Leu Val Gly Asp
         35                  40                  45

Pro Val Asp Asn Cys Cys Ala Glu Lys I le Cys Thr Leu Pro Asn
     50                  55                  60

Arg Gly Leu Asp Arg Thr Lys Val Pro Ile P he Leu Gly Ile Gln Gly
 65                  70                  75                  80

Gly Ser Arg Cys Leu Ala Cys Val Glu Thr G lu Glu Gly Pro Ser Leu
             85                  90                  95

Gln Leu Glu Asp Val Asn Ile Glu Glu Leu T yr Lys Gly Gly Glu Glu
            100                 105                 110

Ala Thr Arg Phe Thr Phe Phe Gln Ser Ser S er Gly Ser Ala Phe Arg
        115                 120                 125

Leu Glu Ala Ala Ala Trp Pro Gly Trp Phe L eu Cys Gly Pro Ala Glu
    130                 135                 140

Pro Gln Gln Pro Val Gln Leu Thr Lys Glu S er Glu Pro Ser Ala Arg
145                 150                 155                 160

Thr Lys Phe Tyr Phe Glu Gln Ser Trp
                165
```

<210> SEQ ID NO 5
<211> LENGTH: 155
<212> TYPE: PRT
<213> ORGANISM: Homo sapiens

<400> SEQUENCE: 5

```
Met Val Leu Ser Gly Ala Leu Cys Phe Arg M et Lys Asp Ser Ala Leu
 1               5                  10                  15

Lys Val Leu Tyr Leu His Asn Asn Gln Leu L eu Ala Gly Gly Leu His
             20                  25                  30

Ala Gly Lys Val Ile Lys Gly Glu Glu Ile S er Val Val Pro Asn Arg
         35                  40                  45

Trp Leu Asp Ala Ser Leu Ser Pro Val Ile L eu Gly Val Gln Gly Gly
     50                  55                  60

Ser Gln Cys Leu Ser Cys Gly Val Gly Gln G lu Pro Thr Leu Thr Leu
 65                  70                  75                  80

Glu Pro Val Asn Ile Met Glu Leu Tyr Leu G ly Ala Lys Glu Ser Lys
             85                  90                  95

Ser Phe Thr Phe Tyr Arg Arg Asp Met Gly L eu Thr Ser Ser Phe Glu
            100                 105                 110
```

```
Ser Ala Ala Tyr Pro Gly Trp Phe Leu Cys Thr Val Pro Glu Ala Asp
        115                 120                 125

Gln Pro Val Arg Leu Thr Gln Leu Pro Glu Asn Gly Gly Trp Asn Ala
    130                 135                 140

Pro Ile Thr Asp Phe Tyr Phe Gln Gln Cys Asp
145                 150                 155
```

<210> SEQ ID NO 6
<211> LENGTH: 178
<212> TYPE: PRT
<213> ORGANISM: Rattus rattus

<400> SEQUENCE: 6

```
Met Glu Ile Cys Arg Gly Pro Tyr Ser His Leu Ile Ser Leu Leu Leu
1               5                   10                  15

Ile Leu Leu Phe Arg Ser Glu Ser Ala Gly His Pro Ala Gly Lys Arg
                20                  25                  30

Pro Cys Lys Met Gln Ala Phe Arg Ile Trp Asp Thr Asn Gln Lys Thr
            35                  40                  45

Phe Tyr Leu Arg Asn Asn Gln Leu Ile Ala Gly Tyr Leu Gln Gly Pro
    50                  55                  60

Asn Thr Lys Leu Glu Glu Lys Ile Asp Met Val Pro Ile Asp Phe Arg
65                  70                  75                  80

Asn Val Phe Leu Gly Ile His Gly Gly Lys Leu Cys Leu Ser Cys Val
                85                  90                  95

Lys Ser Gly Asp Asp Thr Lys Leu Gln Leu Glu Glu Val Asn Ile Thr
                100                 105                 110

Asp Leu Asn Lys Asn Lys Glu Glu Asp Lys Arg Phe Thr Phe Ile Arg
            115                 120                 125

Ser Glu Thr Gly Pro Thr Thr Ser Phe Glu Ser Leu Ala Cys Pro Gly
    130                 135                 140

Trp Phe Leu Cys Thr Thr Leu Glu Ala Asp His Pro Val Ser Leu Thr
145                 150                 155                 160

Asn Thr Pro Lys Glu Pro Cys Thr Val Thr Lys Phe Tyr Phe Gln Glu
                165                 170                 175

Asp Gln
```

<210> SEQ ID NO 7
<211> LENGTH: 177
<212> TYPE: PRT
<213> ORGANISM: Sus scrofa

<400> SEQUENCE: 7

```
Met Glu Val Ser Arg Tyr Leu Cys Ser Tyr Leu Ile Ser Phe Leu Leu
1               5                   10                  15

Phe Leu Phe His Ser Glu Thr Ala Cys His Pro Leu Gly Lys Arg Pro
                20                  25                  30

Cys Arg Met Gln Ala Phe Arg Ile Trp Asp Val Asn Gln Lys Thr Phe
            35                  40                  45

Tyr Leu Arg Asn Asn Gln Leu Val Ala Gly Tyr Leu Gln Gly Pro Asn
    50                  55                  60

Thr Lys Leu Glu Glu Lys Ile Asp Val Val Pro Val Glu Pro His Phe
65                  70                  75                  80

Val Phe Leu Gly Ile His Gly Gly Lys Leu Cys Leu Ser Cys Val Lys
                85                  90                  95

Ser Gly Asp Glu Met Lys Leu Gln Leu Asp Ala Val Asn Ile Thr Asp
```

-continued

```
                  100                 105                 110
Leu Arg Lys Asn Ser Glu Gln Asp Lys Arg Phe Thr Phe Ile Arg Ser
            115                 120                 125
Asp Ser Gly Pro Thr Thr Ser Phe Glu Ser Ala Ala Cys Pro Gly Trp
        130                 135                 140
Phe Leu Cys Thr Ala Leu Glu Ala Asp Gln Pro Val Gly Leu Thr Asn
145                 150                 155                 160
Thr Pro Lys Ala Ala Val Lys Val Thr Lys Phe Tyr Phe Gln Gln Asp
                165                 170                 175
Gln
```

<210> SEQ ID NO 8
<211> LENGTH: 177
<212> TYPE: PRT
<213> ORGANISM: Homo sapiens

<400> SEQUENCE: 8

```
Met Glu Ile Cys Arg Gly Leu Arg Ser His Leu Ile Thr Leu Leu Leu
1               5                   10                  15
Phe Leu Phe His Ser Glu Thr Ile Cys Arg Pro Ser Gly Arg Lys Ser
            20                  25                  30
Ser Lys Met Gln Ala Phe Arg Ile Trp Asp Val Asn Gln Lys Thr Phe
        35                  40                  45
Tyr Leu Arg Asn Asn Gln Leu Val Ala Gly Tyr Leu Gln Gly Pro Asn
    50                  55                  60
Val Asn Leu Glu Glu Lys Ile Asp Val Val Pro Ile Glu Pro His Ala
65                  70                  75                  80
Leu Phe Leu Gly Ile His Gly Gly Lys Met Cys Leu Ser Cys Val Lys
                85                  90                  95
Ser Gly Asp Glu Thr Arg Leu Gln Leu Glu Ala Val Asn Ile Thr Asp
                100                 105                 110
Leu Ser Glu Asn Arg Lys Gln Asp Lys Arg Phe Ala Phe Ile Arg Ser
            115                 120                 125
Asp Ser Gly Pro Thr Thr Ser Phe Glu Ser Ala Ala Cys Pro Gly Trp
        130                 135                 140
Phe Leu Cys Thr Ala Met Glu Ala Asp Gln Pro Val Ser Leu Thr Asn
145                 150                 155                 160
Met Pro Asp Glu Gly Val Met Val Thr Lys Phe Tyr Phe Gln Glu Asp
                165                 170                 175
Glu
```

<210> SEQ ID NO 9
<211> LENGTH: 159
<212> TYPE: PRT
<213> ORGANISM: Homo sapiens

<400> SEQUENCE: 9

```
Met Ala Leu Glu Thr Ile Cys Arg Pro Ser Gly Arg Lys Ser Ser Lys
1               5                   10                  15
Met Gln Ala Phe Arg Ile Trp Asp Val Asn Gln Lys Thr Phe Tyr Leu
            20                  25                  30
Arg Asn Asn Gln Leu Val Ala Gly Tyr Leu Gln Gly Pro Asn Val Asn
        35                  40                  45
Leu Glu Glu Lys Ile Asp Val Val Pro Ile Glu Pro His Ala Leu Phe
    50                  55                  60
```

```
Leu Gly Ile His Gly Gly Lys Met Cys Leu Ser Cys Val Lys Ser Gly
 65                  70                  75                  80

Asp Glu Thr Arg Leu Gln Leu Glu Ala Val Asn Ile Thr Asp Leu Ser
                 85                  90                  95

Glu Asn Arg Lys Gln Asp Lys Arg Phe Ala Phe Ile Arg Ser Asp Ser
            100                 105                 110

Gly Pro Thr Thr Ser Phe Glu Ser Ala Ala Cys Pro Gly Trp Phe Leu
        115                 120                 125

Cys Thr Ala Met Glu Ala Asp Gln Pro Val Ser Leu Thr Asn Met Pro
    130                 135                 140

Asp Glu Gly Val Met Val Thr Lys Phe Tyr Phe Gln Glu Asp Glu
145                 150                 155
```

<210> SEQ ID NO 10
<211> LENGTH: 22
<212> TYPE: DNA
<213> ORGANISM: Artificial Sequence
<220> FEATURE:
<223> OTHER INFORMATION: Description of Artificial  Sequence:primer

<400> SEQUENCE: 10
ccgcaccaag gtccccattt tc                                          22

<210> SEQ ID NO 11
<211> LENGTH: 22
<212> TYPE: DNA
<213> ORGANISM: Artificial Sequence
<220> FEATURE:
<223> OTHER INFORMATION: Description of Artificial  Sequence:primer

<400> SEQUENCE: 11
gagcccacaa ggataaccca gg                                          22

<210> SEQ ID NO 12
<211> LENGTH: 1366
<212> TYPE: DNA
<213> ORGANISM: Homo sapiens

<400> SEQUENCE: 12
ggcagtggga ctgggtttga gctgggctta tcctccaact gtgagggagg c tacagcaca      60 ctccacccca ctctcagggc tgggaattgt tgtggctcag ctatttgggg g aatctgttt     120 tccagtttct cagaaccagc gcaagcacac acatcccagg ctcacacccc t ggtggctgg     180 acttgctccc ggatagcctc agtcagggag aggcagagct gcctggagcc t gctgggctg     240 gtggaagcct tggtggattc tggcaggcca attatagatg aatggcctgg g aacccgtg     300 cagcccgtgg ctgagtggtt ctaagcccca gcacgtctgc ctctggcttc a cccagcctc     360 cttttctaac tgcccttctc tcctccccat cagtgaggac cagacaccac t gattgcagg     420 aatgtgttcc ctccccatgg caagatacta cataattaaa tatgcagacc a gaaggctct     480 atacacaaga gacggccagc tgctggtggg agatcctgtt gcagacaact g ctgtgcaga     540 gaagatctgc acacttccta acagaggctt ggaccgcacc aaggtcccca t tttcctggg     600 gatccaggga gggagccgct gcctggcatg tgtggagaca aagagggggc c ttccctaca     660 gctggaggat gtgaacattg aggaactgta caaaggtggt gaagaggcca c acgcttcac     720 cttcttccag agcagctcag gctccgcctt caggcttgag ctgctgcctg g cctggctg     780 gttcctgtgt ggcccggcag agcccagca gccagtacga ctcaccaagg a gagtgagcc     840 ctcagcccgt accaagtttt actttgaaca gagctggtag ggagacagga a actgcgttt     900
```

```
tagccttgtg cccccaaacc aagctcatcc tgctcagggt ctatggtagg c agaataatg      960 tcccccgaaa tatgtccaca tcctaatccc aagatctgtg catatgttac c atacatgtc     1020 caaagaggtt ttgcaaatgt gattatgtta aggatcttga aatgaggaga c aatcctggg     1080 ttatccttgt gggctcagtt taatcacaag aaggaggcag gaaggagag t cagagagag     1140 aatggaagat accatgcttc taattttgaa gatggagtga ggggccttga g ccaacatat     1200 gcttgtgttt ttagaaggag gaaaagccaa gggaacggat tctcctctat a gtctccgga     1260 aggaacacag ctcttgacac atggatttca gctcagtgac acccatttca g acttctgac     1320 ctccacaact ataaataat aaacttgtgt tattgtaaac tctctgg                     1366
```

<210> SEQ ID NO 13
<211> LENGTH: 200
<212> TYPE: PRT
<213> ORGANISM: Homo sapiens

<400> SEQUENCE: 13

```
Met Asn Gly Leu Gly Asn Pro Cys Ser Pro T rp Leu Ser Gly Ser Lys
 1               5                  10                  15

Pro Gln His Val Cys Leu Trp Leu His Pro A la Ser Phe Ser Asn Cys
            20                  25                  30

Pro Ser Leu Leu Pro Ile Ser Glu Asp Gln T hr Pro Leu Ile Ala Gly
        35                  40                  45

Met Cys Ser Leu Pro Met Ala Arg Tyr Tyr I le Ile Lys Tyr Ala Asp
     50                  55                  60

Gln Lys Ala Leu Tyr Thr Arg Asp Gly Gln L eu Leu Val Gly Asp Pro
 65                  70                  75                  80

Val Ala Asp Asn Cys Cys Ala Glu Lys Ile C ys Thr Leu Pro Asn Arg
                 85                  90                  95

Gly Leu Asp Arg Thr Lys Val Pro Ile Phe L eu Gly Ile Gln Gly Gly
            100                 105                 110

Ser Arg Cys Leu Ala Cys Val Glu Thr Glu G lu Gly Pro Ser Leu Gln
        115                 120                 125

Leu Glu Asp Val Asn Ile Glu Glu Leu Tyr L ys Gly Gly Glu Glu Ala
    130                 135                 140

Thr Arg Phe Thr Phe Phe Gln Ser Ser Ser G ly Ser Ala Phe Arg Leu
145                 150                 155                 160

Glu Ala Ala Ala Trp Pro Gly Trp Phe Leu C ys Gly Pro Ala Glu Pro
                165                 170                 175

Gln Gln Pro Val Gln Leu Thr Lys Glu Ser G lu Pro Ser Ala Arg Thr
            180                 185                 190

Lys Phe Tyr Phe Glu Gln Ser Trp
        195                 200
```

<210> SEQ ID NO 14
<211> LENGTH: 1366
<212> TYPE: DNA
<213> ORGANISM: Homo sapiens

<400> SEQUENCE: 14

```
ggcagtggga ctgggtttga gctgggctta tcctccaact gtgagggagg c tacagcaca       60 ctccacccca ctctcagggc tgggaattgt tgtggctcag ctatttgggg g aatctgttt      120 tccagtttct cagaaccagc gcaagcacac acatcccagg ctcacacccc t ggtggctgg      180 acttgctccc ggatagcctc agtcagggag aggcagagct gcctggagcc t gctgggctg      240
```

```
gtggaagcct tggtggattc tggcaggcca attatagacg aatggcctgg g gaacccgtg      300 cagcccgtgg ctgagtggtt ctaagcccca gcacgtctgc ctctggcttc a cccagcctc      360 cttttctaac tgcccttctc tcctccccat cagtgaggac cagacaccac t gattgcagg      420 aatgtgttcc ctccccatgg caagatacta cataattaaa tatgcagacc a gaaggctct      480 atacacaaga gacggccagc tgctggtggg agatcctgtt gcagacaact g ctgtgcaga      540 gaagatctgc acacttccta acagaggctt ggaccgcacc aaggtcccca t tttcctggg      600 gatccaggga gggagccgct gcctggcatg tgtggagaca gaagaggggc c ttccctaca      660 gctggaggat gtgaacattg aggaactgta caaggtggt gaagaggcca c acgcttcac       720 cttcttccag agcagctcag gctccgcctt caggcttgag gctgctgcct g gcctggctg      780 gttcctgtgt ggcccggcag agccccagca gccagtacag ctcaccaagg a gagtgagcc      840 ctcagcccgt accaagtttt actttgaaca gagctggtag ggagacagga a actgcgttt      900 tagccttgtg cccccaaacc aagctcatcc tgctcagggt ctatggtagg c agaataatg      960 tccccccgaaa tatgtccaca tcctaatccc aagatctgtg catatgttac c atacatgtc     1020 caaagaggtt ttgcaaatgt gattatgtta aggatcttga aatgaggaga c aatcctggg     1080 ttatccttgt gggctcagtt taatcacaag aaggaggcag aagggagag t cagagagag      1140 aatggaagat accatgcttc taattttgaa gatggagtga ggggccttga g ccaacatat     1200 gcttgtgttt ttagaaggag gaaaagccaa gggaacggat tctcctctat a gtctccgga     1260 aggaacacag ctcttgacac atggatttca gctcagtgac acccatttca g acttctgac     1320 ctccacaact ataaaataat aaacttgtgt tattgtaaac ctctgg                     1366

<210> SEQ ID NO 15
<211> LENGTH: 5445
<212> TYPE: DNA
<213> ORGANISM: Homo sapiens

<400> SEQUENCE: 15
ctggactgga ccagcattga atttcttcca gctctttgag ctgacactga c ccagagtgg       60 gagtcatcag cttgctatcc accttcaccc agggccctcc actttgttgc c ccacctaga      120 tctgggcaca gctaccacac tgcccactgt cctgctgcta caaccaaaga a gccccagtg      180 gtttggccaa ggggagccca tcatcaagtg ggcttgcatt gaggccatga t gctgttgag      240 ttatctgtac tgggggattg tctagtcctt taggactcaa agtgctggcc a ggaggaacc      300 agcagcattg acatcacctg gttgcatatt tgaaatgtac agtctcaggc c ccaccccag      360 gcctgaaaaa ccagaatctg ttattttaac aagaactgca ggtggtttat a tatttatta      420 ataagtgtga agaatggaat gaaagtacat cagttcccaa gcagcatggc t gattgctgg      480 aatcactcca agtcctactg aattagaacc ttcggcccag gaaatagtaa t tatacagag      540 tcccccaggt gatgcagatg ggcaggcaca tttaggagcc aatgacttta a ctgaacact      600 tcatttaaaa aatgttgaaa cttacttgat actacaaagg aaattcatgt t cattatagg      660 aaaatgttga tatgtttaaa aaattactca taaagccata ggtaagtggt g caacaacac      720 gagtaacata tctatgtatg tgtctctatg tgtggattta aatagaatta c agtgtacac      780 ttgatttata atctgcattt ttcacctaat atattttgaa aattttatg t cctaaaaca      840 agcttctata atatcatctt taacaaacac atacatcctt atttattgaa t tttgctata     900 atttcttagc caattaccta ttactgaaaa ttcagatttt tttcaacttc t tgctattgt     960
```

-continued

| | | | | |
|---|---|---|---|---|
| aaaaaattat | gcagtgaaca | tttttgtaag | taaacatttg | ggcaatccgt t attttttcct | 1020 |
| aagagtaagg | gaaacacatg | caatcacaaa | gtatacagaa | tgctttaaga c tttcattca | 1080 |
| cagcaccaac | atccctccag | aatttgcact | tgttagtccc | tattatcctt c actctaagt | 1140 |
| ctcaaagtca | taccccaagg | cctggggaca | gaaaatgact | tgtccaaagt g acagtgaca | 1200 |
| gacccagtac | taaaagccac | cttggctaca | gccctgtttc | tggaacttga g tgctgaggt | 1260 |
| ggttggaagc | cgtatcctca | gcacccacct | gttccttctc | acctgcctcc c cagggtccc | 1320 |
| tcagcatctc | tctattcctc | cctgagccct | attactttct | tccacctgcc t tcttccttt | 1380 |
| ctcttctctc | attttctgct | tcttatatt | ttttcttctc | tattcccttc t tatttggtg | 1440 |
| agaatcagat | ctactcggta | aacctcagcc | ctagtcatac | ttgcgttact t tcctgagct | 1500 |
| aatttccaac | tcctgattag | ctctgggttt | atttccatgc | taaattctgg a ctggcctttt | 1560 |
| ccaatgggtg | ttcattttag | ggaagagctc | taggacagga | taacccatcg g gaaggagca | 1620 |
| gagtcatgtg | aggctgtgtg | gcctggcatt | tatacagggc | cactatcttc a ctgtgccat | 1680 |
| tttccatctg | gaacagaatg | ggggagtttg | gatgggctgt | tttcagcagt c ttggccaag | 1740 |
| cacttctagt | cactaggaat | gatgttttcc | aactctctgg | ggagacccca c cagcctcac | 1800 |
| tgctgctgga | gacccttcct | agttgtgctc | tcttctttca | ctctgggctc t agttatcta | 1860 |
| acccttggct | agttatgggg | gcggggtgt | ggtgccctgt | tggccaacag g gcagtggga | 1920 |
| ctgggtttga | gctgggctta | tcctccaact | gtgagggagg | ctacagcaca c tccacccca | 1980 |
| ctctcagggc | tgggaattgt | tgtggctcag | ctatttgggg | gaatctgttt t ccagtttct | 2040 |
| cagaaccagc | gcaagcacac | acatcccagg | ctcacacccc | tggtggctgg a cttgctccc | 2100 |
| ggatagcctc | agtcagggag | aggcagagct | gcctggagcc | tgctgggctg g tggaagcct | 2160 |
| tggtggattc | tggcaggcca | attatagatg | aatggcctgg | ggaacccgtg c agcccgtgg | 2220 |
| ctgagtggtt | ctaagcccca | gcacgtctgc | ctctggcttc | acccagcctc c ttttctaac | 2280 |
| tgcccttctc | tcctcccat | cagtgaggac | cagacaccac | tgattgcagg a atgtgttcc | 2340 |
| ctccccatgg | caagatacta | catgtaagtt | gtcctggcat | gtccctgctt t ccaagccag | 2400 |
| ggggtcaggg | tgggaagagg | aaaggaatgc | tgagtcagag | gatgaggctc c ttctcacct | 2460 |
| tagaaattgc | aagtgcccca | taattaagct | tcatcatcac | cacagtagca a cagctctttt | 2520 |
| cctgaacgtc | tgcaagatgc | cagccaatct | actgcctcat | ctctgttcca a aaagtctat | 2580 |
| aagtggagtg | ttattaaccc | cattttacag | atctggaagc | tgaggctcaa a gagggtaaa | 2640 |
| taacttcccc | catgtcacac | agctaccaaa | aggcagagcc | aggaatcaga c ttcatgtcc | 2700 |
| tctatgctgc | tccatccgcc | tctctgaaat | gtcagaaagt | tttgaatctc a atgacagca | 2760 |
| tcttgatggt | ggtccctgtg | gcctttactc | ccagtgtggg | cttctaacac t tacttacat | 2820 |
| ttcatctcat | ttgagatttg | catccttcct | tatcttttac | tactttgttg t ctgtgatttt | 2880 |
| tgtcataagc | tcctttcagg | aaggaggtga | ggcataagaa | aaatcaaaga g gactctggg | 2940 |
| atgcatttcc | tctgcccctc | ccatggaccc | tgtaatgtcc | agggctgtgt c ctggacaag | 3000 |
| gtgggtgggg | agcagtcctg | gtctcaagga | ggtgacagcc | tggctgggaa g caagacaca | 3060 |
| tacataggaa | gcacataaat | gacaaagcag | atgtcagcac | ttcagggcat c taatctggg | 3120 |
| ttctggtctc | caaatagaat | gctgctggca | tgtgagttgt | cacatctggg t tgtcaaggt | 3180 |
| ggcaagggga | atgccagtca | gcaagccag | gatctttccg | gaagtttatt t ttattgtac | 3240 |
| aagtgaacct | gctttaaata | tgtacagtca | ttagctaagg | gtattatcgt t agctgttat | 3300 |
| tgaggtagaa | aaatcccctg | gaggtggtgg | aatttgtcca | gaggttctgc c ctaaaaggt | 3360 |

-continued

```
taatgagagc tctccagccc tgacagcagc tgacaggcat ctttgaaacc a actaggtga   3420 ctgagctaat accctgcatg actttgaagc ctttaaaata tctgaaaagc a aatcacact   3480 tcagtataca ctcaattaat ctctgtacta aagagaataa acatttataa a caattaggg   3540 caggcccaaa aaatttaaga taaggtccac tgtatcccaa agtcatctga g cctcactaa   3600 gaaatttctc aggaagccag gaacattttc tttacccctc tgtcagaggg c attggctct   3660 ccgttctcct ctgaaggcct ccccaagcca tgagaaggca ggaagcacag c ctctgaaaa   3720 gcaagaacac aggagacctt ccttgcttta agactggcct ggtctttacc t gctcttggg   3780 agtgaccatt cccctcttac cacctgtgaa ggagagaaaa tcgcccaaat g ctcaaggtg   3840 gtgattcaga gcatggaagt ggaagggctt ggggccagt ggtgcataaa g ggaatgggc    3900 catcagcact gtcatactgt ttcagaatta aatatgcaga ccagaaggct c tatacacaa   3960 gagatggcca gctgctggtg ggagatcctg ttgcagacaa ctgctgtgca g gtgagcttc   4020 tgggcctcc accccatgct ccatctgcca taggccctcc cttctcttct t ccctttcct    4080 ccccagcaga gggtcagcag ctgcccccag tgacagtgag aagggccaga g agcagctgt   4140 ggcctctcct agcgagggga catgactcct gcagaagtcc tggctcaccg t ccagtctgc   4200 atgcagggcc aggccaggtg tgcccatgtc cagttccttc ctgcctgagc c tttacctgc   4260 caagagcctg caacatgggg ttccttgtc ccttgactct tctctctctt c cctcctaga    4320 gaagatctgc acacttccta acagaggctt ggaccgcacc aagtccccca t tttcctggg   4380 gatccaggga gggagccgct gcctggcatg tgtggagaca aagagggggc c ttccctaca   4440 gctggaggtg agaggcctct ccccattcta ggggacactg cagacctggc c tgaccccctg  4500 ggatgctctg gcatctttgt gcctatctgt ggattcccag ccaggtccac a tgtcctact   4560 tcctcaggtt tccaccatct ccctctgcac ctagcaccaa gacccttgcc c tctagaatc   4620 tgcagaaggc agtcccttgg gtaaaaacca gccctgtcag gtccttttt g gccaagccc    4680 cagaggcctc cagggctaac acctccatca gcactctcat tctgcagcca t ccaccttgc   4740 ccccacagga tgtgaacatt gaggaactgt acaaaggtgg tgaagaggcc a cacgcttca   4800 ccttcttcca gagcagctca ggctccgcct tcaggcttga ggctgctgcc t ggcctggct   4860 ggttcctgtg tggcccggca gagccccagc agccagtaca gctcaccaag g agagtgagc   4920 cctcagcccg taccaagttt tactttgaac agagctggta gggagacagg a aactgcgtt   4980 ttagccttgt gccccaaac caagctcatc ctgctcaggg tctatggtag g cagaataat    5040 gtcccccgaa atatgtccac atcctaatcc caagatctgt gcatatgtta c catacatgt   5100 ccaaagaggt tttgcaaatg tgattatgtt aaggatcttg aaatgaggag a caatcctgg   5160 gttatccttg tgggctcagt ttaatcacaa gaaggaggca ggaagggaga g tcagagaga   5220 gaatggaaga taccatgctt ctaattttga agatggagtg aggggccttg a gccaacaaa   5280 tgcaggtgtt tttagaaggt ggaaaagcca agggaacgga ttctcctcta g agtctccgg   5340 aaggaacaca gctcttgaca catggatttc agctcagtga cacccatttc a gacttctga   5400 cctccacaac tataaaataa taaacttgtg ttattgtaaa cctct          5445
```

<210> SEQ ID NO 16
<211> LENGTH: 4388
<212> TYPE: DNA
<213> ORGANISM: Mouse

<400> SEQUENCE: 16

-continued

```
ccatatcctt atttcctgga tttatcattc cctttcagcc gactggacat t gacagcatt      60
tccaacttt t caaccttgta aaataacta attgaactat tttataacta a gcatttggg     120
caatcaatta cctctgcctg gaatgggggc aacaacacat gcaatcatgg g aaagccagg    180
atgctgctgt ctgatcccta gccctggcat tcgtgcagaa cctcactctc a tctgtgccc    240
tgatatcctt cactctcaag tcttttccca gtgacttta aaggcaacag a atcatatag     300
ccaataatga aagctacttg gtctacagtt gtgtggcgtt tttatagat a ttttcatca    360
tttacattta aaatgcatat cccaaaagtc ccctataccc tcccccaccc t gctcccta    420
cccactgcac tcccacttct tggccctggc tttccccctt actggggcat a taaagtttg    480
ctagaccaag gggcctctct tcccaatgat ggccaactag gccattttct g ctacatatg    540
cagctagaga caccagttct ggggttactg gttagttcat attgttgttc t acctatggg   600
gttgcagacc ccttcagctc ttgagtactt tctctagctc ctccattggg a gccctgtgt    660
tccatcctat agatgactgt gagcatcccc ttctgtattt gcaggcgtgg c atatgaaat    720
agtatctgca tttggtggct gattatggga tggaccccg g gtggggcag t ctatggatg   780
gtccatcctt tcatcttagc tccaaacttt gtctctgcaa cttcttccat g gatatttta   840
gtccctaatc tagggaggaa tgaagtatcc ccaagttgat cttccttctt g attttctta   900
tgttttagca gttggatgtt ggatattata ggtttctggg ctaatatcca c ttatcagtg   960
agtacatatc aagtgaattc ttttgtgatt aggttacctc actcaagatg a tattctcca   1020
ctatgttcaa aacagcccta tttatagtag ccagaagact ggaaagaacc c agtccctca   1080
acagaggaat ggatacagaa aatgggcaca tttatgcaat ggagcccact c agatattaa   1140
aaacaacgaa tttatgaaat tctcgggcaa aaccctatct aaagccagga a taaggaaaa   1200
gatggactgc ctgcctgcag ctgggagagc tggggagacc tttgtggatt c tgtaatact   1260
tagggggtacg aacagcttg tggctggata attctgagct ccagcatgtc t gcccccaa   1320
aaaacattct gttttctga aagcctttt cttctttgcc tcagtgaaga c cagacactc    1380
ccaactgcag gaatgtgctc ccttcccatg gcaagatact acatgtaagt a atcttaacg   1440
atcgctcaat caaggggcct ggagatcaca tgagaaggga aaaggctgag t caaagggac   1500
aaagctccct ctagccacag aaatctcaaa cactgaataa ttgatcttca t ctttgtcaa   1560
tcacaacagc cctctttcct ggtgacagaa tggaacaact gtaagagtgg t attgcttag   1620
tccatttac agaccggaa actcaacctc cacgaggtta tacaatttc c tcatgtcat    1680
gcaattaccc aaaagcagag agtgggatcg gactctctgt tctctaaact g atgtagcta   1740
gttcttagaa agctcaaaca atcttgagtc ccaaggacag caccttatg g tcacctgga   1800
ttgataccta tatcaaaaaa aaaaaaggt ctcactagat agccctggct a ccctgaaac   1860
tctcactgtg tacatttagg tgaccacgaa ctcacagaga tctgccttcc a agtgctggg   1920
attaaagtat gtaccaccac acctgcatct ttgacaataa ctgagtggta t ctaaattct   1980
tccagtggct aaacagttaa gtcccagttc caaagtctg acaaaaatgc c aggtggctg   2040
aaatctgtac agacctttgt tcttaatgta caagtgagcc tgctttaaaa a caatacgca   2100
agctgttttt gctattgcta agtgttgcag agacagaaaa ggctcccaga a gtggtaact   2160
ttggtccaga ggttctgttc tcaaactcat tgtgagctct gaaagcaact g atgggcagc   2220
tctgaaatca gctgggcaat taggctaata acaggcataa ttttaatgtt t cacacgcat   2280
gacagttcct ccccagctgc cctagtacat acttaccctc ctaggcacgt c attagaccc   2340
ataggtataa ccagtgacta atcaggccct ggtctaattc taagttggcc t cctatataa   2400
```

```
gtgccactca gagtgtacct catcatggct gtagtgggcc cagagtctag g gacatagac    2460 ttttctattg tccaatttct gatttgtgaa ttttctacaa aaagaatttt t tttaatttt    2520 acaaatcaaa tcacagttac tacatcttca gttccttcat taattagtgt t actatttaa    2580 aaaaataaaa taaatcaagc tcagaaacat catggatagg gttcattgta t ctccagggt    2640 acctgagctt caaagcaact cctcagacag ccatgaaaac atcctcaatt a cctcatgag    2700 aagacactat tgtcatttct ggagcctctg ataatcctga gcctaggcag c tttgggatg    2760 aaacaatttc taccctattt ggaacagtgt ccctctcctg tctggaaaca a ttcaccaaa    2820 ggctccatgt ggttgtccag taaggtggta tggggacaga aatggacaat g atccctgag    2880 ggcagtgatc cattaacctt gccctcctat ttcagaatca aggatgcaca t caaaaggct    2940 ttgtacacac ggaatggcca gctcctgctg ggagaccctg attcagacaa t tatagtcca    3000 ggtgatcttc cggtggtggg ggtggggag tggaggggag ggtgtggggg g ggctctctt    3060 ccagaagttg cttagtgtcc atctgccaca aggccttgat tctttccttc a attgtgtct    3120 ctagagacat gagaatattg tcacagtgat aaggagaaga ggtaggggca g tttcttcct    3180 gtaaaaatg aattccattt accctgcagt ctccatacag aaacaggcca g aggggggca    3240 gacccagtaa cttctagctg agccctacct tgcttaaaac ctgccatctg t ggtcccctc    3300 actgtctgaa ttgcattctg tcttacctcc cagagaaggt ctgtatcctt c ctaaccgag    3360 gcctagaccg ctccaaggtc cccatcttcc tgggatgca gggaggaagt t gctgcctgg    3420 cgtgtgtaaa gacaagagag ggacctctcc tgcagctgga ggtgagacac c cctcctcat    3480 tgcagtcagt actgccactg gaacatagtg acatctttga acccacatgt c ccctctctt    3540 gtttcccatc tatctctctt tgcctccagc tgagggactc tagcctttgg g gatgtacag    3600 aaagaacatg gcttcggaaa actcttccct attgagtcct tctttggcca a gcctctgag    3660 gcactaaggg ctgacgtccc aaccaaacac tcatttcatc tcacagctgt c tccctttcc    3720 ccacaggatg tgaacatcga ggacctatac aaggaggtg aacaaaccac c cgtttcacc    3780 tttttccaga gaagcttggg atctgccttc aggcttgagg ctgctgcctg c cctggctgg    3840 tttctctgtg gcccagctga gccccagcag ccagtgcagc tcaccaaaga g agtgaaccc    3900 tccacccata ctgaattcta ctttgagatg agtcggtaaa gagacataag g ctgggcct    3960 cgtctagtgc ccccagtctg agatcttctt gctcagcatc tctggaaagc a gaataagga    4020 agataccaaa gatgtttggg tcttaatccc cagaatctgt gaccgtgtta c attaaatgg    4080 caagggatt ttttttttcc ttcatggtcc atttgggccc attggaatca t ctgaggcct    4140 catgaggaga aggaagaggt catgagggag actggcgcaa actttggtac t aaaagtaac    4200 aatggagaca gggaccataa gctgatgggt aacagtggtt tctagaaacc g gaaatgatg    4260 agagctctcc tgacacaggt gtctggattt ttctggactt aagaatggcg a aataataca    4320 gctccattat tttaagccac tgagtttgag atcattcaat gaagctgtca t aataaaacc    4380 tgtgcttc                                                              4388
```

<210> SEQ ID NO 17
<211> LENGTH: 459
<212> TYPE: DNA
<213> ORGANISM: Mouse

<400> SEQUENCE: 17

```
atgtgctccc ttcccatggc aagatactac ataatcaagg atgcacatca a aaggctttg    60
```

-continued

```
tacacacgga atggccagct cctgctggga gaccctgatt cagacaatta t agtccagag      120 aaggtctgta tccttcctaa ccgaggccta gaccgctcca aggtccccat c ttcctgggg      180 atgcagggag gaagttgctg cctggcgtgt gtaaagacaa gagagggacc t ctcctgcag      240 ctggaggatg tgaacatcga ggacctatac aagggaggtg aacaaaccac c cgtttcacc      300 tttttccaga gaagcttggg atctgccttc aggcttgagg ctgctgcctg c cctggctgg      360 tttctctgtg gcccagctga gccccagcag ccagtgcagc tcaccaaaga g agtgaaccc      420 tccacccata ctgaattcta ctttgagatg agtcggtaa                              459
```

<210> SEQ ID NO 18
<211> LENGTH: 152
<212> TYPE: PRT
<213> ORGANISM: Mouse

<400> SEQUENCE: 18

```
Met Cys Ser Leu Pro Met Ala Arg Tyr Tyr Ile Ile Lys Asp Ala His
 1               5                  10                  15

Gln Lys Ala Leu Tyr Thr Arg Asn Gly Gln Leu Leu Leu Gly Asp Pro
            20                  25                  30

Asp Ser Asp Asn Tyr Ser Pro Glu Lys Val Cys Ile Leu Pro Asn Arg
        35                  40                  45

Gly Leu Asp Arg Ser Lys Val Pro Ile Phe Leu Gly Met Gln Gly Gly
    50                  55                  60

Ser Cys Cys Leu Ala Cys Val Lys Thr Arg Glu Gly Pro Leu Leu Gln
65                  70                  75                  80

Leu Glu Asp Val Asn Ile Glu Asp Leu Tyr Lys Gly Gly Glu Gln Thr
                85                  90                  95

Thr Arg Phe Thr Phe Phe Gln Arg Ser Leu Gly Ser Ala Phe Arg Leu
            100                 105                 110

Glu Ala Ala Ala Cys Pro Gly Trp Phe Leu Cys Gly Pro Ala Glu Pro
        115                 120                 125

Gln Gln Pro Val Gln Leu Thr Lys Glu Ser Glu Pro Ser Thr His Thr
    130                 135                 140

Glu Phe Tyr Phe Glu Met Ser Arg
145                 150
```

<210> SEQ ID NO 19
<211> LENGTH: 23
<212> TYPE: DNA
<213> ORGANISM: Artificial Sequence
<220> FEATURE:
<223> OTHER INFORMATION: Description of Artificial  Sequence: primer

<400> SEQUENCE: 19

```
atgtgttccc tccccatggc aag                                                23
```

<210> SEQ ID NO 20
<211> LENGTH: 26
<212> TYPE: DNA
<213> ORGANISM: Artificial Sequence
<220> FEATURE:
<223> OTHER INFORMATION: Description of Artificial  Sequence: primer

<400> SEQUENCE: 20

```
gctaccagct ctgttcaaag taaaac                                             26
```